United States Patent
Luo et al.

(10) Patent No.: US 12,071,489 B2
(45) Date of Patent: Aug. 27, 2024

(54) METHODS OF CONVERTING BIOMASS NUCLEIC ACIDS AND CONVERTED BIOMASS NUCLEIC ACID PRODUCTS AND USES THEREOF

(71) Applicant: CORNELL UNIVERSITY, Ithaca, NY (US)

(72) Inventors: Dan Luo, Ithaca, NY (US); Dong Wang, Ithaca, NY (US)

(73) Assignee: Cornell University, Ithaca, NY (US)

( * ) Notice: Subject to any disclaimer, the term of this patent is extended or adjusted under 35 U.S.C. 154(b) by 147 days.

(21) Appl. No.: 17/318,845

(22) Filed: May 12, 2021

(65) Prior Publication Data

US 2021/0355246 A1    Nov. 18, 2021

Related U.S. Application Data

(60) Provisional application No. 63/023,819, filed on May 12, 2020.

(51) Int. Cl.
| | |
|---|---|
| *C08B 37/00* | (2006.01) |
| *B01D 11/02* | (2006.01) |
| *C08B 37/08* | (2006.01) |
| *C08J 3/09* | (2006.01) |

(52) U.S. Cl.
CPC ...... *C08B 37/0003* (2013.01); *B01D 11/0288* (2013.01); *C08B 37/003* (2013.01); *C08J 3/09* (2013.01); *C08J 2367/04* (2013.01)

(58) Field of Classification Search
CPC ....... C12P 19/34; C07H 21/00; C08B 37/003; C08B 37/0003; C08J 3/09; C08J 2367/04; B01D 11/0288
See application file for complete search history.

(56) References Cited

U.S. PATENT DOCUMENTS

| | | | |
|---|---|---|---|
| 6,585,873 B1 | 7/2003 | Solomon et al. | |
| 2008/0312174 A1 | 12/2008 | Yu et al. | |

FOREIGN PATENT DOCUMENTS

| | | |
|---|---|---|
| CN | 2750319 Y | 1/2006 |
| CN | 111040198 A | 4/2020 |
| CN | 112233535 A | 1/2021 |
| JP | 2001081098 A | 3/2001 |
| JP | 2008001763 A | 1/2008 |
| KR | 20180045191 A | 5/2018 |
| TW | 202102671 A | 1/2021 |
| WO | 2020236917 A1 | 11/2020 |

OTHER PUBLICATIONS

Nakano et al., Biophys. Rev., 2016, 8, p. 11-23. (Year: 2016).*
Gao et al., BioResources, 2013, 8(4), p. 5830-5391. (Year: 2013).*
Swiatkiewicz et al., Bull. Vet. Inst. Pulawy, 2010, 54, p. 237-242. (Year: 2010).*
Qin et al., BioResources, 2013, 8(4), p. 5369-5379. (Year: 2013).*
Yang et al., Acc. Chem. Res., 2014, 47, p. 1902-1911. (Year: 2014).*
Yumusak, et al., "Bio-organic field effect transistors based on crosslinked deoxyribonucleic acid (DNA) gate dielectric," Applied Physics Letters 95, 263304 (2009), all enclosed pages cited.
Roh, et al., "Engineering DNA-based functional materials," Chemical Society Reviews, 2011, 40, all enclosed pages cited.
Wang, et al., "Transformation of Biomass DNA into Biodegradable Materials from Gels to Plastics for Reducing Petrochemical Consumption," J.Am.Chem.Soc. 2020, 142, all enclosed pages cited.
Morikawa, et al. "DNA-Chitosan Hydrogels: Formation, Properties, and Functionalization with Catalytic Nanoparticles," ACS Appl. Bio Mater., 2021, 4, all enclosed pages cited.

* cited by examiner

*Primary Examiner* — Jonathan S Lau
(74) *Attorney, Agent, or Firm* — Hodgson Russ LLP

(57) ABSTRACT

Crosslinked nucleotide polymers. A crosslinked nucleotide polymer may be formed by reaction of a biomass comprising DNA and/or RNA with one or more crosslinker(s). A crosslinked nucleotide polymers may be formed by a crosslinking reaction including an aza-Michael addition reaction. Crosslinked nucleotide polymers may be present in various forms and compositions and form various articles of manufacture. Crosslinked nucleotide polymers may be used in therapeutic methods, coating methods, and cell-free protein production methods.

25 Claims, 47 Drawing Sheets

METHODS OF CONVERTING BIOMASS NUCLEIC ACIDS AND CONVERTED BIOMASS NUCLEIC ACID PRODUCTS AND USES THEREOF

CROSS-REFERENCE TO RELATED APPLICATIONS

This application claims the benefit of U.S. Provisional Application No. 63/023,819 filed May 12, 2020. The entire contents of the above-identified application are hereby fully incorporated herein by reference.

STATEMENT REGARDING FEDERALLY SPONSORED RESEARCH

This invention was made with government support under grant numbers 1530522 and 1844310 awarded by the National Science Foundation. The government has certain rights in the invention.

BACKGROUND OF THE DISCLOSURE

Petrochemical products are ubiquitous in daily life, dictating the pervasiveness of petrochemical-based materials in the many facets of our modern society. For example, materials in the forms of gels, membranes, and plastics have been extremely useful for real-world applications. Most of them are made from oil and gas, which are derived from ancient biomass through geological processes over hundreds of millions of years. They are inherently difficult to be degraded. Plastics, in particular, are increasingly polluting the earth's ecosystem with an estimated eight million or more metric tons of wastes flowing into oceans each year.

Biomass DNA comprises only about 3.1% of dry weight of a bacterium (similar percentage in other cells but much less in plants where cellulose contributes to most of the plant biomass). However, the total amount of biomass DNA on the earth is estimated at 50 billion metric tons, and less than 1% of this biomass DNA reserves is more than enough to meet the annual demand on the feedstock of world-wide commodity plastics production because our biomass DNA conversion approach is suitable for DNA from almost all organisms on the earth.

Biomass, a renewable and degradable resource, has been explored as an alternative candidate for replacing petrochemicals. The sum of the biomass from all taxa on Earth is about 550 gigatons of carbon, making biomass the most abundant sustainable material on Earth. Currently, biomass polysaccharide and protein have already been developed for bioplastics. However, there remain at least three significant issues: first, the main conversion approach has been very similar to the formation of petrochemicals, in which polymer chains need to be broken first before synthesizing the final plastics. The breakdown process of polymer chains requires extra energy and other resources with high temperatures. Second, the synthesis process of polymers involves a large amount of organic solvents, byproducts, and wastes. Third, the feedstocks are crops that are competing with agricultural resources including farmland and water. Consequently, even with advances in current biomass materials, there remain significant challenges in order to truly replace petrochemicals.

It is important to note that cellular biomass already exist in large scale from industry settings such as fermentation wastes (dregs and residues), food process waste (thymus, spleens, pomace, et al.), or environment such as bloomed algae. It is also important to note that these waste biomass enables the annual production of biomass DNA plastics at metric ton scale and that the high cell-density culture of microorganism has enough biomass DNA to substitute or replace petrochemical-based plastics in terms of annual demand on the feedstock of production.

Previous work treating DNA as a true polymer created dendrimer-like DNA, DNA hydrogels, protein-producing DNA gels, mechanical meta-hydrogels, and DNA-directed nanoparticle membranes. However, these previous DNA materials required careful sequence design and DNA syntheses from building blocks (nucleotides). As a result, they were too expensive to be feasibly translated to industrial scale in the foreseeable future.

SUMMARY OF THE DISCLOSURE

In an aspect, the present disclosure provides methods of converting biomass nucleic acids. A method may convert at least a portion of a biomass (e.g., the nucleotide polymers of a biomass) to a functional material (e.g., a crosslinked nucleotide polymer or the like). The biomass may be a DNA biomass, an RNA biomass, or the like, or a combination thereof. In certain examples, the biomass is converted into hydrogels, organogels, composite membranes, bioplastics, or the like. In various examples, a method comprises reaction of a crosslinker or crosslinkers with nucleic acids of a biomass. The nucleic acids may be present in nucleotide polymers (e.g., in DNA, RNA, or the like, or a combination thereof). The reaction may form crosslinked (e.g., covalently crosslinked) nucleic acids. The reaction may form polymeric materials comprising the nucleic acids and crosslinker group(s) formed from the crosslinker(s).

In an aspect, the present disclosure provides converted biomass nucleic acid products. In various examples, a converted biomass nucleic acid product is made by a method of the present disclosure. In various examples, a converted biomass nucleic acid product is a composition. A composition may be a printable composition. In various examples, a composition is a plastic or plastic material, a thermoset or thermoplastic polymer, a network polymer, a hydrogel or an organogel, a hybrid material, a composite material.

In an aspect, the present disclosure provides uses of converted biomass nucleic acid products. A therapeutic agent can be delivered using a converted biomass product. A method of treatment may comprise (or consist essentially of or consist of) administration of one or more converted biomass product(s), which may be in the form of one or more composition(s) of the present disclosure, comprising one or more therapeutic agent(s) to an individual. A converted biomass nucleic acid product may be used to coat a substrate. In various examples, a method of coating a substrate (e.g., a wire or the like) with a crosslinked nucleic acid polymer (e.g., a crosslinked DNA/RNA polymer) comprises contacting one or more converted biomass product(s) and/or one or more composition(s) comprising one or more converted biomass product(s) with a substrate.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Although claimed subject matter will be described in terms of certain examples, other examples, including examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include the lower limit value, the upper limit value, and all values between the lower limit value and the upper limit value, including, but not limited to, all values to the magnitude of the smallest value (either the lower limit value or the upper limit value) of a range.

As used herein, unless otherwise stated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent and multivalent, such as, for example, divalent radicals, trivalent radicals, and the like). Illustrative examples of groups include:

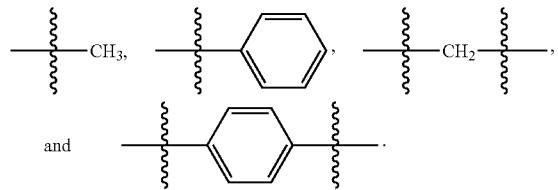

The present disclosure describes methods of converting biomass nucleic acids. The present disclosure also describes converted biomass nucleic acid products and uses of converted biomass nucleic acid products.

The present disclosure describes, inter alia, the use of biomass (e.g., biomass DNA, biomass, RNA, or the like or a combination thereof) to form various products. In various examples, a large-scale conversion of biomass DNA is carried out at low cost producing products, such as, for example, biomass DNA hydrogels, biomass DNA organosols, and degradable biomass DNA bioplastics, etc. The conversion may be carried out under simple and mild conversion conditions (e.g., pH 10-11, room temperature, etc.), without prior chemical modification of biomass DNA, short reaction time (e.g., cross-linking within minutes), and no removal of oxygen from reaction solution. The biomass DNA may be functionalized (e.g., via reaction of —C=C— bond).

Figures 1A, 1B:
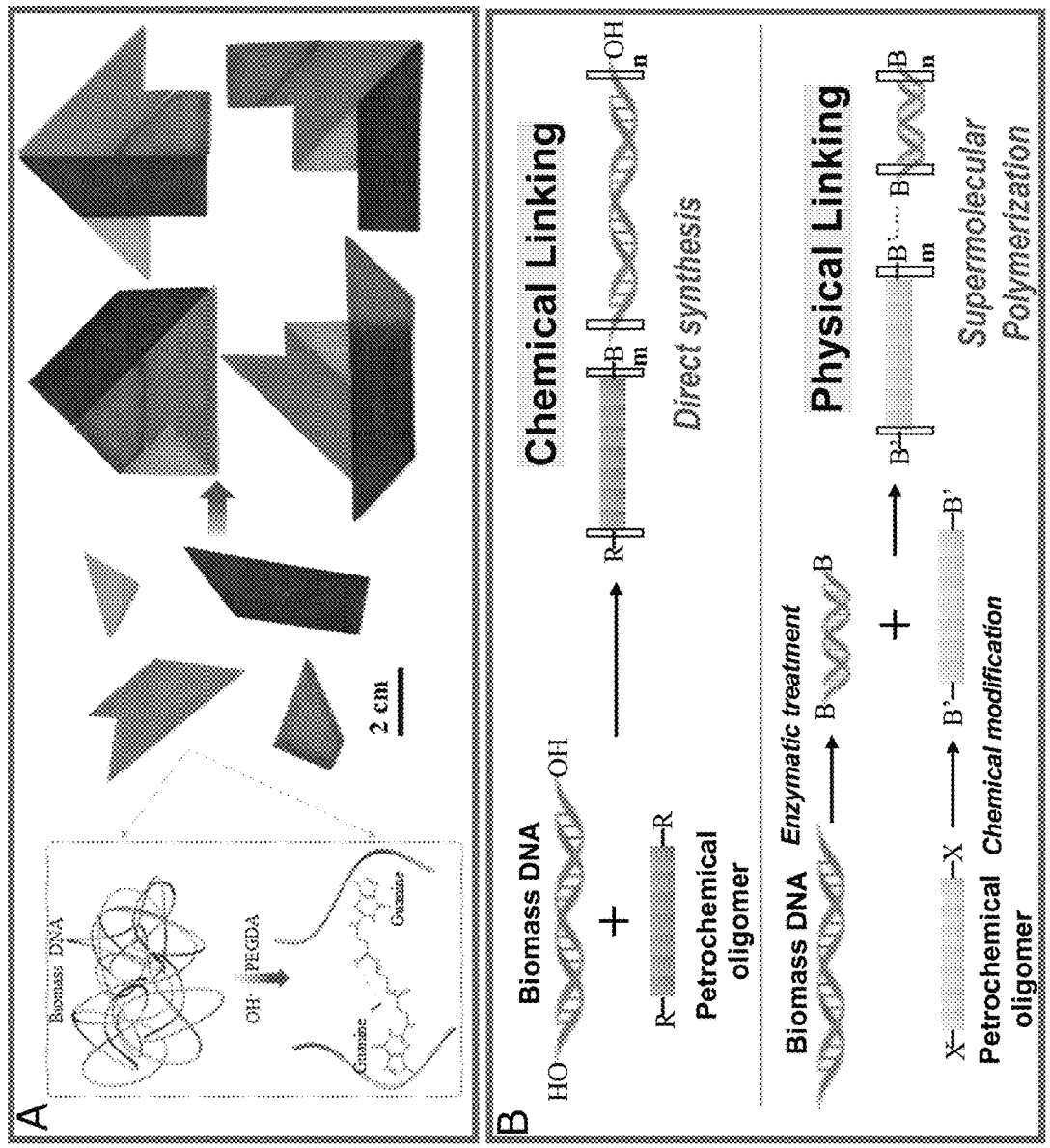
FIGS. 1A-1B show the approaches (no breakdown; no pretreatment) for producing (A) pure DNA plastics or (B) hybrid biomass DNA plastics via chemical or physical linking.

In various examples, without any DNA sequence design and without any DNA synthesis, biomass DNA was directly converted from different species spanning all kingdoms to create, at a large scale and with low cost to gels, membranes, plastics, etc. Taking advantage of biomass DNA, the present disclosure describes, inter alia, a unique strategy that provides a feasibility to achieve this, in which biomass DNA is directly converted to diverse materials without breaking down the DNA into building blocks and without polymer syntheses, in a total contrast to petrochemical processes and other biomass conversions (FIGS. 1A-1B). This facile approach has greatly reduced overall conversion costs, thus facilitating future industrialization.

Figure 2:
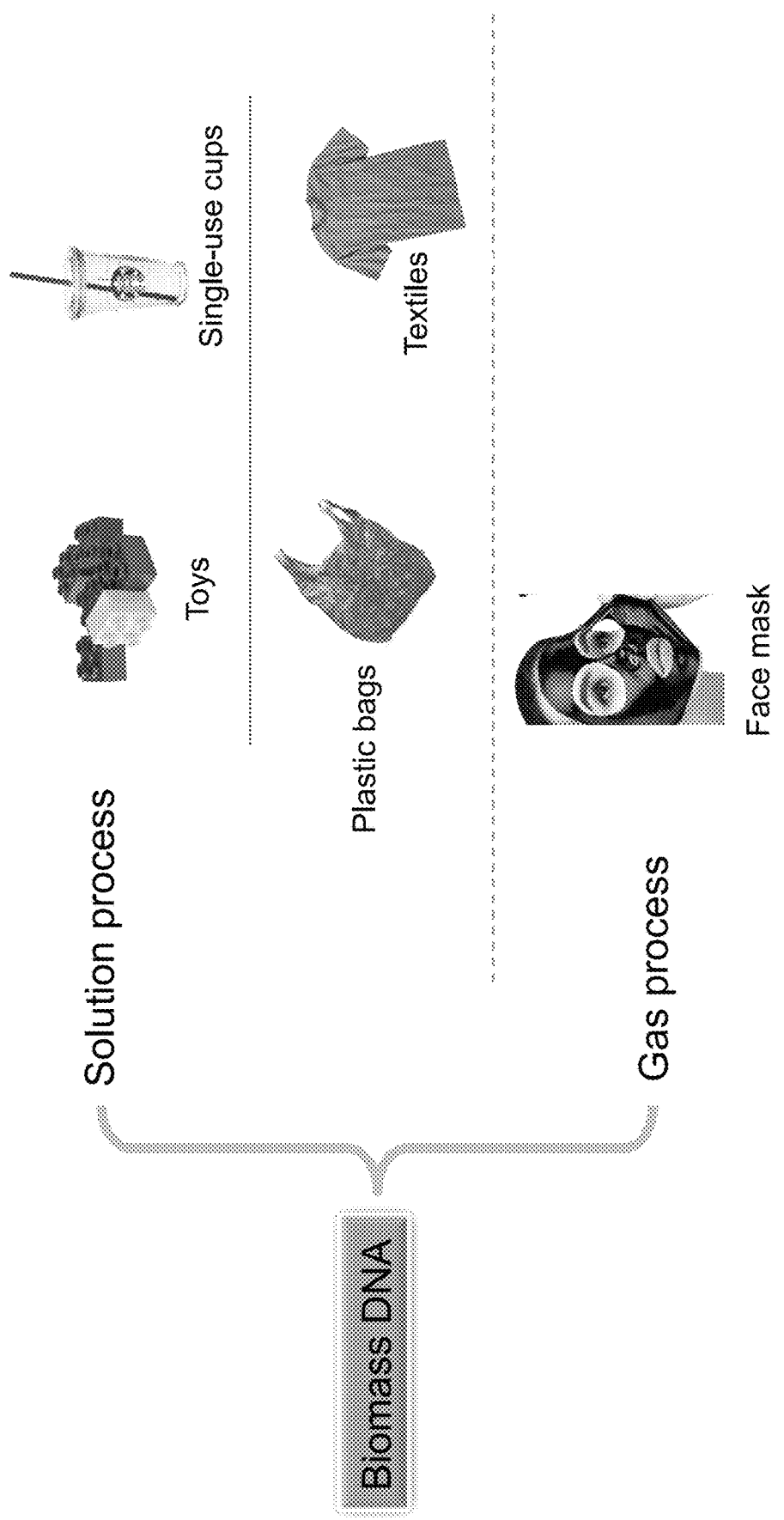
FIG. 2 shows products which can be produced from biomass DNA plastics using solution or gas processes.
Figure 3:
FIG. 3 shows a biomass DNA large-scale membrane.
Figure 4:
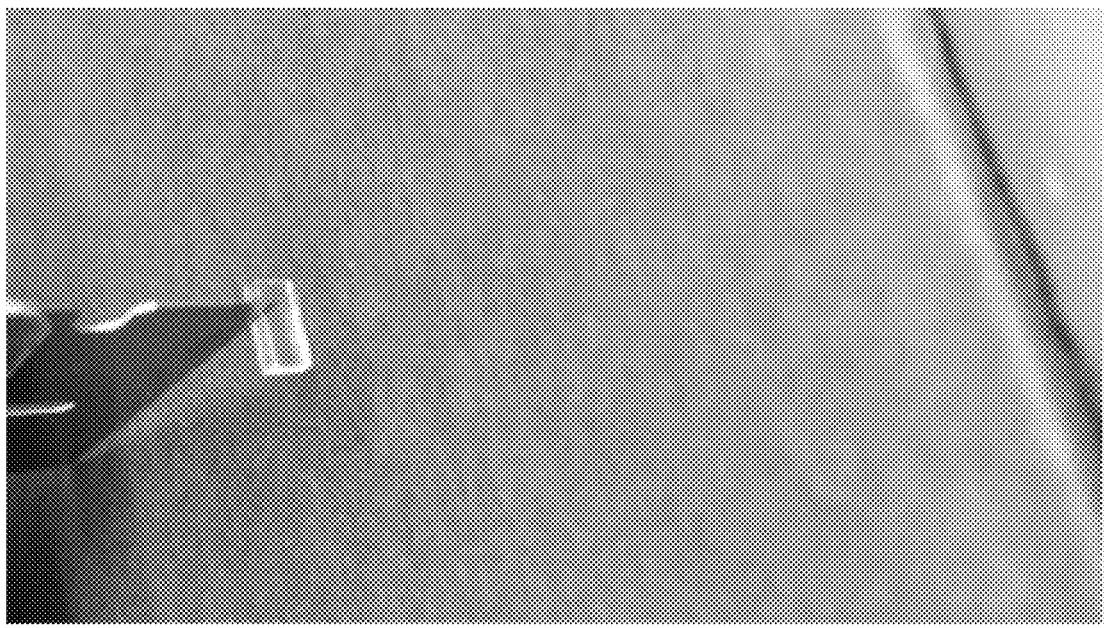
FIG. 4 show biomass DNA gels.
Figure 4:
Figure 5:
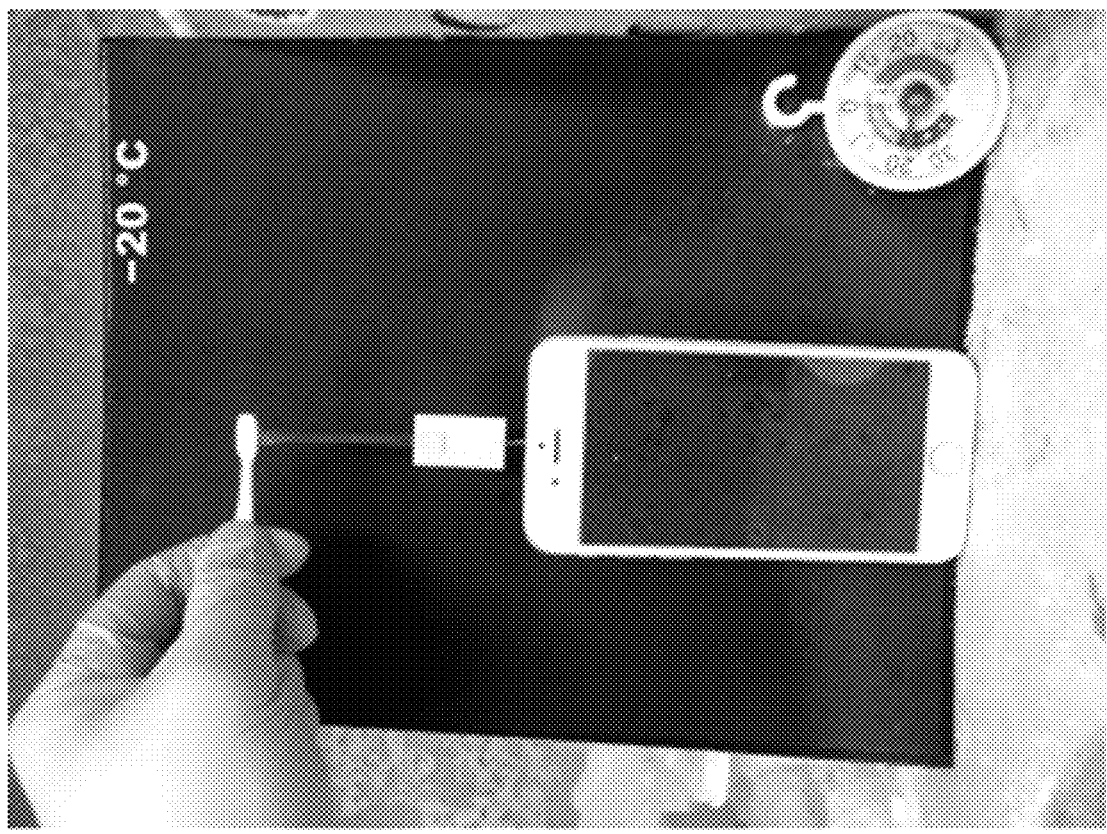
FIG. 5 shows biomass DNA specials gels (at −20° C.: non-brittle and super adhesive on non-sticky, Teflon surface).
Figure 5:
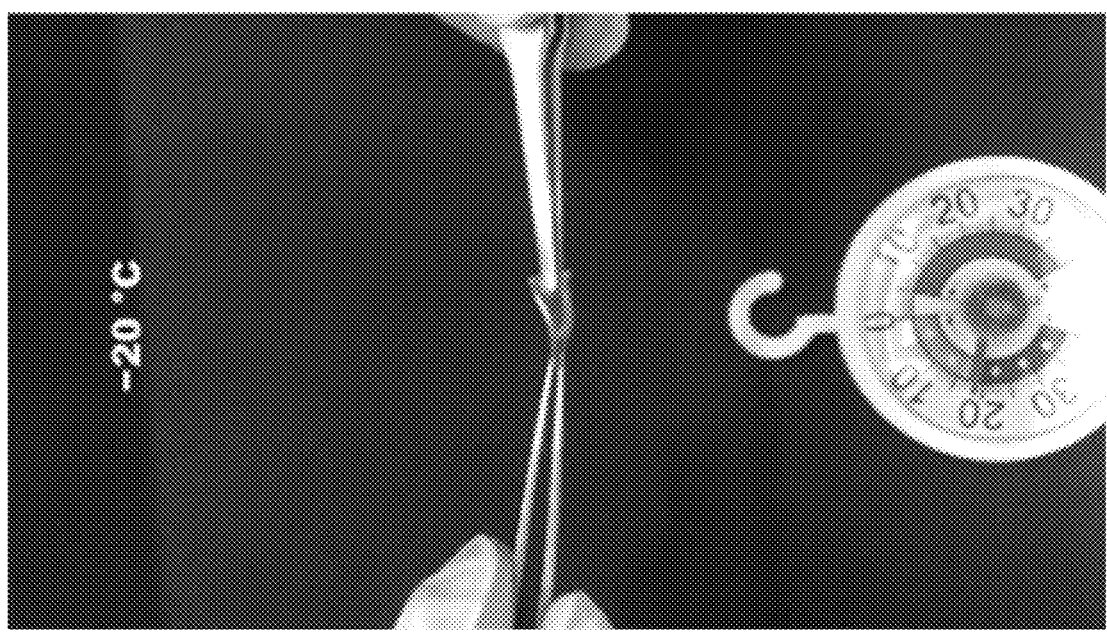
Figure 6:
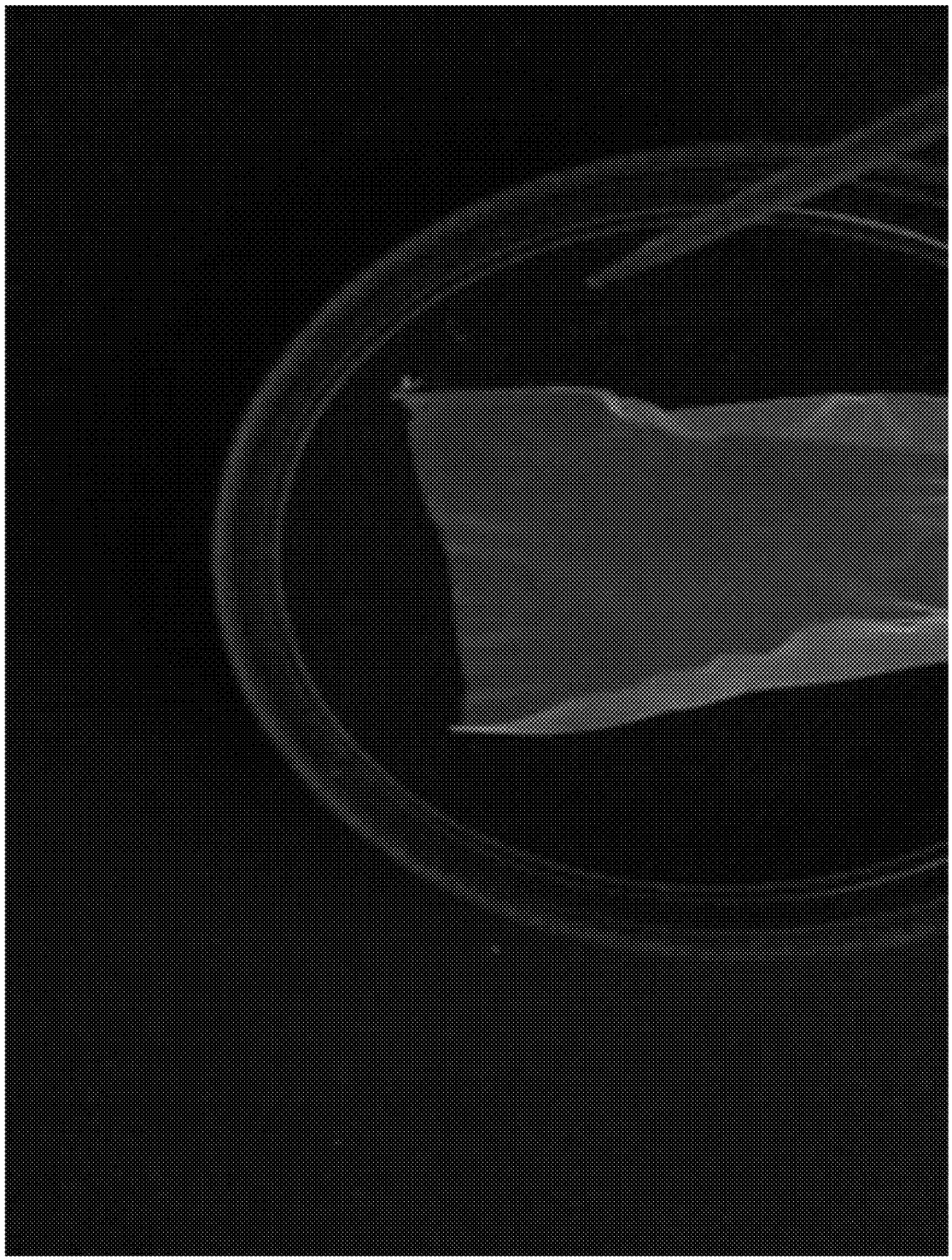
FIG. 6 shows biomass DNA tough thin membranes (textile).
Figure 7:
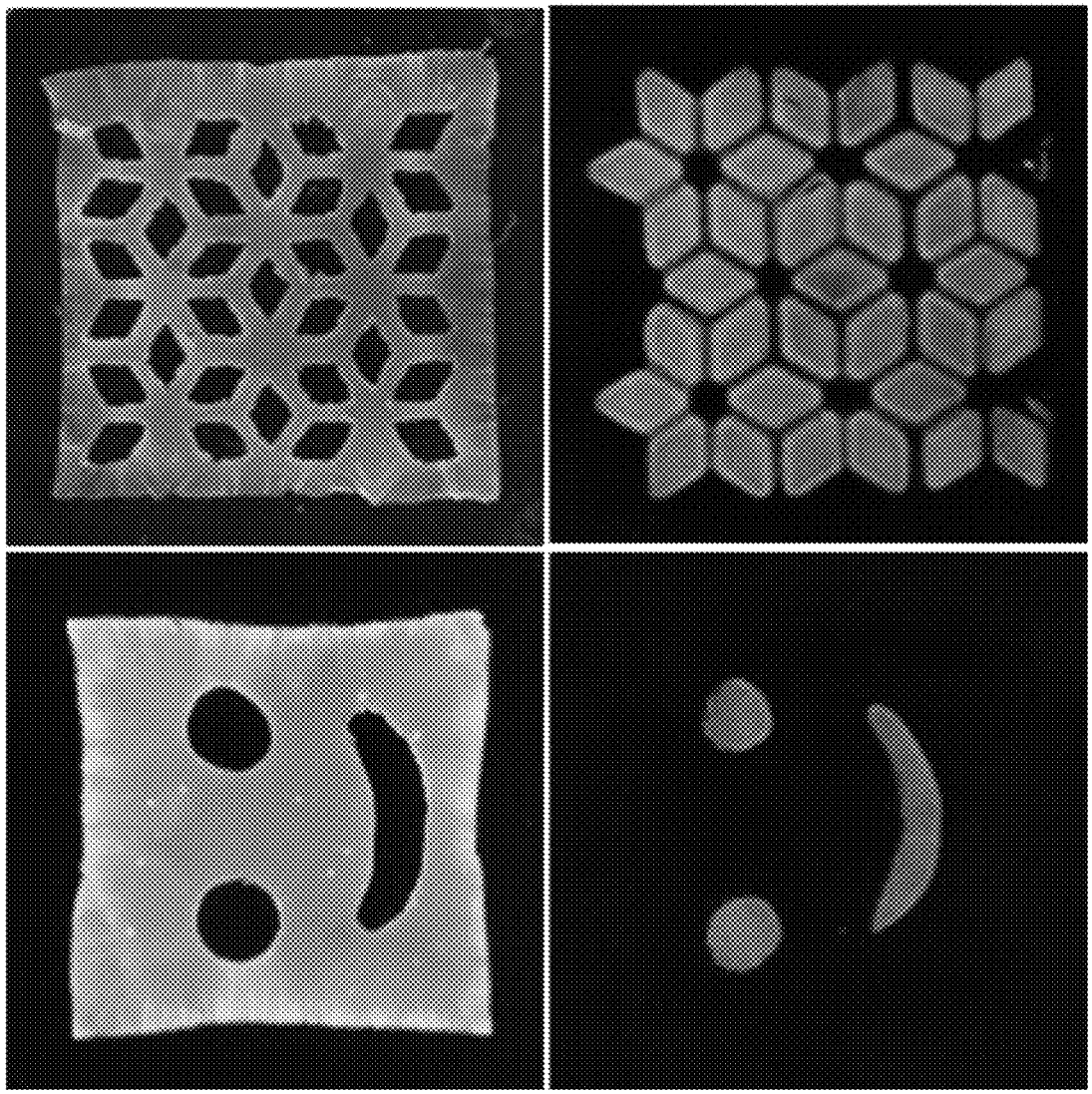
FIG. 7 shows patterning biomass DNA tough thin membrane hybrids.
Figure 8:
FIG. 8 shows biomass DNA composite materials.
Figure 9:
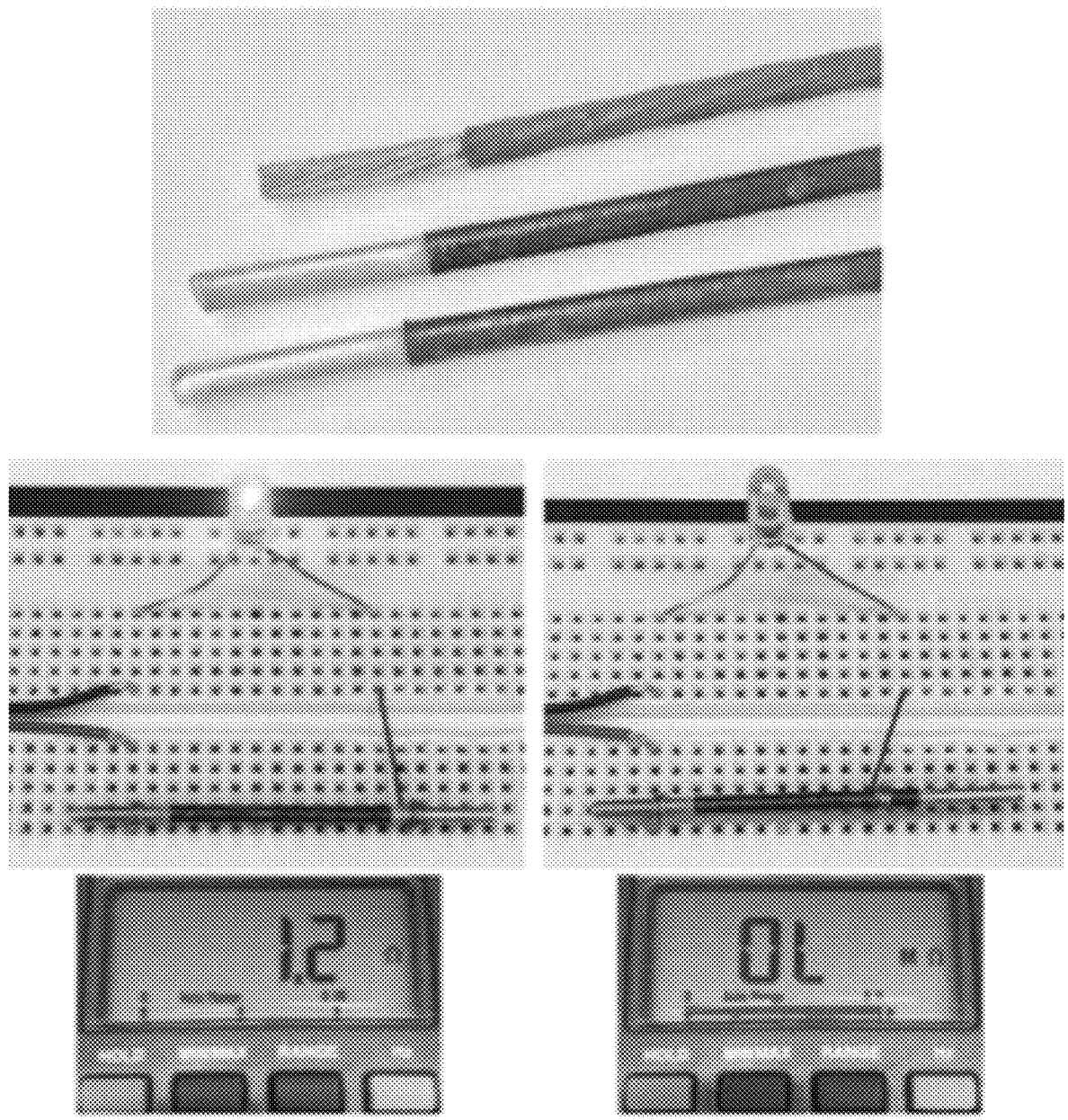
FIG. 9 shows biomass DNA plastic (1D).
Figure 10:
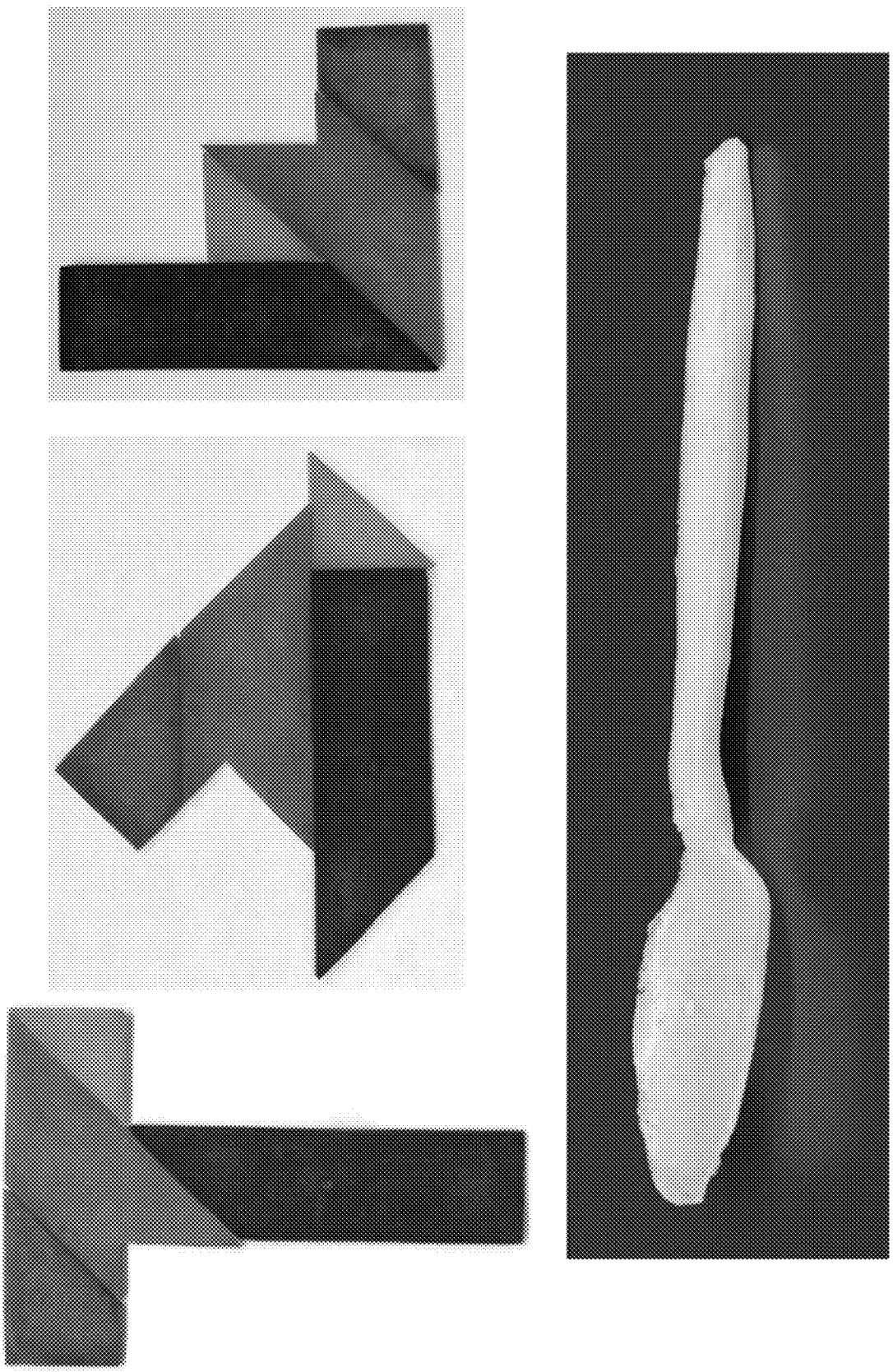
FIG. 10 shows biomass DNA plastics (2D and 3D).

In various examples, biomass DNA was directly converted into diverse materials including hydrogels, organogels, composite membranes, and plastics through facile, green, one-step crosslinking (FIGS. 3-10). The conversions were at a large scale with very low cost (FIG. 2). Biomass DNA materials presented desirable and, in certain instances, unexpected and useful properties. These materials were applied for versatile applications, such as, for example, for drug delivery, unusual adhesion, multifunctional composites, patterning, daily plastic objects, etc. In particular, cell-free protein production was achieved that is not attainable by petrochemical-based products. As DNA and RNA molecules themselves are polymers, and as DNA molecules are programmable and versatile with more than four thousand enzymes that catalyze different reactions, the biomass materials of the present disclosure have capabilities of being pre- or post-processed by enzymes and thus capable of reacting and/or hybridizing with other materials. Furthermore, taking advantages of DNA's genetic role, the biomass DNA materials of the present disclosure have the ability to interface with life directly and the potential of self-evolving. More types of biomass DNA/RNA materials are possible with desirable properties similar to or even better than petrochemical products.

In an aspect, the present disclosure provides methods of converting biomass nucleic acids. The nucleic acids may be present in a DNA (deoxyribonucleic acid) molecule/molecule (any of which may single stranded DNA or double stranded DNA) or in an RNA (ribonucleic acid) molecule or RNA molecules. The DNA and/or RNA may be biomass-derived DNA/RNA. Non-limiting examples of methods of converting biomass nucleic acids are described herein.

A method may convert at least a portion of a biomass (e.g., the nucleotide polymers of a biomass) to a functional material (e.g., a crosslinked nucleotide polymer or the like). The biomass may be a DNA biomass, an RNA biomass, or the like, or a combination thereof. In certain examples, the biomass is converted into hydrogels, organogels, composite membranes, bioplastics, or the like. In various examples, a method comprises reaction of a crosslinker or crosslinkers with nucleic acids (e.g., DNA nucleic acids, RNA nucleic acids, or a combination thereof) of a biomass. The nucleic acids may be present in nucleotide polymers (e.g., in DNA, RNA, or the like, or a combination thereof). The reaction may form crosslinked (e.g., covalently crosslinked) nucleic acids. The reaction may form polymeric materials comprising the nucleic acids and crosslinker group(s) formed from the crosslinker(s).

A converted biomass may comprise one or more crosslinked nucleotide polymer(s). The nucleotide polymer(s) may be biomass-derived nucleotide polymers. A crosslinked nucleotide polymer may be a biomass-derived crosslinked nucleotide polymer.

In various examples, a method of making a plurality of crosslinked nucleotide polymers, such as, for example, crosslinked DNA and/or RNA, and/or polymeric materials comprising nucleotide polymer groups, which may be crosslinked, (e.g., a composition comprising a plurality of crosslinked nucleotide polymers, such as, for example, crosslinked DNA and/or RNA and/or polymeric material(s), each polymeric material comprising nucleotide polymer groups, which may be crosslinked) comprises reacting a biomass comprising nucleotide polymers, such as, for example, DNA and/or RNA, and/or polymeric material(s) (or biomass-derived nucleotide polymers, such as, for example, biomass-derived DNA and/or biomass-derived RNA or the like), with one or more crosslinker(s), where a plurality of crosslinked nucleotide polymers, such as, for example, crosslinked DNA and/or RNA (e.g., a plurality of intramolecularly and/or intermolecularly crosslinked nucleotide polymers, such as, for example, crosslinked DNA and/or RNA) and/or polymeric material(s), each polymeric material comprising nucleotide polymer groups, which may be crosslinked (e.g., intramolecularly and/or intermolecularly crosslinked), is formed. The independent nucleotide polymer chains, such as, for example, DNA and/or RNA strands, or a portion thereof or the individual polymer chains of the polymeric material(s) may be crosslinked (e.g., covalently crosslinked) by one or more crosslinking groups. In various examples, the crosslinking is not initiated by exposure to electromagnetic radiation (e.g., light having a wavelength in the ultraviolet to visible region of the electromagnetic spectrum or the like). In various examples, oxygen is not removed from the reaction mixture prior to and/or during the crosslinking. In various examples, a method does not comprise sequencing of the DNA and/or RNA of the biomass (e.g., prior to and/or after the crosslinking reaction). In various examples, a method does not comprise DNA and/or RNA degradation (e.g., prior to and/or after the crosslinking reaction). In various examples, a method does not comprise DNA and/or RNA synthesis (e.g., prior to and/or after the crosslinking reaction). A biomass may or may not comprise intact cells.

A method may produce biomass-derived polymers. In various examples, a method of making a plurality of crosslinked biomass-derived nucleotide polymers comprises reacting a plurality of biomass-derived nucleotide polymers with one or more crosslinker(s), where a plurality of crosslinked biomass-derived nucleotide polymers is formed. The biomass-derived nucleotide polymers may have originated in a biomass. In various examples, the biomass-derived nucleotide polymers are extracted from a biomass. In various examples, the biomass-derived nucleotide polymers are present in a lysed biomass.

Various biomasses can be used. A biomass comprising nucleotide polymers, such as, for example, DNA and/or RNA, may be obtained from various sources. A biomass may comprise any suitable nucleotide polymers (e.g., DNA and/or RNA and the like). A biomass may comprise a plurality of amine functional groups (which may be referred to as an amine-functional biomass). A biomass may be a cellular biomass. In various examples, the biomass is not subjected to pretreatment (such as, for example, physical pretreatment, chemical pretreatment, biological pretreatment (e.g., fermentation), re-synthesis, or a combination thereof) and/or breakdown prior to reaction with crosslinker(s). In various examples, a biomass is sourced from any kingdom of life, including, but not limited to, *Bacteria, Archaea*, Protozoa, Chromista, Plantae, Fungi, Animalia, or a combination thereof. In various other examples, a biomass is sourced from a domain of life, including, but not limited to, *Bacteria, Archaea, Eucarya*, or a combination thereof. Non-limiting examples of biomass include bacteria (e.g., *E. coli* and the like), *archaea* (e.g., Haloarchaea and the like), protozoa, chromista, plantae (e.g., onions, fruits, other plants, and the like), fungi (e.g., yeast, algae, and the like), animalia (e.g., food waste from animals and the like). One or more or all of the biomass(es) may be renewable biomass(es).

Various crosslinkers can be used. Combinations of two more structurally distinct crosslinkers may be used. A crosslinker has two or more functional groups that can each react with a functional group of a nucleotide polymers, such as, for example, DNA and/or RNA, of the biomass and form an intramolecular crosslink or an intermolecular crosslink (which may be a covalent crosslink or a non-covalent (e.g., ionic) crosslink). In various examples, a crosslinker comprises a plurality of Michael acceptors. Non-limiting examples of functional groups include terminal carbon-carbon double bonds (e.g., a terminal carbon-carbon double bond of a methacrylate group and the like), ionic groups, and the like, and combinations thereof. In various examples, the no covalent bonds of the individual nucleotide polymer chains, such as, for example, DNA and/or RNA strands, are broken during the crosslinking process.

A crosslinker may comprise one or more Michael acceptor group(s). A Michael acceptor group may be referred to as a Michael addition acceptor group. A Michael acceptor group may be an activated alkene group. Non-limiting examples of Michael acceptor groups include alpha,beta unsaturated ketone groups, alpha,beta unsaturated aldehyde groups, alpha,beta unsaturated ester groups, alpha,beta unsaturated amide groups, alpha,beta unsaturated nitrile groups, nitro ethylene groups, and the like, and combinations thereof.

In various examples, the crosslinker(s) comprise polyethylene glycol dimethacrylate (PEGDMA), four-arm PEG acrylate, divinyl sulfone (DVS), or the like, or a combination thereof. A PEGDMA may have a molecular weight (e.g., an average Mn) of 250 to 10,000 g/mol, including all integer g/mol values and ranges therebetween. A PEG group of the PEGDMA or a four-arm PEG acrylate may comprise 2 to 250 ethyleneoxide groups, including all integer number of ethyleneoxide groups and ranges therebetween.

A crosslinker may be an oligomer or oligomers, a polymer or polymers, or a combination thereof. An oligomer or polymer may comprise two functional groups that can react with the nucleotide polymers, such as, for example, DNA and/or RNA, of the biomass and a polymer comprising a plurality of oligomer and/or polymer groups and a plurality of nucleotide polymer, such as, for example, DNA and/or RNA, groups is formed. In various examples, the individual oligomer(s) comprise two or more functional groups (e.g., Michael donor(s), Michael acceptor(s), or a combination thereof) react with individual nucleotide polymer chain, such as, for example, a DNA or RNA strand, of the biomass comprising one or more functional group(s) (e.g., Michael donor(s), Michael acceptor(s), or a combination thereof) via a Michael reaction, such as, for example, an aza-Michael addition, or the like. A polymer may be a copolymer (e.g., an alternating copolymer, block copolymer, or the like, or a combination thereof. Non-limiting examples of oligomer crosslinkers and polymer crosslinkers include hydrocarbon oligomers, hydrocarbon polymers, and the like, and combinations thereof. A hydrocarbon oligomers or hydrocarbon polymers may be substituted with various functional groups.

A polymer crosslinker may be a protein. Non-limiting examples of protein crosslinkers include bovine serum albumin (BSA), polysaccharides, and the like, and combinations thereof.

A biomass may comprise a plurality of amine groups and a crosslinker or crosslinkers may react with a plurality of amine groups of a biomass. It may be desirable that the biomass comprises a plurality of guanine nucleotides (e.g., a plurality of nucleic acid polymers comprising one or more guanine residues). The reaction between an amine group and a crosslinker may be an aza-Michael addition. In various examples, a plurality of amine groups (such as, for example, 2-amine groups of guanine residues) of the nucleic acid polymer(s) of biomass reacts with one or more (e.g., a plurality of) Michael acceptor groups of a crosslinker to form one or more (e.g., a plurality of) crosslinking group(s) (e.g., intramolecular and/or intermolecular crosslinking group(s)). The reaction between the amine group and the crosslinker may be an aza-Michael addition.

The biomass and crosslinker(s) may be present in a mixture (which may be referred to as a reaction mixture). The mixture may comprise one or more solvent(s), one or more or all of which may be organic solvent(s). Non-limiting examples of solvents include water, ionic liquids, organic solvents, and the like, and combinations thereof. In various examples, the mixture is an aqueous mixture. An aqueous mixture may have a pH greater than 7 or 7.2 (e.g., 7.5 to 12). Non-limiting examples of organic solvents include alcohols (e.g., glycerol and the like), formamide, and the like, and combinations thereof. Other non-limiting examples of organic solvents(s) include commonly used organic solvents in the art.

Without intending to be bound by any particular theory, it is considered the reaction of the crosslinker(s) and nucleotide polymers, such as, for example, DNA and/or RNA, may be triggered (e.g., initiated, catalyzed, or the like) by a base. A crosslinking reaction may be initiated, catalyzed, or the like, by a base. A reaction mixture may comprise one or more base(s). The base may be in a soluble/solution form or gaseous form. A base may be formed by contacting a reaction mixture with a gas, such as, for example, ammonia or the like. The base may be an aqueous base (e.g., hydroxide salt(s), which may be metal ion salts, ammonium ion salts, or the like, organic base(s), or the like, or a combination thereof), a gaseous base (e.g., ammonia or the like), or a combination thereof. The base may be present prior to added to a mixture of crosslinker(s) and biomass or present when the crosslinker(s) and biomass are combined.

A reaction mixture may comprise one or more additive(s). The additive(s) may be added to the reaction mixture before the crosslinking reaction and/or to a plurality of crosslinked DNA and/or RNA. Non-limiting examples of additive(s) include functional materials, inorganic materials (such as, for example, carbon materials (e.g., carbon nanotubes, such as, for example, single-wall carbon nanotubes, graphenes, graphene oxides), nanomaterials (such as, for example, cellulose nanocrystals, cellulose nanofibers, and the like), metal ions, clays, and the like, and combinations thereof), plasticizers (such as, for example, glycerol and the like), polymerizable monomers (which may be polymerized to form a conducting polymer, phosphorescent materials (such as, for example, rare earth compounds and the like), and the like, and combinations thereof. Addition of the additive(s) may result in formation of a composite material. Non-limiting examples of functional materials include colorants, dyes, small molecules (such as, for example, small molecule drugs and the like), particles, which may be nanoparticles, and the like, and combinations thereof. The particles may be metal or metal oxide particles, such as, for example, gold particles, iron oxide particles. The particles may be magnetic particles, and the like, and combinations thereof.

A method may comprise enzymatic treatment of the DNA and/or RNA biomass prior to reaction with the oligomer crosslinker(s) and/or polymer crosslinker(s) or after formation of the crosslinked nucleotide polymers, such as, for example, crosslinked DNA and/or RNA. The enzymatic treatment may form one or more ionic group(s), one or more hydroxyl group(s), one or more reactive groups, or the like on the individual nucleotide polymer chains, such as, for example, DNA or RNA strands, of the biomass. In this case, the oligomer may have two or more ionic groups and a polymer may be ionically crosslinked (such as, for example, crosslinked by one or more metal ion(s) (e.g., $Al^{3+}$, $Ca^{2+}$, or the like, or a combination thereof)) and the product may be referred to as a supermolecular polymer. The enzymatic treatment may form one or more reactive group(s) on a nucleotide polymer chain, such as, for example, a DNA or RNA strand, which may be further reacted to functionalize the individual nucleotide polymer chain, such as, for example, a DNA or RNA strand. A method may comprise reaction of or hybridization of nucleotide polymer chain(s), which may be crosslinked and/or subjected to enzymatic treatment, with one or more other material(s).

A method may comprise modifying at least a portion of or all of the nucleotide polymers, such as, for example, a DNA and/or RNA, of the biomass to form nucleotide polymers, such as, for example, a DNA and/or RNA, with one or more functional group(s) such that organic-soluble nucleotide polymers, such as, for example, a DNA and/or RNA, are formed.

The functional group(s) may be a hydrophobic group or hydrophobic group(s). Non-limiting examples of functional groups include aliphatic groups, aryl groups, and the like, and combinations thereof. As an illustrative example, functional group(s) are dodecyl groups, which may be formed by reaction with dodecyl acrylate.

A method may comprise isolation of the product(s) (e.g., plurality of crosslinked nucleotide polymers, such as, for example, crosslinked DNA and/or RNA (e.g., a plurality of intramolecularly and/or intermolecularly crosslinked nucleotide polymers, such as, for example, crosslinked DNA and/or RNA) and/or polymeric material(s), each polymeric material comprising nucleotide polymer groups, which may be crosslinked (e.g., intramolecularly and/or intermolecularly crosslinked)). Suitable methods, processes, and the like, for isolation of the product(s) are known in the art.

A method may comprise patterning the product(s). Patterning methods are described herein. Suitable patterning methods are known in the art.

In an aspect, the present disclosure provides converted biomass nucleic acid products. In various examples, a converted biomass nucleic acid product is made by a method of the present disclosure. Non-limiting examples of converted biomass nucleic acid products are described herein.

In various examples, a converted biomass nucleic acid product is a composition. A composition may be a printable composition. In various examples, a composition is a plastic or plastic material, a thermoset or thermoplastic polymer, a network polymer, a hydrogel or an organogel, a hybrid material, a composite material, or the like. A composition comprising one or more additive(s) may be a composite material. A composition may be disposed on at least a portion of or all of a surface or surfaces of a substrate.

A composition may comprise one or more solvent(s), one or more additive(s), or the like, or a combination thereof. Non-limiting examples of additive(s) include functional additives, inorganic materials (such as, for example, carbon materials (e.g., carbon nanotubes, such as, for example, single-wall carbon nanotubes), clays, and the like, and combinations thereof), and the like, and combinations thereof. Non-limiting examples of functional materials include colorants, dyes, fluorophores, phosphorescent materials (such as, for example, rare earth ions), small molecules (such as, for example, small molecule drugs and the like), particles, which may be nanoparticles, and the like, and combinations thereof. The particles may be magnetic particles, and the like, and combinations thereof.

A composition can have various forms. In various examples, a composition is in the form of a film (which may be a free-standing film that may be disposed on at least a portion of or all of a surface or surfaces of a substrate), a membrane, a coating, a thread, a fiber (which may be a hollow fiber), a monolith, a three-dimensional structure, or the like, or a combination thereof. A composition may be in the form of a pattern. In various other examples, a composition is a liquid or a fluid. In various other examples, a composition is a solution, a suspension, or the like.

A composition may be amorphous, crystalline (e.g., single-crystalline or polycrystalline), or a combination thereof. A composition may have one or more domain(s). The domain(s) may, independently, be amorphous or crystalline (e.g., single-crystalline or polycrystalline).

A composition may have desirable properties. In various examples, a composition exhibits one or more or all of the following: desirable degradation and/or biodegradability; desirable elastic modulus; desirable glass transition temperature (Tg); desirable optical property(ies) (e.g., optical transparency and the like); surface property(ies) (e.g., adhesive, non-stick, and the like); and/or the like.

In various examples, a converted biomass product is an article of manufacture. The article of manufacture may be a disposable article of manufacture. The article of manufacture may be a single-use article of manufacture. An article of manufacture may be formed by an additive manufacturing process (e.g., a 3D printing process or the like).

In an aspect, the present disclosure provides uses of converted biomass nucleic acid products. Non-limiting examples of uses of converted biomass nucleic acid products are described herein.

A therapeutic agent can be delivered using a converted biomass product. A method of treatment may comprise (or consist essentially of or consist of) administration of one or more converted biomass product(s), which may be in the form of one or more composition(s) of the present disclosure, comprising one or more therapeutic agent(s) to an individual. In various examples, a converted biomass product is a nucleotide hydrogel (e.g., a DNA and/or RNA hydrogel) (as described herein) further comprising a therapeutic agent (such, for example, insulin and the like). The therapeutic agent may be incorporated (e.g., soaked or the like) into the DNA/RNA hydrogel. In various examples, a method of treating an individual (which may be a controlled drug release method) comprises administering a therapeutic to a subject using the nucleotide hydrogel.

An individual (e.g., an individual in need of treatment or the like) may be a human or other animal (which may be a non-human mammal). Non-limiting examples of non-human animals (which may be mammals) include cows, pigs, mice, rats, rabbits, cats, dogs, and other agricultural animals, pets (such as, for example, dogs, cats, and the like), service animals, and the like.

Converted biomass products comprising one or more therapeutic agent(s) can be administered to an individual by any suitable route—either alone or as in combination with other agents. Administration can be accomplished by any means, such as, for example, by parenteral, topical, transdermal, catheter-based, oral means of delivery, or the like. Parenteral delivery may include, for example, subcutaneous, intravenous, intramuscular, intra-arterial, and injection into the tissue of an organ. Oral delivery can include delivery of a pill, which may be an enteric coated pill, administration of a liquid by mouth, or the like. Transdermal delivery may include delivery via the use of dermal patches.

A physician or veterinarian having ordinary skill in the art can readily determine and prescribe the effective amount of the compound(s) and/or composition(s) required. The selected dosage level can depend upon a variety of factors including, but not limited to, the activity of the particular composition employed, the time of administration, the rate of excretion or metabolism of the particular composition being employed, the rate and extent of absorption, the duration of the treatment, other drugs, compounds and/or materials used in combination with the particular composition employed, the age, sex, weight, condition, general health and prior medical history of the patient being treated, and like factors well known in the medical arts. For example, the physician or veterinarian could start doses of the composition employed at levels lower than that required in order to achieve the desired therapeutic effect and gradually increase the dosage until the desired effect is achieved.

A converted biomass nucleic acid product may be used to coat a substrate. In various examples, a method of coating a substrate (e.g., a wire or the like) with a crosslinked nucleic acid polymer (e.g., a crosslinked DNA/RNA polymer) comprises contacting one or more converted biomass product(s) and/or one or more composition(s) comprising one or more converted biomass product(s) with a substrate. The product(s) and/or composition(s) can be coated by methods known in the art.

A converted biomass nucleic acid product may be used to express protein in a cell-free environment. In various examples, a method of expressing protein in a cell-free environment comprises forming a covalent conjugate of a nucleotide hydrogel with a plasmid capable of expressing a target protein, where the covalent conjugate is capable of expressing the target protein in a cell-free environment. In various examples, the formation of the covalent conjugate comprises digesting the nucleotide hydrogel and/or the plasmid capable of expressing the target protein, where nucleotide hydrogel oligomers and/or plasmid oligomers are formed, and ligating the digested nucleotide hydrogel with the digested plasmid, where the covalent conjugate is formed. In various examples, expression of the target protein in the cell-free environment is performed by incubating the covalent conjugate in a solution comprising cell-free lysate, a reaction buffer, and nuclease-free water.

The following Statement describe examples of methods, compositions and uses thereof, and articles of manufacture of the present disclosure:

Statement 1. A method of making a plurality of crosslinked nucleotide polymers, such as, for example, crosslinked DNA and/or RNA, and/or polymeric materials comprising nucleotide polymer groups, which may be crosslinked, (e.g., a composition comprising a plurality crosslinked nucleotide polymers, such as, for example, crosslinked DNA and/or RNA and/or polymeric material(s), each polymeric material comprising nucleotide polymer groups, which may be crosslinked) comprising: reacting a biomass comprising nucleotide polymers, such as, for example, DNA and/or RNA, with one or more crosslinker(s), where a plurality of crosslinked nucleotide polymers, such as, for example, crosslinked DNA and/or RNA (e.g., a plurality of intramolecularly and/or intermolecularly crosslinked nucleotide polymers, such as, for example, crosslinked DNA and/or RNA) and/or polymeric material(s), each polymeric material comprising nucleotide polymer groups, which may be crosslinked (e.g., intramolecularly and/or intermolecularly crosslinked), is formed.

Statement 2. A method according to Statement 1, where the biomass and crosslinker(s) are present in a mixture and the mixture comprises one or more solvent(s).

Statement 3. A method according to Statement 2, where the solvent(s) is/are chosen from water, ionic liquids, and the like, and combinations thereof.

Statement 4. A method according to Statement 2, where the mixture is an aqueous mixture and the pH of the mixture is greater than 7 or 7.2 (e.g., 7.5 to 12).

Statement 5. A method according to any one of the preceding Statements, where the crosslinker(s) is/are chosen from polyethylene glycol dimethacrylate (PEGDMA), poly (ethylene glycol) diacrylate (PEGDA), four-arm PEG acrylate, divinyl sulfone (DVS), and the like, and combinations thereof.

Statement 6. A method according to Statement 1, where the crosslinker(s) is/are an oligomer or oligomers, a polymer or polymers, or a combination thereof comprising two functional groups that can react with the nucleotide polymers, such as, for example, DNA and/or RNA, of the biomass and a polymer comprising a plurality of oligomer and/or polymer groups and a plurality of nucleotide polymer, such as, for example, DNA and/or RNA, groups is formed.

Statement 7. A method according to Statement 6, where the oligomer crosslinker(s) and/or polymer crosslinker(s) is/are chosen from hydrocarbon oligomers, hydrocarbon polymers, and the like, and combinations thereof.

Statement 8. A method according to Statement 6 or 7, further comprising enzymatic treatment of the DNA and/or RNA biomass prior to reaction with the oligomer crosslinker(s) and/or polymer crosslinker(s) or after formation of the crosslinked nucleotide polymers, such as, for example, crosslinked DNA and/or RNA.

Statement 9. A method according to any one of the preceding claims, further comprising modifying at least a portion of or all of the nucleotide polymers, such as, for example, a DNA and/or RNA, of the biomass to form nucleotide polymers, such as, for example, a DNA and/or RNA, with one or more functional group(s) such that organic-soluble nucleotide polymers, such as, for example, a DNA and/or RNA, are formed.

Statement 10. A method according to Statement 9, where the biomass and crosslinker(s) are present in a mixture and the mixture comprises one or more organic solvent(s).

Statement 11. A method according to Statement 10, where the organic solvent(s) is/are chosen from alcohols (e.g., glycerol and the like), ionic liquids, formamide, and the like, and combinations thereof.

Statement 12. A method according to any one of the preceding Statement, where one or more additive(s) is/are added to the reaction mixture before the crosslinking reaction and/or to plurality of crosslinked DNA and/or RNA.

Statement 13. A method according to Statement 12, where the additive(s) is/are chosen from functional additives, inorganic materials (such as, for example, carbon materials (e.g., carbon nanotubes, such as, for example, single-wall carbon nanotubes, graphenes, graphene oxides), nanomaterials (such as, for example, cellulose nanocrystals, cellulose nanofibers, and the like), metal ions, clays, and the like, and combinations thereof), plasticizers (such as, for example, glycerol and the like), polymerizable monomers (which may be polymerized to form a conducting polymer), phosphorescent materials (such as, for example, rare earth compounds and the like), and the like, and combinations thereof.

Statement 14. A composition comprising one or more crosslinked nucleotide polymer(s), such as, for example, crosslinked DNA and/or RNA, and/or polymeric materials comprising nucleotide polymers, which may be crosslinked nucleotide polymer(s) (e.g., one or more composition(s) comprising a plurality of crosslinked nucleotide polymer(s), such as, for example, crosslinked DNA and/or RNA, and/or polymeric materials comprising nucleotide polymers, which may be crosslinked). A portion of or all of the one or more of the nucleotide polymer(s), such as, for example, crosslinked DNA and/or RNA, and/or polymeric materials comprising nucleotide polymers, which may be crosslinked (e.g., the one or more composition(s) comprising a plurality of nucleotide polymer(s), such as, for example, crosslinked DNA and/or RNA, and/or polymeric materials comprising nucleotide polymers, which may be crosslinked) may be made by a method of any one of Statements 1-13.

Statement 15. A composition according to Statement 14, the composition further comprising one or more solvent(s), one or more additive(s), or a combination thereof.

Statement 16. A composition according to Statement 14 or 15, where the composition is (or has one or more domains) that are amorphous, crystalline, or a combination thereof.

Statement 17. A composition according to any of Statements 14-16, where the composition is in the form of a film, a coating, a thread, a fiber (which may be a hollow fiber), a monolith, a three-dimensional structure, or the like, or a combination thereof.

Statement 18. A composition according to any of Statements 14-17, where the composition exhibits one or more or all of the following:
  desirable degredation and/or biodegradability
  desirable elastic modulus
  desirable glass transition temperature (Tg)
  desirable optical property(ies) (e.g., optical transparency and the like)
  surface property(ies) (e.g., adhesive, non-stick, and the like)

Statement 19. An article of manufacture comprising one or more crosslinked nucleotide polymer(s), such as, for example, crosslinked DNA and/or RNA, and/or one or more polymeric material(s), each polymeric material comprising nucleotide polymer groups, which may be crosslinked, and/or one or more composition(s) comprising one or more of crosslinked nucleotide polymer(s), such as, for example, crosslinked DNA and/or RNA, and/or one or more polymeric material(s), each material comprising nucleotide polymer groups, which may be crosslinked, (e.g., one or more composition(s) comprising a plurality of crosslinked nucleotide polymer(s), such as, for example, a plurality of crosslinked DNA and/or RNA, and/or one or more polymeric material(s) comprising nucleotide polymer groups, which may be crosslinked). A portion of or all of the one or more crosslinked nucleotide polymer(s), such as, for example, crosslinked DNA and/or RNA, and/or one or more polymeric material(s), each polymeric material comprising nucleotide polymer groups, which may be crosslinked, and/or one or more composition(s) comprising one or more of crosslinked nucleotide polymer(s), such as, for example, crosslinked DNA and/or RNA, and/or one or more polymeric material(s), each material comprising nucleotide polymer groups, which may be crosslinked, (e.g., one or more composition(s) comprising a plurality of crosslinked nucleotide polymer(s), such as, for example, a plurality of crosslinked DNA and/or RNA, and/or one or more polymeric material(s) comprising nucleotide polymer groups, which may be crosslinked) may be made by a method of any one of Statements 1-13.

Statement 20. An article of manufacture according to Statement 19, where the article of manufacture is chosen from textiles, toys, plastic bags, face masks, containers (e.g., cups and the like), utensils, medical articles, and the like, and combinations thereof.

Statement 21. A composition comprising a nucleotide hydrogel (e.g., a DNA and/or RNA hydrogel) (as described herein) further comprising a therapeutic agent (such, for example, insulin and the like), which may be soaked into the DNA/RNA hydrogel.

Statement 22. A method of treating an individual (which may be a controlled drug release method) comprising administering a therapeutic to a subject using the composition of Statement 21.

Statement 23. A method of coating a substrate (e.g., a wire or the like) with a crosslinked nucleotide polymer (e.g., a crosslinked DNA/RNA polymer).

The steps of the method described in the various examples disclosed herein are sufficient to carry out the methods of the present disclosure. Thus, in an example, a method consists essentially of a combination of the steps of the methods disclosed herein. In another example, a method consists of such steps.

The following examples are presented to illustrate the present disclosure. The examples are not intended to be limiting in any matter.

Example 1: Aza-Michael Addition Reactions of Biomass DNA

This example provides examples of the aza-Michael addition reactions of biomass DNA of the present disclosure and examples of methods of use for the aza-Michael addition reactions of the present disclosure.

Figures 11A, 11O:
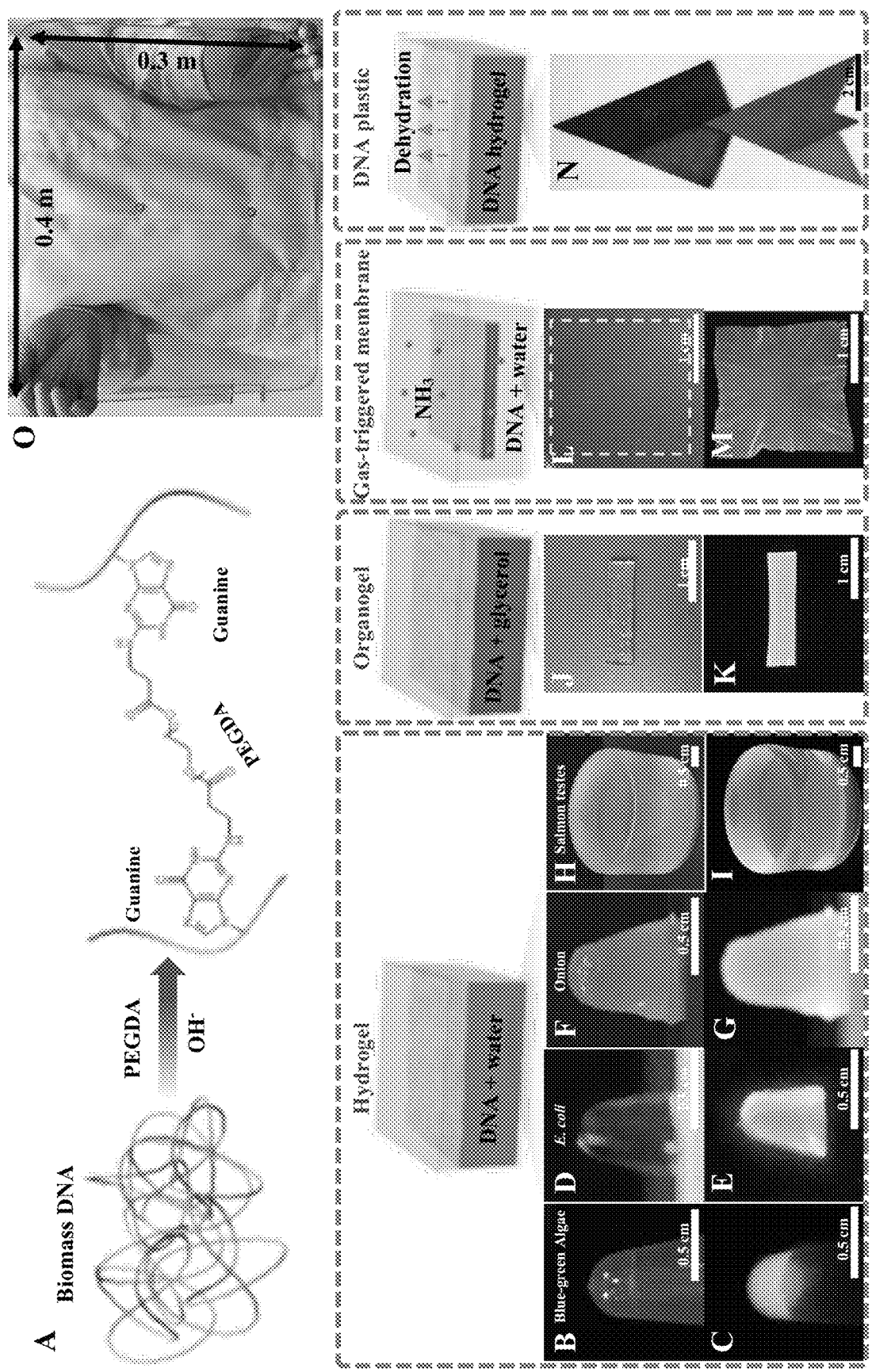
FIGS. 11A-11O show a mechanism of molecular crosslinking and preparations of biomass DNA materials. (A) Aza-Michael addition-based crosslinking of biomass DNA. (B to I) Biomass DNA hydrogels made from blue-green algae, E. coli, onion, and salmon testes. (Top) Photographs of DNA hydrogels; (Bottom) Fluorescence images of DNA hydrogels stained by DNA specific dyes: GelRed or SYBR Green I. (J and K) A photograph and an SYBR Green I-stained fluorescence image, respectively, of a biomass DNA organogel. (L and M) A photograph and a GelRed-stained fluorescence image, respectively, of biomass DNA membrane triggered by ammonia. (N) A photograph of T-puzzle toys made from biomass DNA materials. The colors were from food dyes. (O) A photograph of a meter scale biomass DNA hydrogel on a glass plate.

All biomass has DNA molecules consisting of four bases. With an approximately equal distribution, the four bases provide ample and diverse chemical groups for reactions. Specifically, the high nucleophilic activity of the 2-amine group of the guanine base (G) provides a convenient route for crosslinking DNA. In contrast to amine groups from A and C, the 2-amine group of G base of DNA has the highest nucleophilic activity, resulting in a desirable Michael addition between guanine of DNA and the α, β-unsaturated aldehydes acrolein, crotonaldehyde, and 4-hydroxy-2E-nonenal. By adding a Michael addition acceptor such as poly(ethylene glycol) diacrylate (PEGDA), it was considered that the amine group of G would attack carbon-carbon double bonds of acrylate of PEGDA to form nitrogen-carbon bonds based on the mechanism of aza-Michael addition, crosslinking the biomass DNA together (FIG. 11A).

Commercial salmon testes DNA was used as a model biomass DNA to react with PEGDA under alkaline catalysis.

Typically, biomass DNA was dissolved in deionized water with a gentle stirring. After adjusting the pH of the solution to 11 with alkali, PEGDA was added into the above solution. The biomass DNA was crosslinked, forming DNA hydrogels (FIGS. 11B-11I). In this strategy, the alkali serves not only as a catalyst for Michael addition but also as a denaturant of DNA double strands. There is no thermal denaturation required for this crosslinking. The reaction was simple (one step), mild (room temperature and atmosphere), green (atom-economic, no byproducts, and no waste), and highly efficient (in minutes).

Based on the aza-Michael reaction mechanism, three more kinds of biomass-DNA-based materials were prepared, including organogels, composite membranes, and plastics by simply adjusting the solvent or the crosslinking trigger (FIGS. 11J-11N). Noticeably, biomass DNA from almost all the domains of life were employed, including Bacteria and Eukaryota, spanning at least three of the six kingdoms including Eubacteria (blue-green algae, FIGS. 11B-11C, *E. coli*, FIGS. 11D-11E), Plantae (onion, FIGS. 11F-11G), and Animalia (salmon testes, FIGS. 11H-11I). Clearly, these diverse sources of biomass DNA surmounted the limitation of plant-only-based biomass and thus greatly facilitated the feasibility of future scaling up.

fabrication. DNA membranes were successfully fabricated by cross-linking the spin-coated biomass DNA solutions in an ammonia chamber (FIGS. 11L, 11M). The hydrogel membranes were transparent, flexible, and mechanically strong. Furthermore, by treating DNA as a polymer, the biomass DNA hydrogels of the present disclosure were readily converted to plastics simply by dehydrating and without any polymerization (FIG. 11N).

Figure 12:
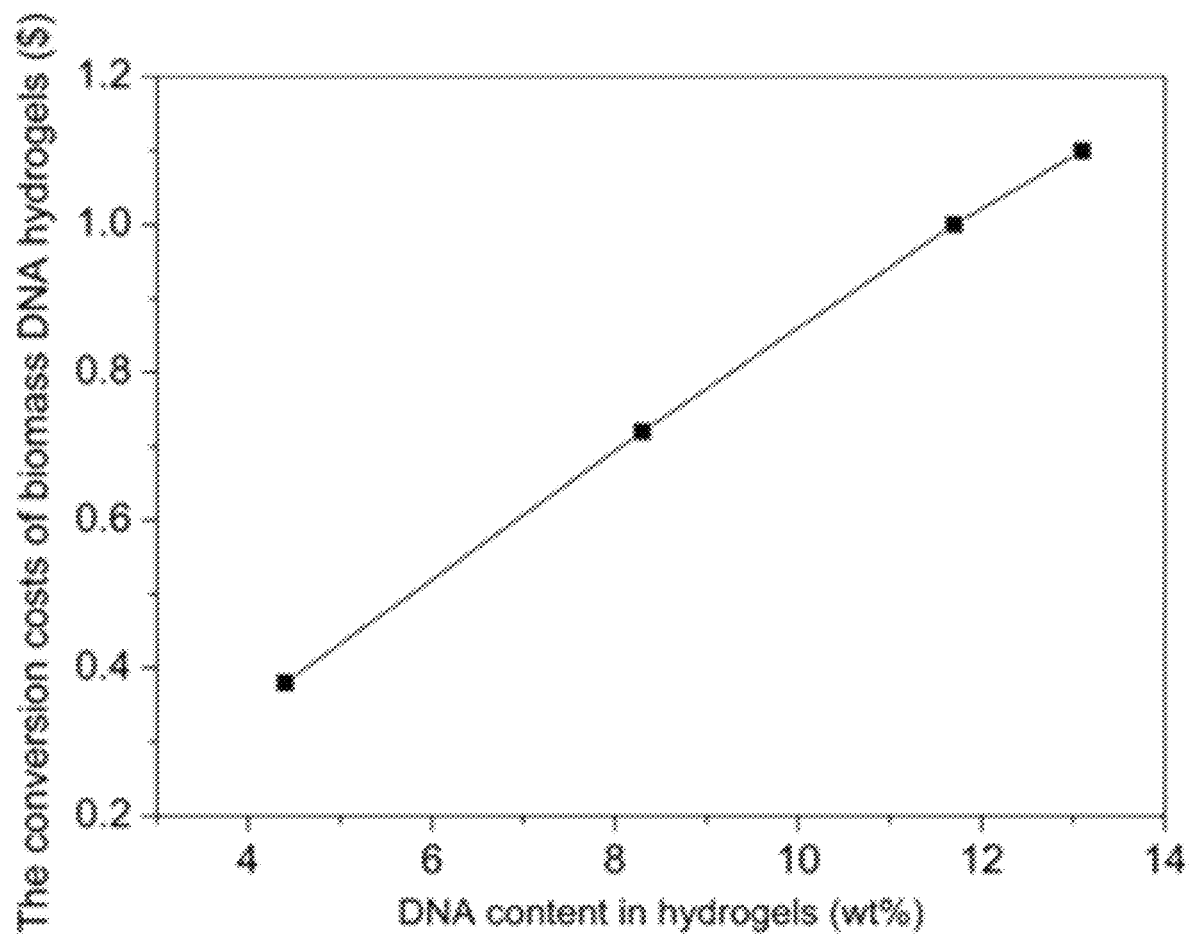
FIG. 12 shows the relation between conversion costs and DNA contents in hydrogels (the total mass of hydrogel was fixed at one gram). For hydrogels, the total cost was less than US one dollar per gram of DNA hydrogels explored by us. This figure was plotted according to the calculation from Table 1.

For any attempt to substitute or even replace petrochemicals with renewable sources, the strategy must consider the feasibility of large-scale production with an extremely low cost. Using biomass DNA combined with the simple approaches of the present disclosure, large scale preparation of biomass DNA hydrogels (on a glass plate) (FIG. 12O) and membranes at the meter scale was achieved. The cost was minimal due to the fact that our conversion was direct, requiring neither the breakdown of biomass molecules nor the polymeric synthesis. The entire conversion process cost less than US $1 per gram of DNA gel in the current lab setting (DNA extraction: less than $0.75; DNA crosslinking: less than $0.25) (FIG. 12 and Table 1). To the best of our knowledge, this was the least expensive DNA bulk material that had ever been made. It is expected that the cost would be dramatically reduced with in an industry setting.

TABLE 1

The cost calculation of biomass DNA hydrogels.

| Reagents | Recipe | Units | Price per Unit | Company | Price per 0.775 g DNA |
|---|---|---|---|---|---|
| Extraction: DNA from thymus, spleens, and Salmon testes | | | | | |
| calf thymus glands | 50.0 | g | — | food process waste | negligible price |
| sodium citrate | 67.6 | g | $0.004 | INGREDI.com | $0.27 |
| sodium chloride | 244.2 | g | $0.001 | INGREDI.com | $0.24 |
| ethanol | 6.5 | L | $0.920 | www.chembid.com/en | $5.98 |
| Duponol (sodium lauryl sulfate) | 11.0 | g | $0.002 | Bulk Apothecary | $0.02 |
| Conversion: | | | | | |
| PEGDA | 0.39 | mL | $0.218 | Sigma-Aldrich | $0.17 |
| Sodium Hydroxide | 0.041 | g | $0.183 | Fisher scientific | $0.008 |
| Total | | | | | $6.69# |

The cost calculation of extraction procedure was based on a previous reference and the product information of salmon testes DNA provided by Sigma-Aldrich. The reference showed that the extraction yield of DNA ranged from 600 to 950 mg. Here, the average yield of 775 mg was used for a cost calculation, the conversion cost was only US 18 cents, the total cost with extraction and conversion/gram of DNA was $8.63.

The novel, fundamental concept is the utilization of biomass DNA as a natural and renewable reactant for diverse products via a new and powerful crosslinking platform. The ultimate goal and also the broader impact of this disclosure is to pave the way for an alternative route towards reducing or even replacing petrochemical consumption. The well-established Michael addition-based crosslinking reaction enabled by PEGDA was utilized; the mechanism is well-known, and our reactions are green-compatible, versatile, and efficient. As shown in later examples, both hydrogels and organogels possessed diverse and attractive properties for real world applications. In the case of the catalytic trigger, ammonia was introduced as a gas trigger (in contrast to the sodium hydroxide, a solution-based trigger) to catalyze the aza-Michael addition reaction. This gas-triggered formulation was ideal to be employed for thin membrane Example 2: Biomass DNA Hydrogels This example provides examples of biomass DNA hydrogels of the present disclosure and examples of methods of making and characterization of hydrogels of the present disclosure.

Figures 13A, 13B:
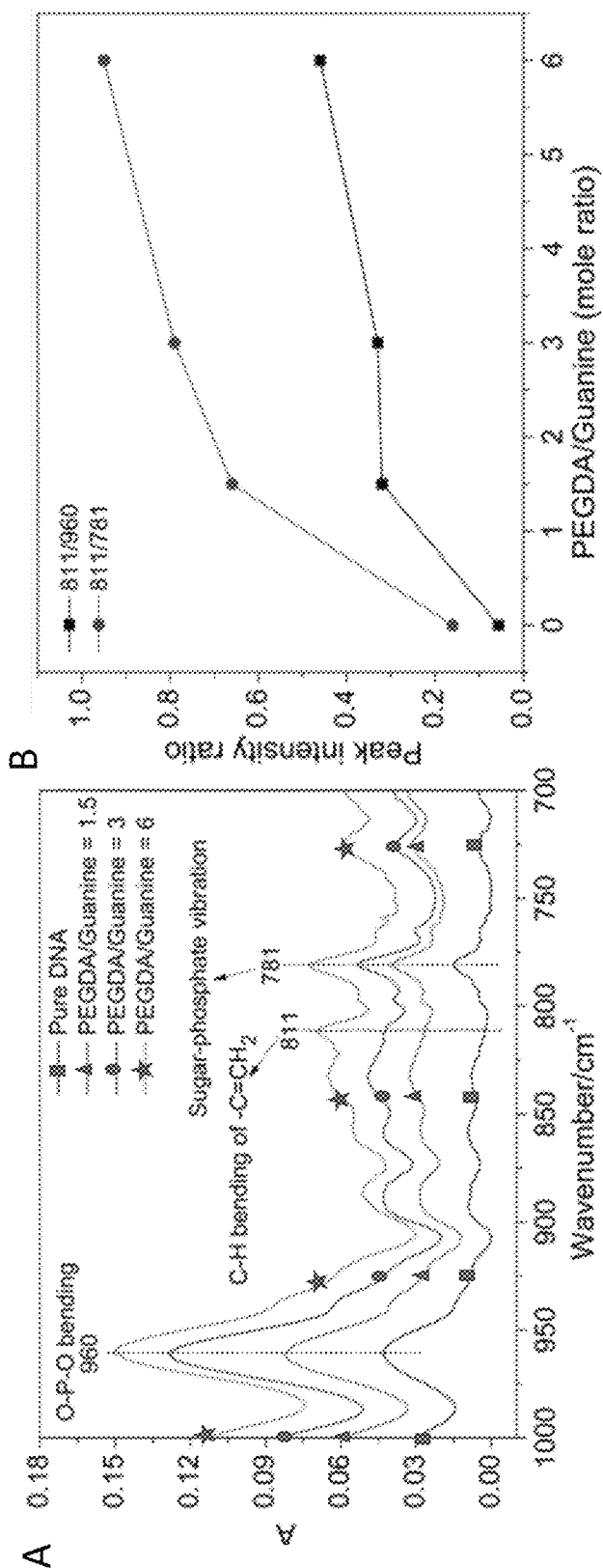
FIGS. 13A-13B show ATR-FTIR analysis of biomass DNA xerogels crosslinked by different amounts of crosslinker PEGDA. (A) The ATR-FTIR spectra of biomass DNA xerogels crosslinked by PEGDA. (B) The effect of the mole ratio of PEGDA/guanine on the intensity ratios of the peak at 811 cm' relative to the peaks at 960 and 780 cm'.

In this example, in order to confirm the cross-linking mechanism, the changes of the molecular structures in the gelation process were evaluated using Attenuated Total Reflection Fourier Transform Infrared (ATR-FTIR) spectroscopy (FIGS. 13A-13B, 14A-14B). For the characteristic peaks of salmon testes DNA at 781 and 960 cm$^{-1}$ (attributed to sugar-phosphate vibration and O—P—O bending vibration, respectively), there were no conspicuous changes between the pure salmon testes DNA and crosslinked xerogels, indicating that the formation of a new C—N bond without altering the overall DNA structure (FIG. 13A). These two DNA peaks served as internal references to calculate the peak intensity ratio since they did not participate in cross-linking reaction. With increasing mole ratio of PEGDA/guanine, the peak at 811 cm$^{-1}$ assigned to C—H bending vibration of —C=CH$_2$ of PEGDA intensified gradually, and the intensity ratios relative to DNA peak at 960 and 781 cm-1 also increased (FIG. 13B), suggesting that PEGDA formed covalent bonds with DNA.

Figures 14A, 14B:
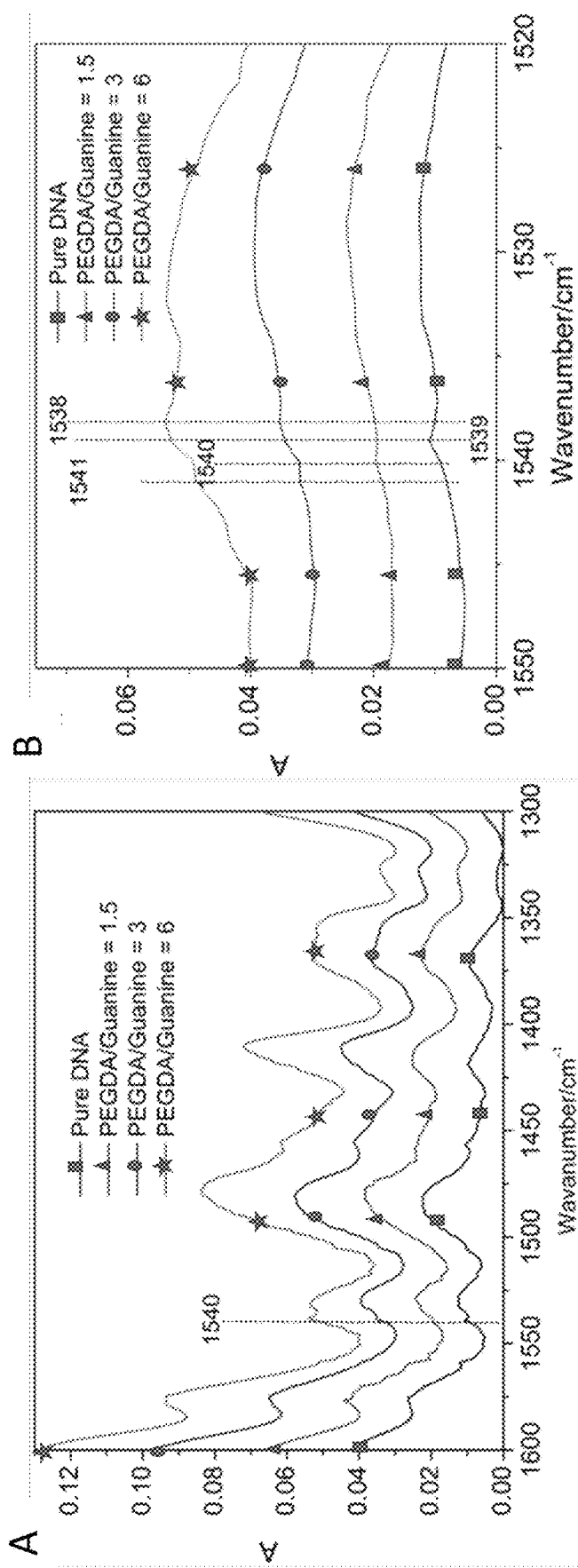
FIGS. 14A-14B show ATR-FTIR analysis of C—N bond in biomass DNA xerogels crosslinked by different amounts of crosslinker PEGDA. (A) The peak at 1540 $cm^{-1}$ is attributed to the C—N bond of aza-Michael addition. (B) The peak at 1539 $cm^{-1}$ is assigned to the bases of DNA at low mole ratio of PEGDA/guanine and broadens and splits into two peaks (1541 and 1538 $cm^{-1}$) with increasing mole ratio of PEGDA/guanine.

The peak at 1540 cm-1 was attributed to the C—N bond due to aza-Michael addition (FIG. 14A). Though this peak overlapped with the peak at 1539 cm$^{-1}$ assigned to the bases of DNA, the DNA peak broadened and split into two peaks (1541 and 1538 cm$^{-1}$) with increasing mole ratio of PEGDA/guanine (FIG. 14B), providing evidence for the occurrence of covalent bonds formed between PEGDA and biomass DNA, resulting in crosslinked hydrogels. This variation demonstrated that new C—N bonds formed in hydrogel, supporting the cross-linking mechanism based on the aza-Michael addition.

Figure 15:
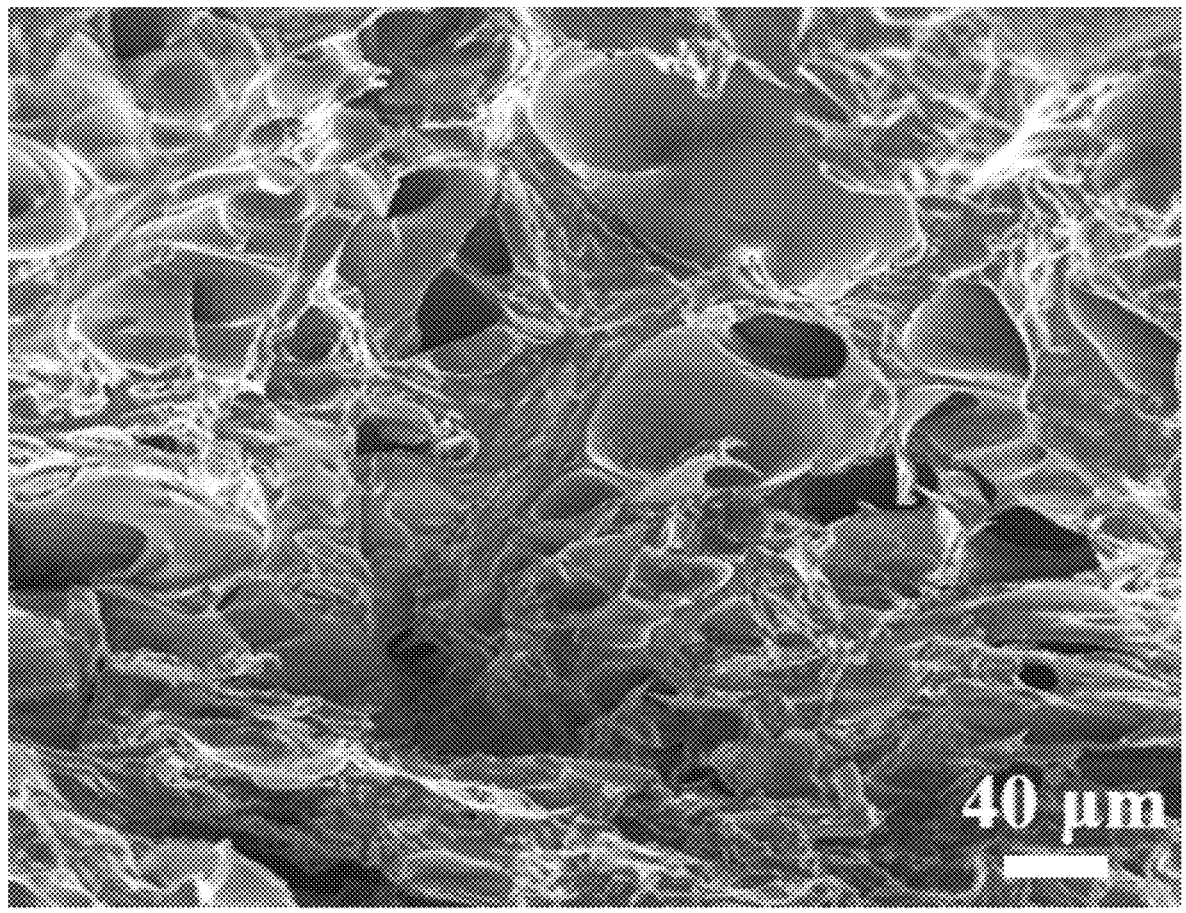
FIG. 15 shows an SEM image of 8.3% DNA hydrogel.
Figures 16A, 16B, 16C:
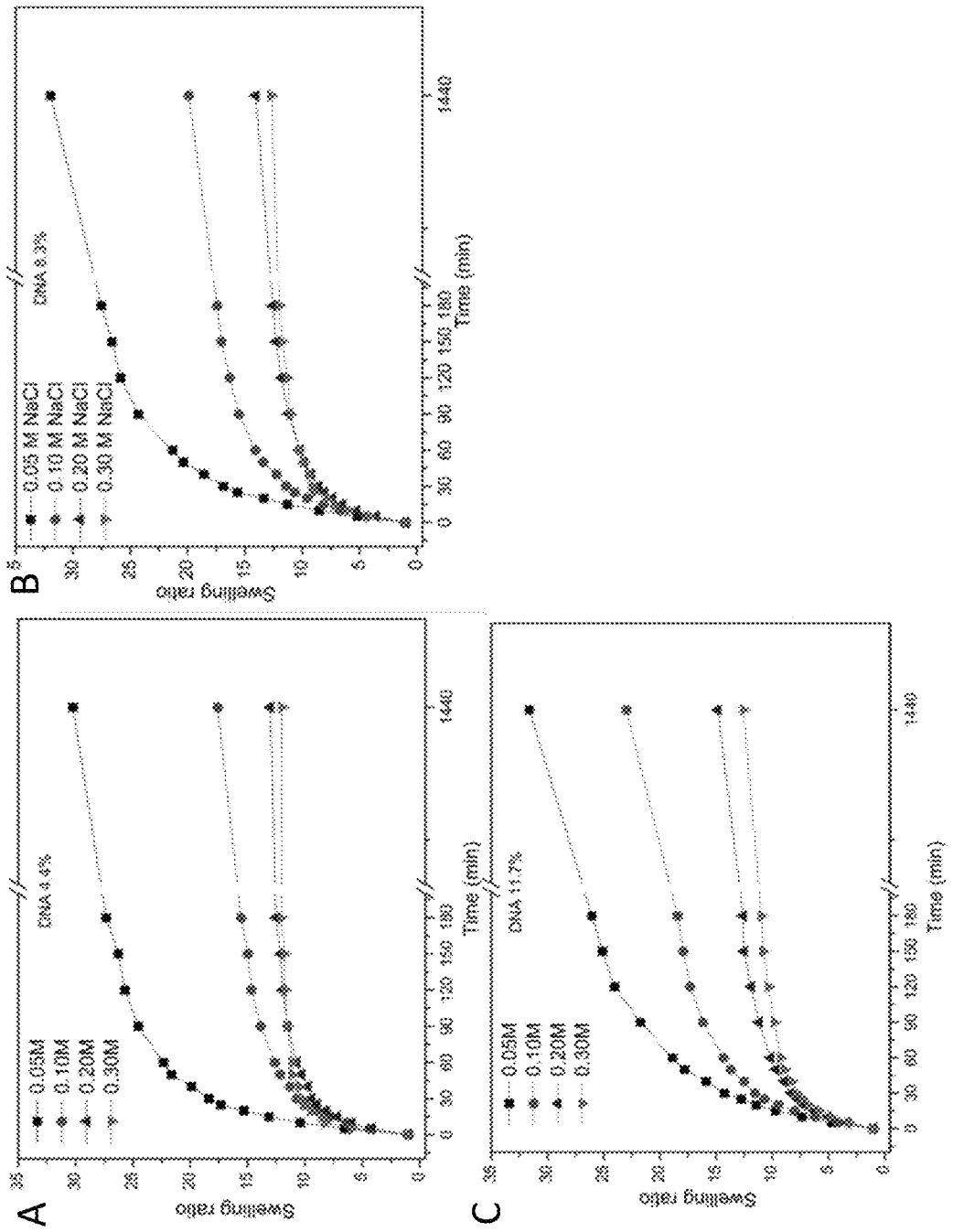
FIGS. 16A-16C show swelling profiles of DNA hydrogels containing (A) 4.3%, (B) 8.3%, and (C) 11.7% DNA in electrolyte solution with different concentration of NaCl. Swelling profiles of biomass DNA hydrogels were obtained by putting lyophilized hydrogels into sodium chloride solution in different concentration (around the physiological ionic strength) and weighing the weight changes.
Figures 17A, 17B:
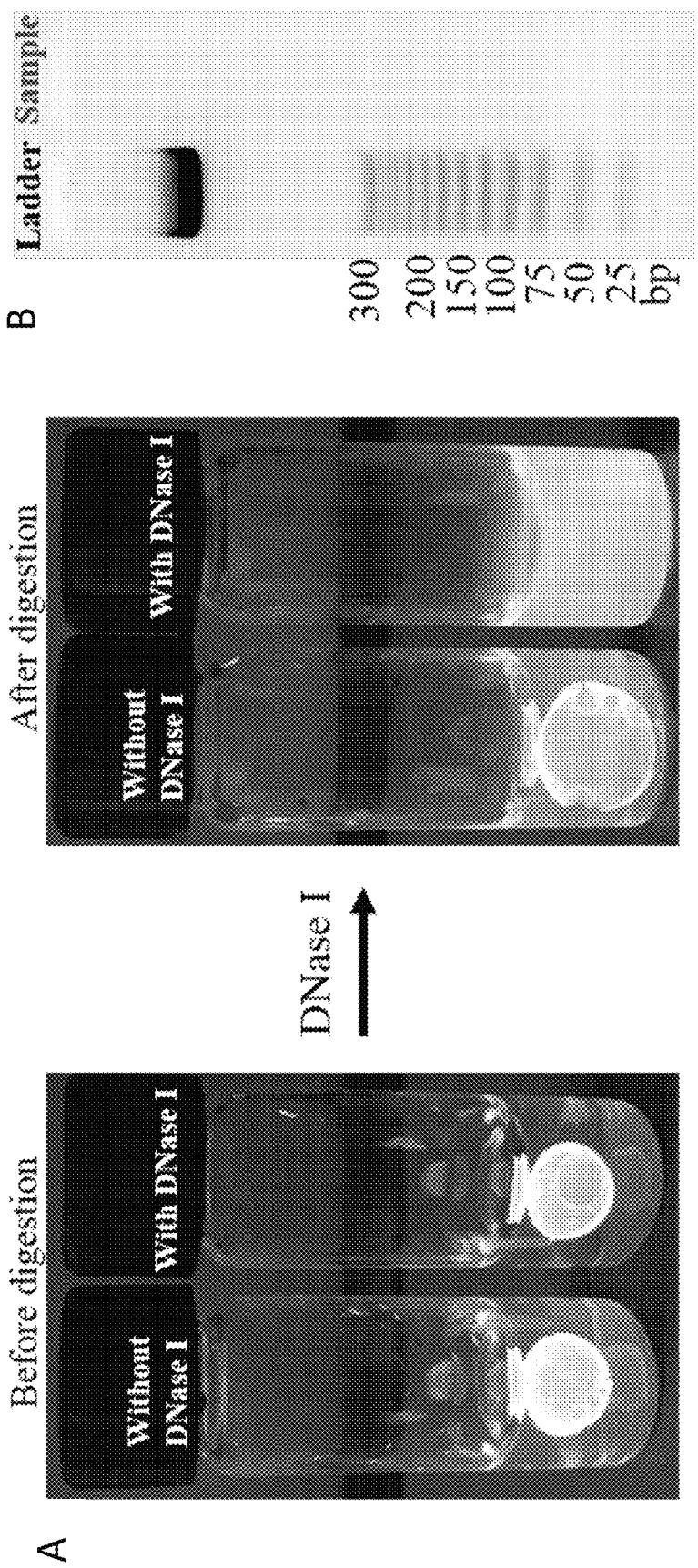
FIGS. 17A-17B show DNase I digestion of a biomass DNA hydrogel. (A) Photographs of biomass DNA hydrogels before and after digestion. (B) Gel electrophoresis characterization of the DNase I digestion.

The structural morphologies of biomass DNA hydrogels were characterized using scanning electronic microscopy (SEM) which showed typical micrometer-sized pores (average size, about 20 µm) (FIG. 15). The swelling ratios of the DNA hydrogels were also evaluated. The swelling ratios were dependent on the ionic strengths of the solutions (FIGS. 16A-16C): the higher the electrolyte concentration, the lower swelling ratio. The swelling ratio reached a plateau after about one hour. To confirm the degradability of our biomass DNA materials, biomass DNA hydrogel was incubated with a DNA digesting enzyme, DNase I under very mild conditions (37° C., neutral pH). Digestion completely dissolved the hydrogel, stained by GelRed (FIG. 17A) and degraded the hydrogel into oligonucleotides, as confirmed by gel electrophoresis (FIG. 17B).

Figures 18A, 18B, 18C:
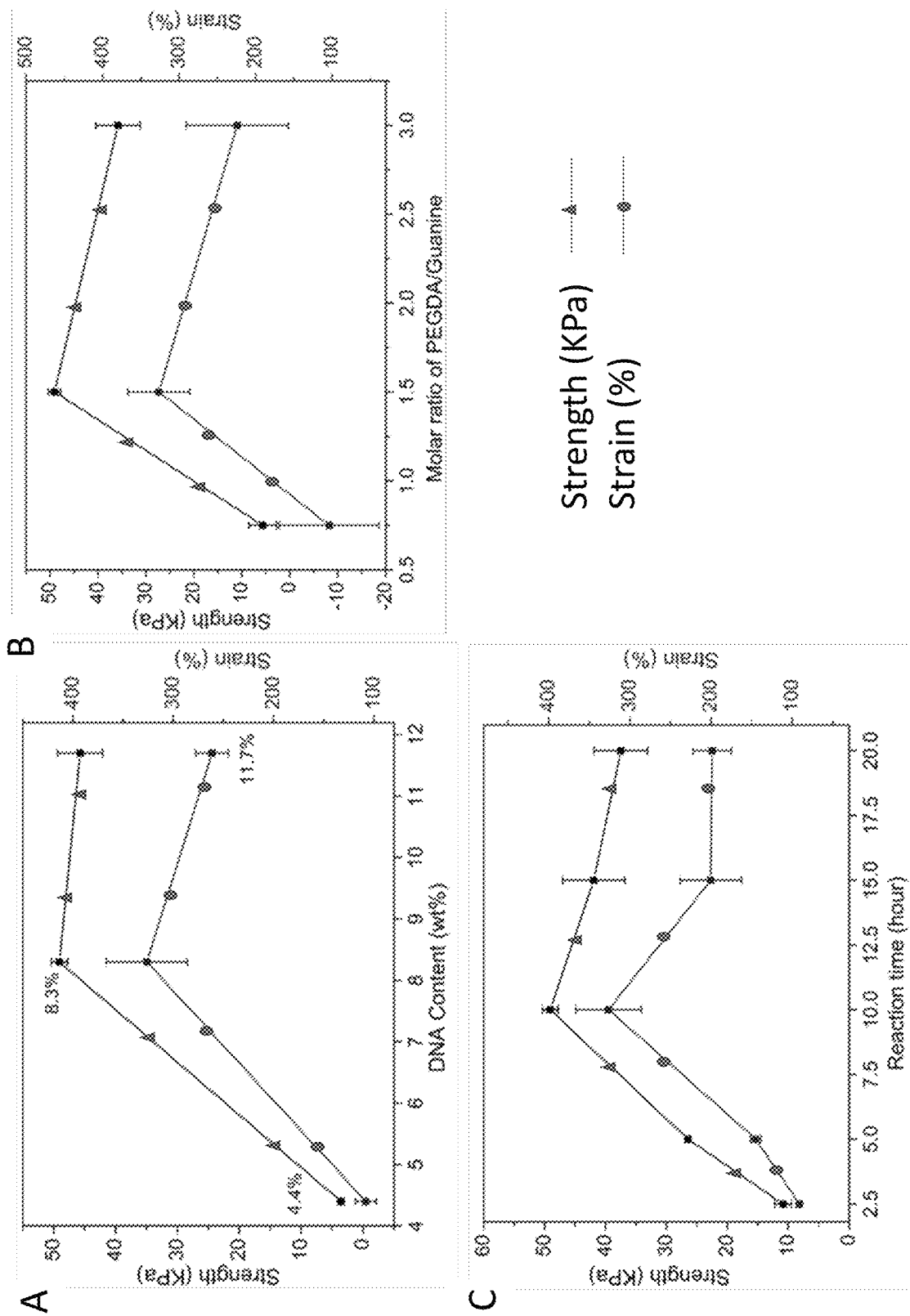
FIGS. 18A-18C show mechanical strength variation of DNA hydrogels with different reaction conditions. (A) Effect of DNA content on the strength and strain of hydrogels. (B) Effect of the molar ratio of PEGDA/guanine on the strength and strain of hydrogels. (C) Effect of the reaction time on the strength and strain of hydrogels. Error bars represent the standard deviation of 3 measurements.

The mechanical properties of biomass DNA hydrogels were regulated by altering the reaction conditions including the weight percentage of DNA and the reaction time (Table 2 and FIGS. 18A-18C).

TABLE 2

The effect of NaOH dosage on gelation (DNA was dissolved in 100 µL water, molar ratio of PEGDA/guanine is 1.5).

| | DNA 11.7% | | | DNA 8.3% | | | DNA 4.4% | |
|---|---|---|---|---|---|---|---|---|
| NaOH (µL) | start time(min) | setting time | NaOH (µL) | Start time(min) | setting time | NaOH (µL) | start time(min) | Setting time |
| 1 | fragile | fragile | 1 | 16 | 33 | 1 | 18 | 38 |
| 2.5 | 15 | fragile | 2.5 | 10 | 23 | 2.5 | 17 | 26 |
| 5 | 8 | 17 | 5 | 9 | 18 | 5 | 21 | 29 |
| 10 | 16 | 22 | 10 | 20 | 29 | 10 | 78 | 99 |

This table shows preliminary control experiments for optimizing preparation conditions of tough hydrogel. Start time means that the reaction solution was starting to harden at that time, and setting time means that the reaction solution became a gel that can be taken out from the mold and capable of keeping the shape at that time. Fragile means that the gel is easily fragmented and hardly keep an intact shape. With increasing the percentage of DNA, the gelation time decreased. Both higher and lower pH are not beneficial to the gelation. The mole ratio of PEGDA/guanine was calculated from the following equation:

$$\text{Mole ratio of } PEGDA/\text{guanine} = \frac{650 \times m_{PEGDA}}{m_{DNA} \times M_{PEGDA} \times 41.2\%}$$

where 650 is the average molecular weight of a base pair of DNA, m$_{PEGDA}$ is the mass of PEGDA used in experiment, m$_{DNA}$ is the mass of DNA used in experiment, m$_{PEGDA}$ is the molecular weight of PEGDA.

By fixing the ratio of water/NaOH solution (100 μL:5 μL) and the molar ratio of PEGDA/guanine (1.5), the hydrogel containing 8.3% DNA showed the best mechanical strength (FIG. 18A). By fixing the ratio of water/NaOH solution (100 μL:5 μL) and the percentage of DNA (8.3%), the best molar ratio of PEGDA/guanine was 1.5 (FIG. 18B). After the usages of DNA, NaOH, and PEGDA were optimized, for the best mechanical property, the reaction time was 10 h (FIG. 18C).

Figures 19A, 19B, 19C, 19D, 19E, 19F, 19G, 19H, 19I, 19J:
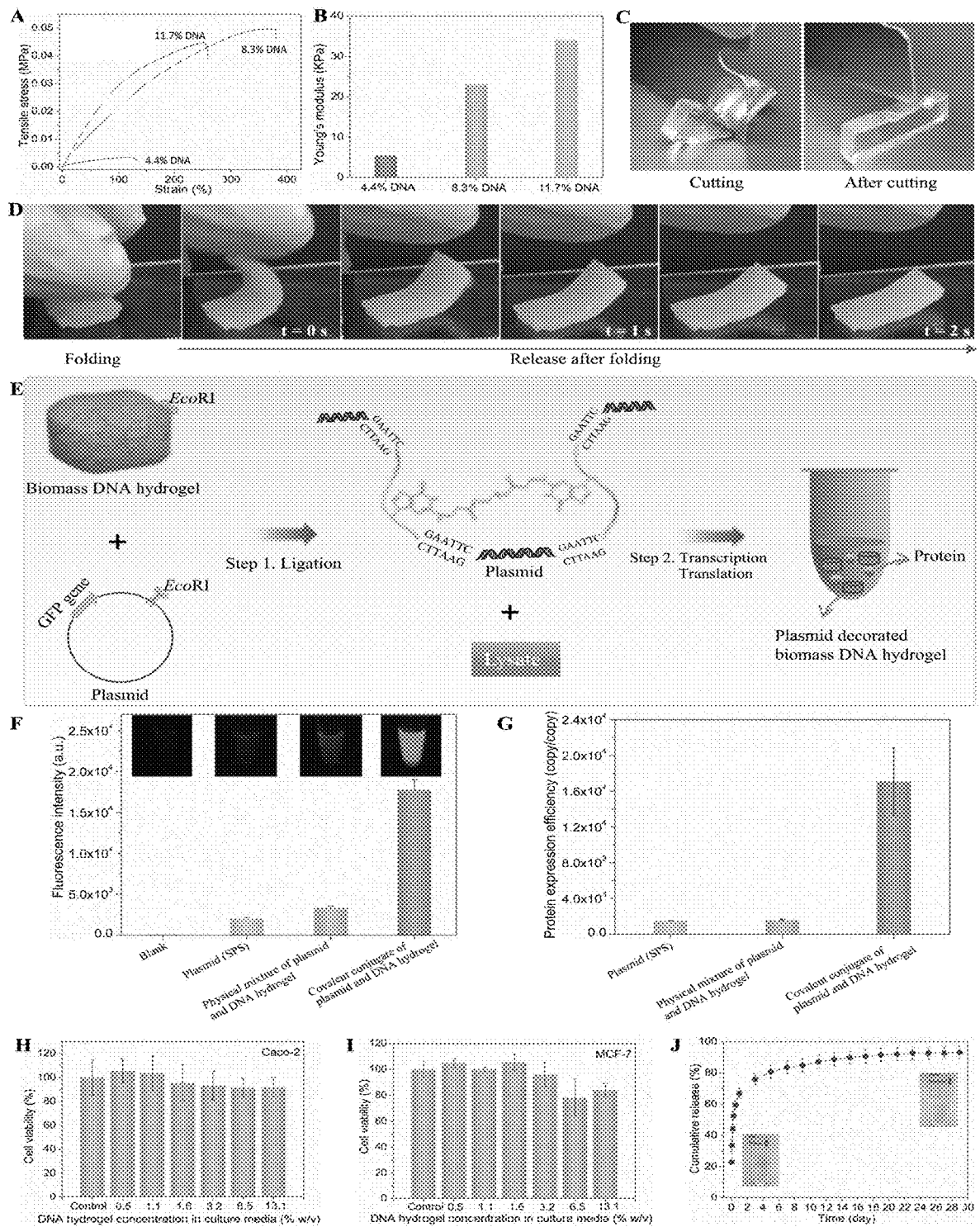
FIGS. 19A-19J show mechanical properties and biofunctions of biomass DNA hydrogels. Stress-strain curves (A) and young's moduli (B) of biomass DNA hydrogels with different DNA contents. (C) Photographs of a hydrogel (with 8.3% biomass DNA) being cut by a razor blade. (D) A series of video screen shots of a rubber-like biomass DNA hydrogel showed a quick and reversible shape recovery. (E) Preparation and protein expression processes of biomass DNA hydrogel for cell-free protein production. Comparison of fluorescence intensities and images (insets) (F) and comparison of expression efficiencies (G) of GFP expressed between the biomass DNA hydrogel and the control samples. (H and I) Cytotoxicity assessment of biomass DNA hydrogels on two cell lines: Caco-2 and MCF-7, respectively. (J) Cumulative controlled release profiles of insulin in biomass DNA hydrogels. Error bars represent the standard deviation of 3 measurements.
Figure 20A:
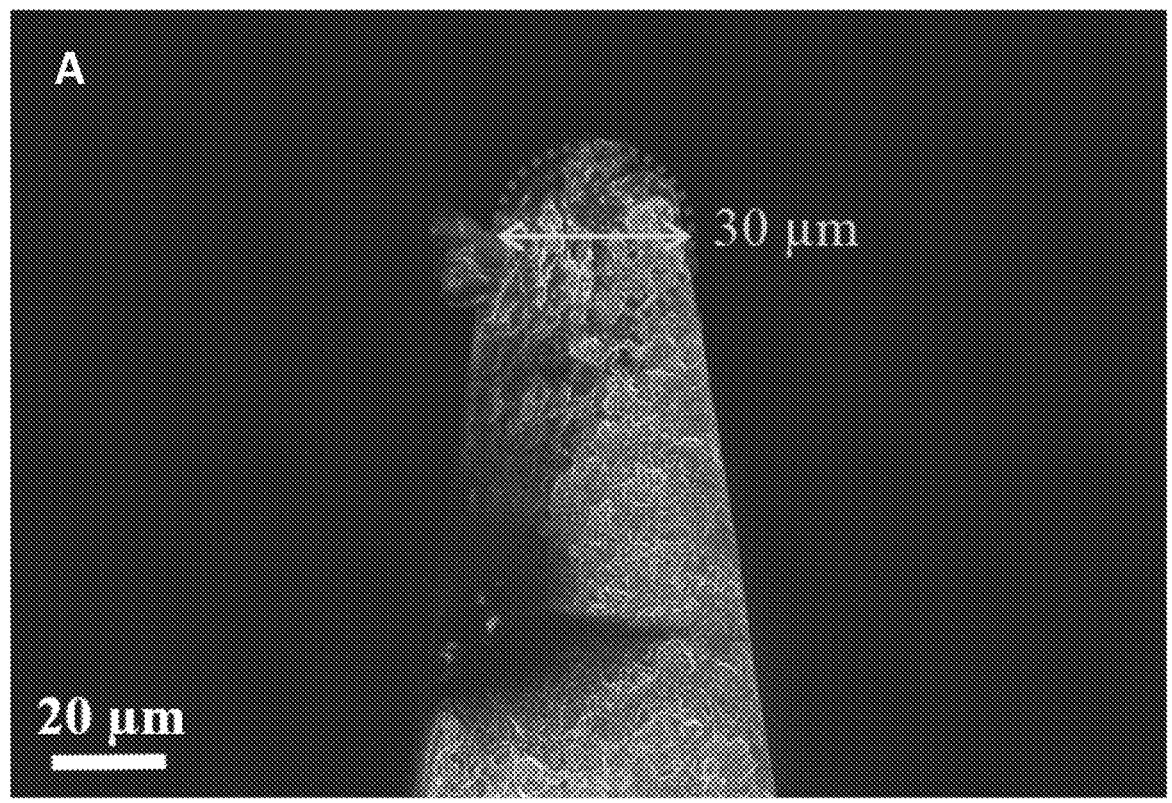
FIGS. 20A-20B shows shear modulus calculation of a biomass DNA hydrogel during blade cutting. (A) An SEM of Razor blade edge. (B) The parameters of the blade cutting process.
Figure 20B:
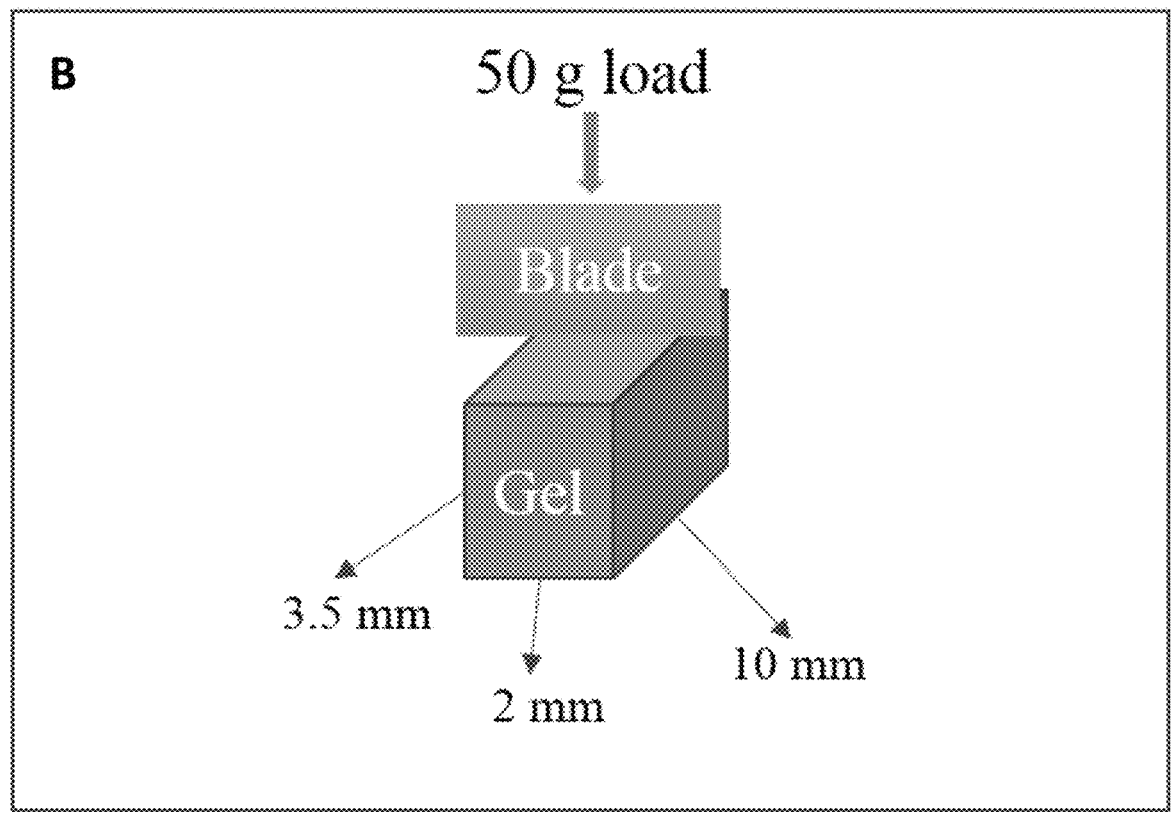

The mechanical strength increased 10 times by increasing both the DNA percentage and reaction time (FIG. 19A), and so were the strains and the Young's moduli (FIG. 19B). These results indicated that the increase of the DNA concentration and/or the crosslinking degree enhanced the mechanical properties (strength and young's modulus). Consequently, we fabricated both tough and elastic biomass DNA hydrogels that resisted knife cutting (FIG. 19C, FIG. 20). For determining shear modulus during the blade cutting procedure (FIG. 20): the maximum loading mass was 50 g and the shear stress$_{max}$ was calculated as follow:

$$\text{Shear stress}_{max} = \frac{\text{loading force}}{\text{contact area}} = \frac{50 \text{ g} \times 9.8 \text{ N/kg}}{\frac{3.14 \times 30}{2} \times 10^{-6} \text{ m} \times 0.002 \text{ m}} = 5.2 \text{ MPa}$$

The shear modulus was calculated as follow:

$$\text{Shear modulus} = \frac{\text{Shear stress}_{max}}{\text{strain}} = \frac{5.2 \text{ MPa}}{\frac{10 \text{ mm}}{10 \text{ mm}}} = 5.2 \text{ MPa}$$

Biomass DNA hydrogels also behaved like elastomers, similar to polyisoprene (rubber), by simply increasing the DNA concentration and the crosslinking degree (FIG. 19D).

One of the most appealing and unique properties of DNA is that it is the molecule of life, possessing a genetic coding capability not found in any other known material. To explore the protein production potential of our DNA converted material, biomass DNA hydrogel were prepared as elaborated earlier. Since the biomass DNA in the hydrogel was intact, it remained an active substrate of DNA processing enzymes including restriction endonucleases and ligases. On the base of positive result of the DNase I digestion, the EcoRI digestion of salmon testes DNA was conducted. Gel electrophoresis showed that the band intensity at high molecular weight region of salmon testes DNA declined with EcoRI digestion, which revealed that salmon testes DNA had a positive responsiveness to EcoRI, providing a prerequisite for plasmid incorporation of hydrogel (FIG. 21).

Figure 21:
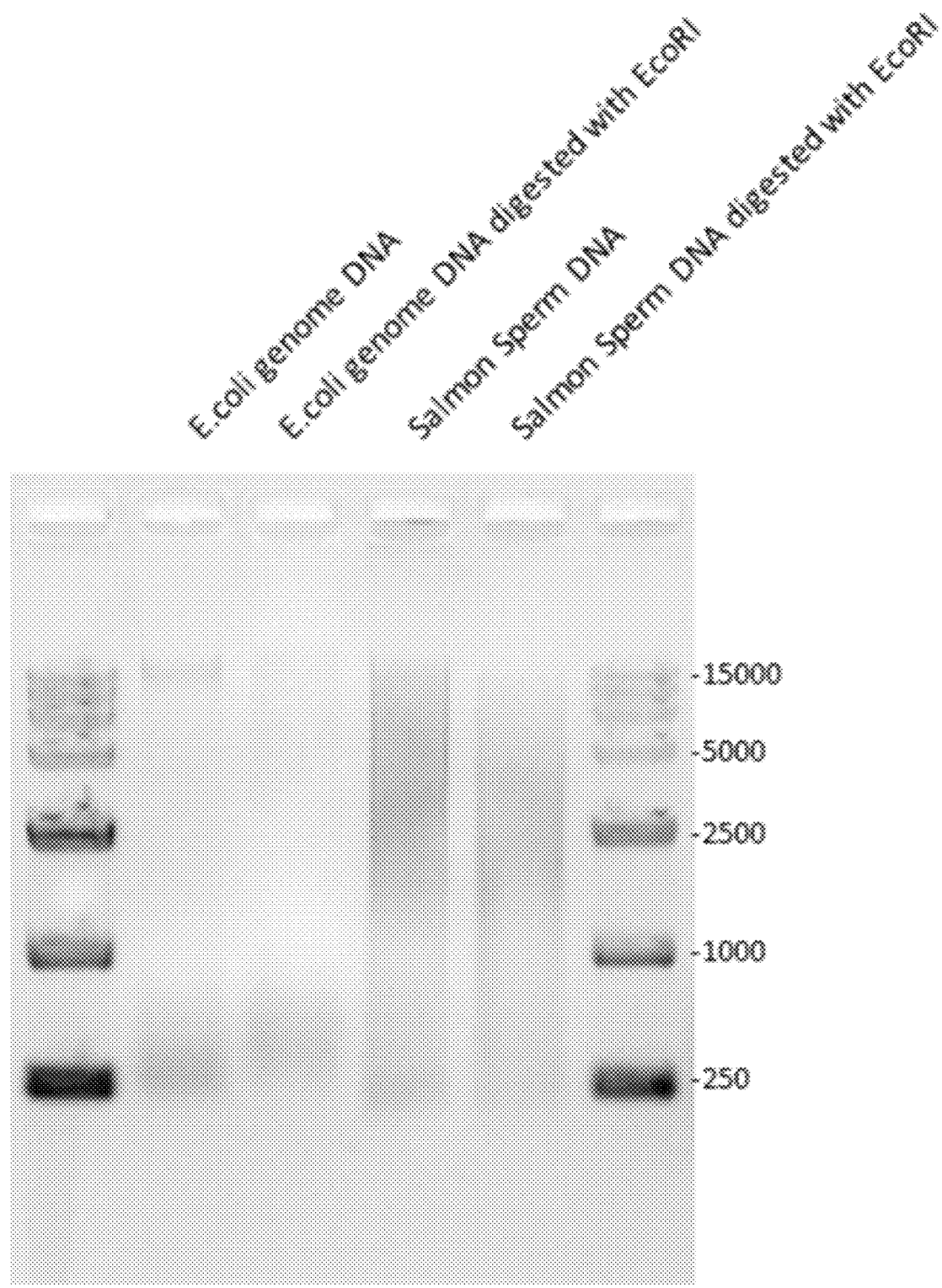
FIG. 21 shows the EcoRI digestion of salmon testes DNA.
Figure 22:
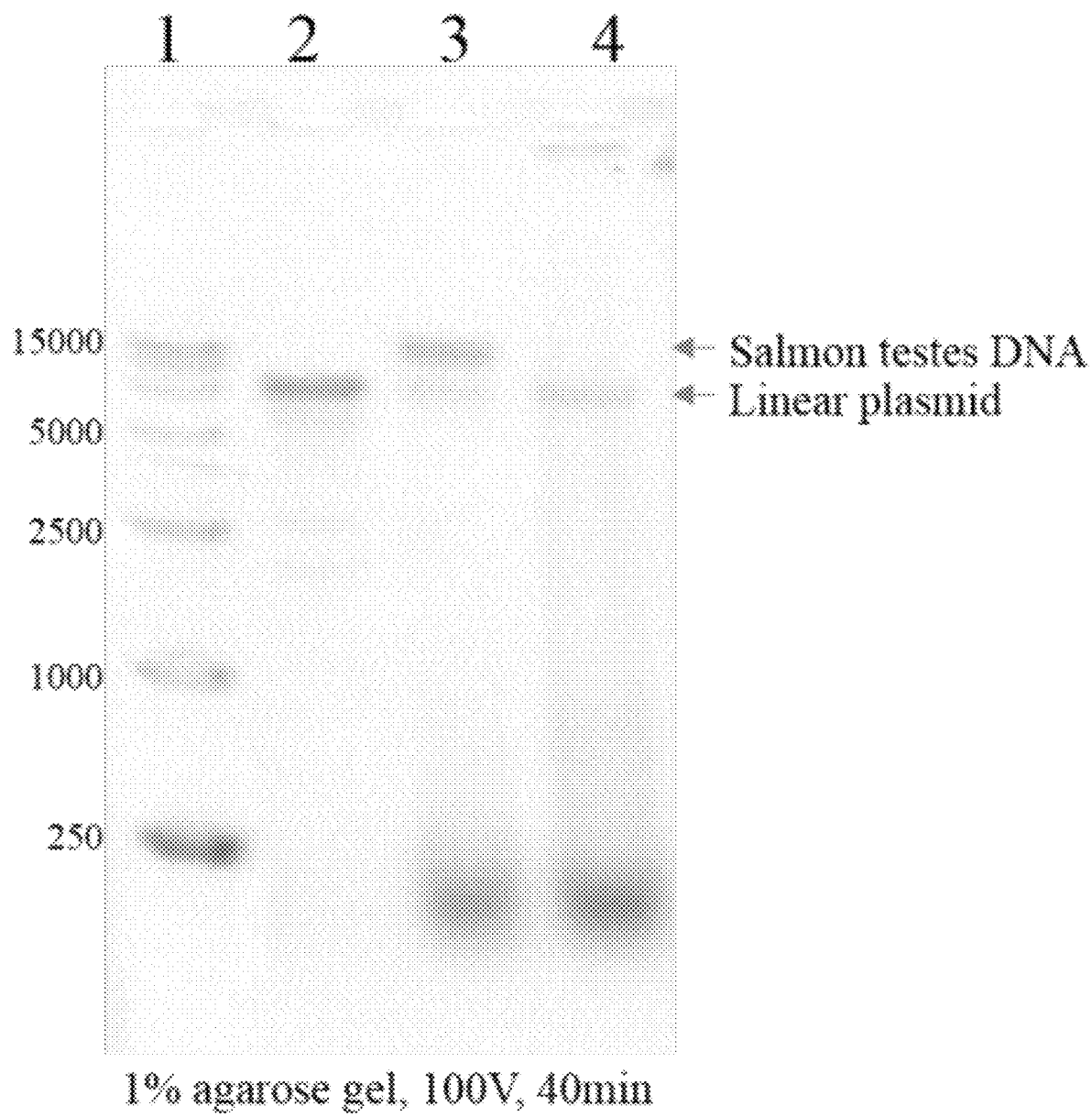
FIG. 22 shows the EcoRI digestion of DNA hydrogel and incorporation of plasmid by T4 ligase. Lane 1: 15,000 bp ladder. Lane 2: EcoRI digested pIJ8660T7 wt-GFP (linear plasmid, 1 μg). Lane 3: Supernatant of T4 ligated EcoRI digested Salmon testes DNA gel and linear plasmid. Lane 4: Supernatant of EcoRI digested Salmon testes DNA gel and linear plasmid mixture.

Both biomass DNA hydrogel and plasmid DNA (coding for Green Fluorescent Protein, GFP) were digested with EcoRI, so that palindromic sticky ends (-5'GAATTC3'-) were generated on both types of DNA (FIGS. 21-22). The GFP-encoding plasmid DNA was then ligated into the matrix of biomass DNA hydrogel by virtue of complementary base pairing (FIG. 19E, step 1). The rate of plasmid ligated to the biomass DNA hydrogel (8.3%) was calculated according to gel electrophoresis band intensity (FIG. 22). Generally, 200 ng/μL EcoRI digested linear pIJ8660T7 wt-GFP plasmid and 6 μg/μL EcoRI digested salmon testes DNA gel (same mass ratio as in cell-free protein synthesis) were ligated with 10 U/μL T4 ligase for 3 h at room temperature (free plasmid in this reaction was assigned as Pos.). A null T4 ligase reaction was run at the same time as a calibration control for gel electrophoresis (free plasmid in this reaction was assigned as Cal.). Centrifuge at 12,000×g for 5 min, 5 μL supernatant of each reaction was used to run gel electrophoresis with 1 μg linear plasmid as control (Ctrl). The intensity (I) of linear plasmid bands were measured with software Image J and the ligation rate was calculated as follows:

Ligation rate=$((I_{Ctrl}-I_{Pos})-(I_{Ctrl}-I_{Cal}))/I_{Ctrl}$=16.6%

(15130.430−653.991)/15130.430=95.6%

(15130.430−3179.296)/15130.430=79.0%.

Furthermore, the mole ratio of plasmid/biomass DNA in this hydrogel was calculated. The mass ratio of plasmid/biomass DNA was 1:30. The molecular weights of plasmid and biomass DNA were 8051 bp and 2000 bp, respectively. Taking the ligation rate of plasmid into account, a mole ratio of plasmid/biomass DNA was as follow:

$$\frac{\frac{1 \times 0.166}{8051 \times 650}}{\frac{30}{2000 \times 650}} \approx 0.001$$

To assess the protein productivity, standard cell-free protein expression assays were performed (FIG. 19E, step 2). Results revealed that not only was the functional GFP produced by the biomass DNA hydrogel, but also the production yield (total GFP) was 9 times higher than that of the control sample (commercial solution phase system, SPS) and 5 times higher than that of the physically mixing the plasmid with the DNA hydrogel (FIG. 19F). This much higher level of total protein production was attributed to the greater stability of the plasmid, the faster kinetics, and more confinement of the hydrogel, similar to what we had reported previously with a non-biomass DNA hydrogel. By further analyzing the protein production efficiencies using the number of protein produced per gene, it was estimated that the biomass DNA hydrogel produced $1.7 \times 10^4$ copies of proteins per copy of the gene; this was 11 times higher than that of both controls (SPS and the physical mixture) (FIG. 19G). In terms of how many copies of plasmid DNA needed, surprisingly, it was found that only one copy of GFP-DNA was needed per 1000 copies of biomass DNA in the aforementioned tests (FIG. 22). In contrast to the previously reported, sequence synthesis-based DNA hydrogel system, with so few copies of genes and with such a low cost of biomass DNA hydrogel, the presently disclosed biomass DNA-based system provided an unprecedented route to realize large-scale protein manufacturing in the near future.

Much biomass DNA such as that found in fruits and vegetables (e.g., onion as shown in FIGS. 11F-11G) is consumed uncooked as food and thus are presumably highly biocompatible and physiologically digestible. In addition, the crosslinker, PEGDA, has been used in many food and drug administration (FDA)-approved applications owing to its non-immunogenic and biocompatible features. Cytotoxicity assays supported the biocompatibility of DNA hydrogels (FIGS. 19I1-19I1). Consequently, the biomass DNA hydrogel would be an ideal biocompatible and biodegradable reservoir for sustained drug delivery. Indeed, post-loaded protein drug (insulin) was totally released in a controlled fashion over 30 days (FIG. 19J). The cumulative release behavior of insulin was similar to most other hydrogels displaying a two-phase release profile: a burst release first followed by a steady, controlled release. The majority of the encapsulated insulin was released within three weeks.

Example 3: Biomass DNA Organogels

This example provides examples of biomass DNA organogels of the present disclosure and examples of methods of making and characterization of DNA organogels of the present disclosure.

Figure 23:
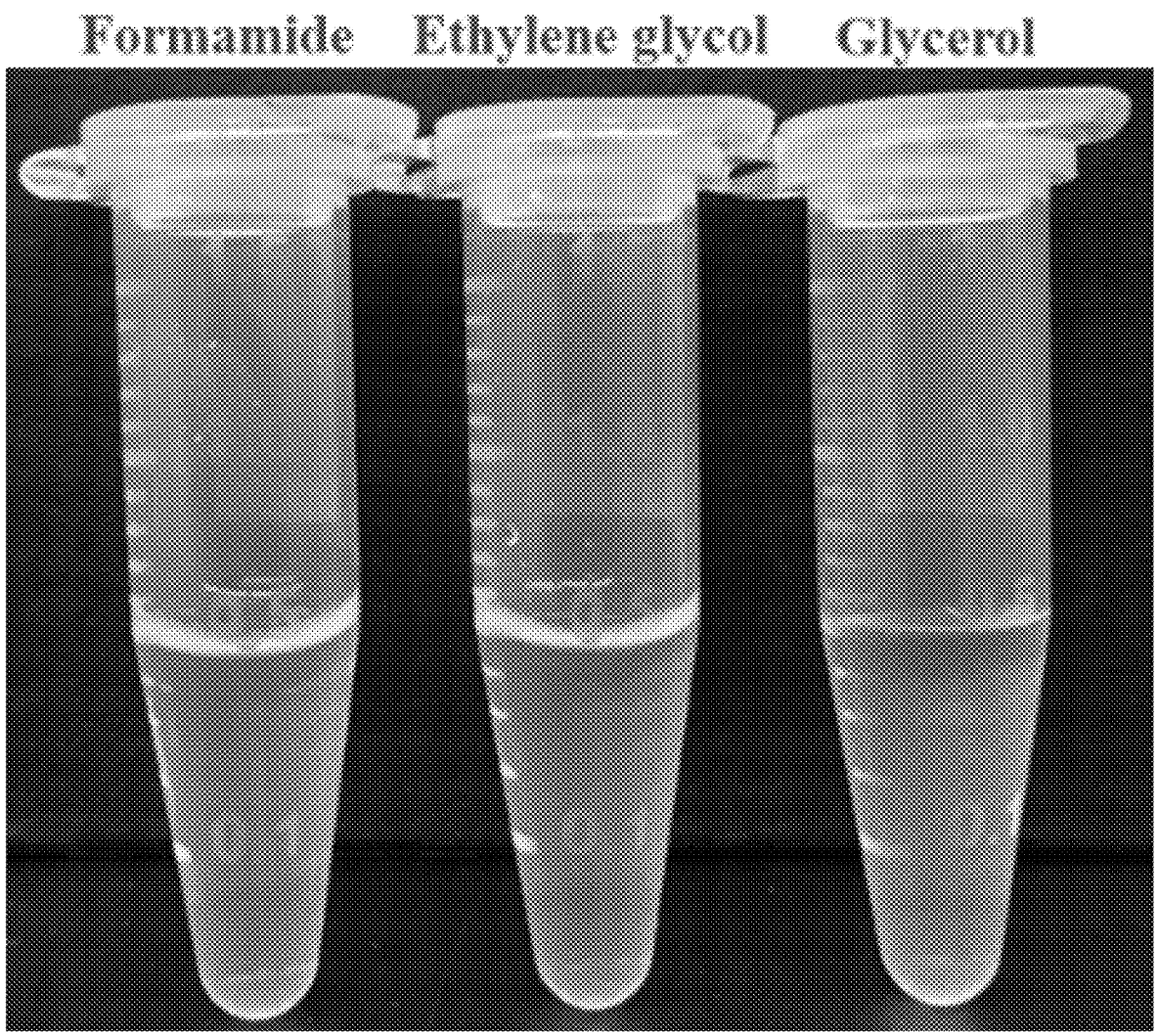
FIG. 23 shows a photograph of biomass DNA formamide, ethylene glycol, and glycerol solutions (the concentrations were 20 mg/mL).

In addition to hydrogel, organogel is becoming another appealing soft material. However, the fact that DNA is highly hydrophilic and polar with extremely high charge density reduces the number of organic solvents capable of dissolving DNA (FIG. 23).

Figures 24A, 24B, 24C, 24D, 24E, 24F, 24G:
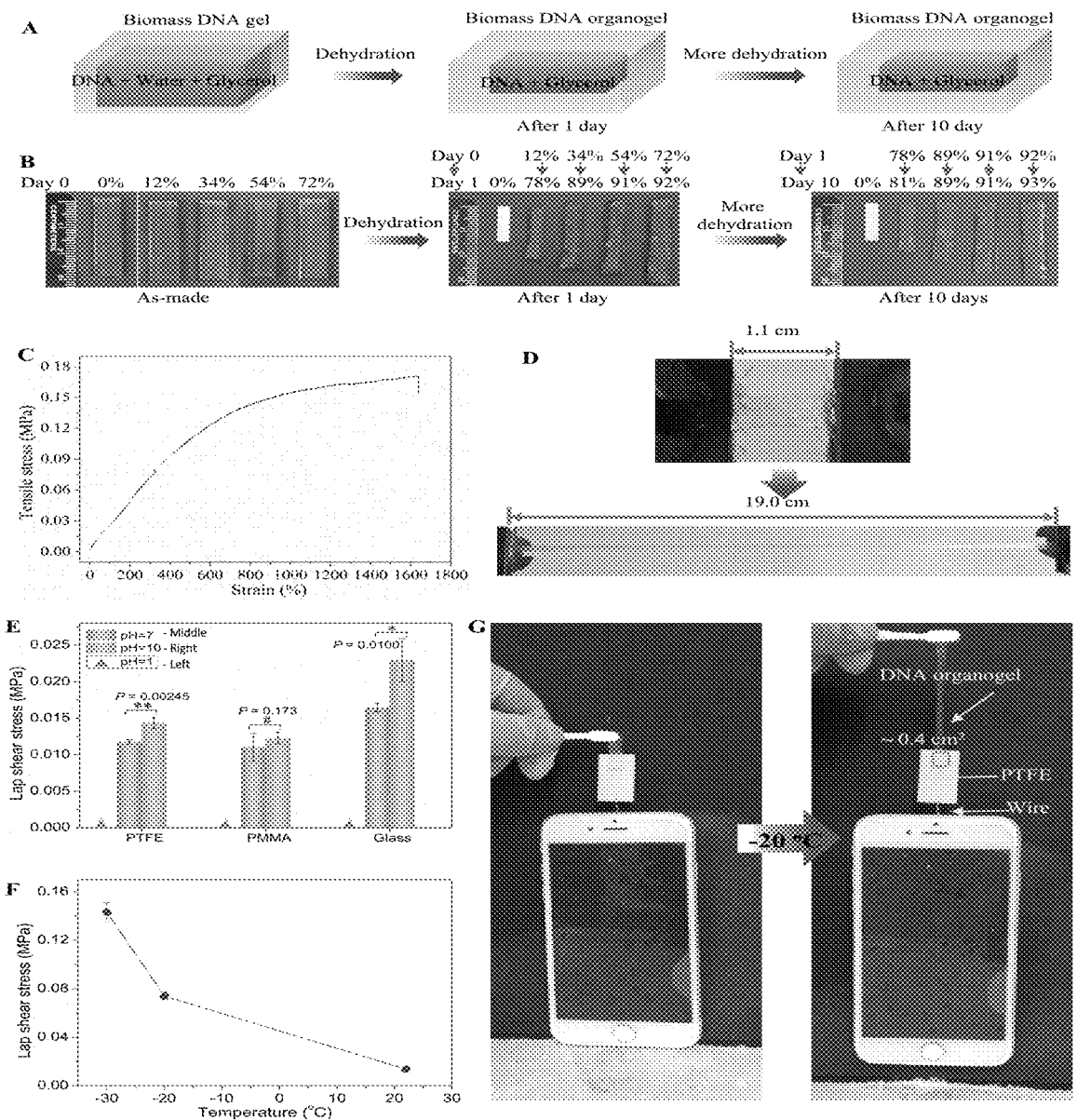
FIGS. 24A-24G show preparation and mechanical and adhesive properties of biomass DNA organogels. (A) Preparation scheme of biomass DNA organogels. (B) Variations of morphologies and appearances in the preparation process of biomass DNA organogels. The percentage numbers represented glycerol/water plus glycerol (wt %). A stress-strain curve (C) and corresponding stretching photographs (D) of an organogel with 31.6% biomass DNA. (E) Adhesive strengths of biomass DNA organogels with different pH on different substrates (#P>0.05, *P<0.05, **P<0.01). (F) Temperature-dependent adhesive strengths of biomass DNA organogels on a Teflon surface. (G) At −20° C., a cell phone was completely lifted by a very small biomass DNA organogel (about 0.4 $cm^2$). Significance according to a one-tailed homoscedastic t-test. Error bars represent the standard deviation of 3 measurements.
Figures 25A, 25B, 25C:
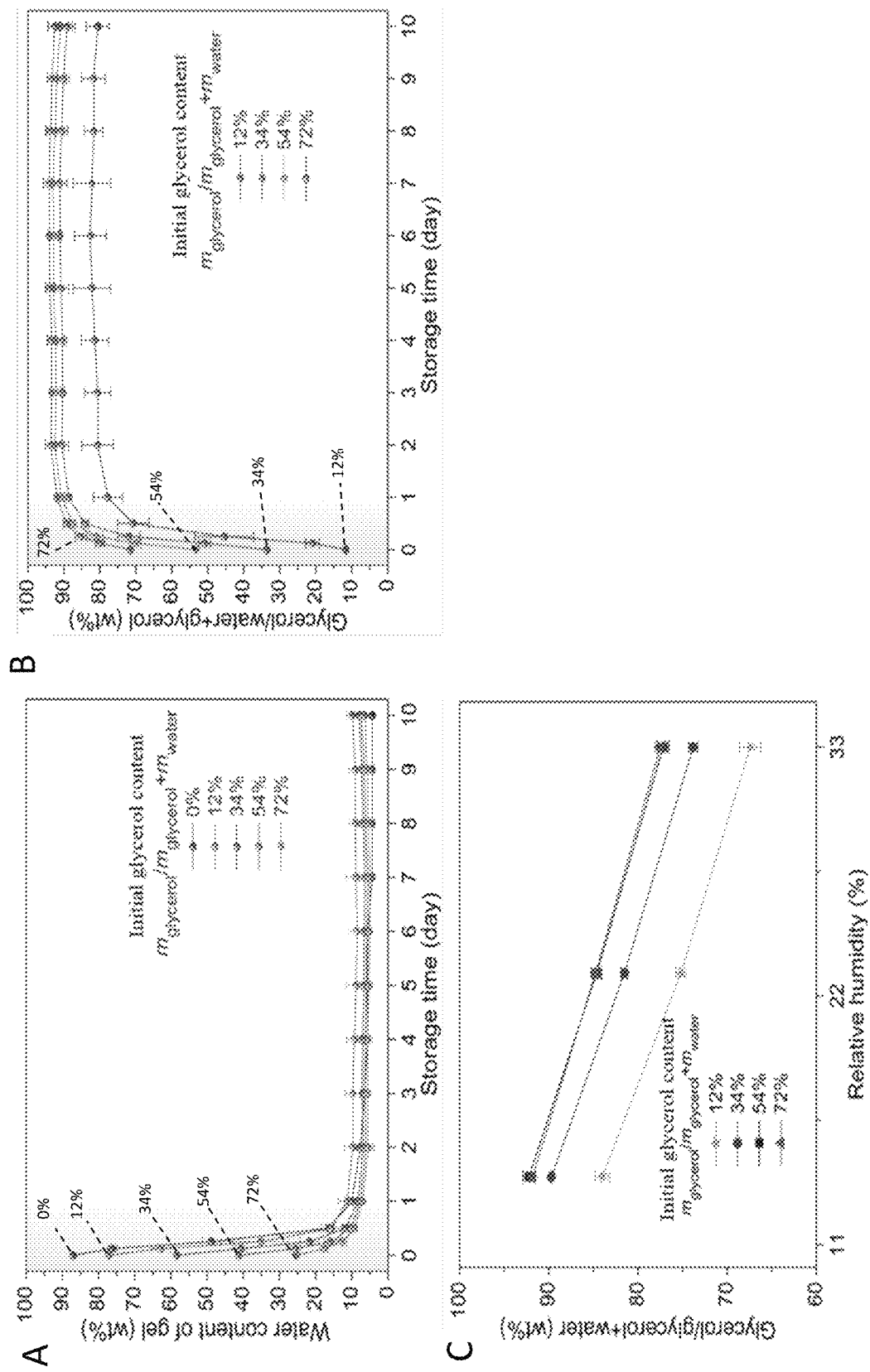
FIGS. 25A-25C show a dehydration process of biomass DNA gels and the effect of humidity on the glycerol content of DNA organogels. (A) Variation of water contents of biomass DNA gels during dehydration process. (B) Variation of glycerol contents of biomass DNA gels during dehydration process. (C) Effect of humidity on the glycerol contents of biomass DNA organogels. Error bars represent the standard deviation of 3 measurements.

In this example, glycerol was selected as the organic solvent to replace water because glycerol had a negligible vapor pressure under ambient conditions (~0.02 Pa at 25° C.) and was hygroscopic and biocompatible. Biomass DNA organogels were fabricated by dehydrating the DNA gels that were synthesized in the solvents consisting of different ratios of water and glycerol (FIGS. 24A, 25). Water was evaporated by drying the gels at the room temperature with 14% relative humidity. After one day of drying, the water contents decreased dramatically from approximately 90% down to 5-10%, while the glycerol content increased up to approximately 90%. The drying reached a plateau after one day. With the increase of the relative humidity, the glycerol content of biomass DNA organogels decreased, while the water content increased. Saturated magnesium chloride solution and saturated potassium acetate solution were used to control the relative humidities of 23% and 33% at room temperature (22° C.), respectively.

Figure 26:
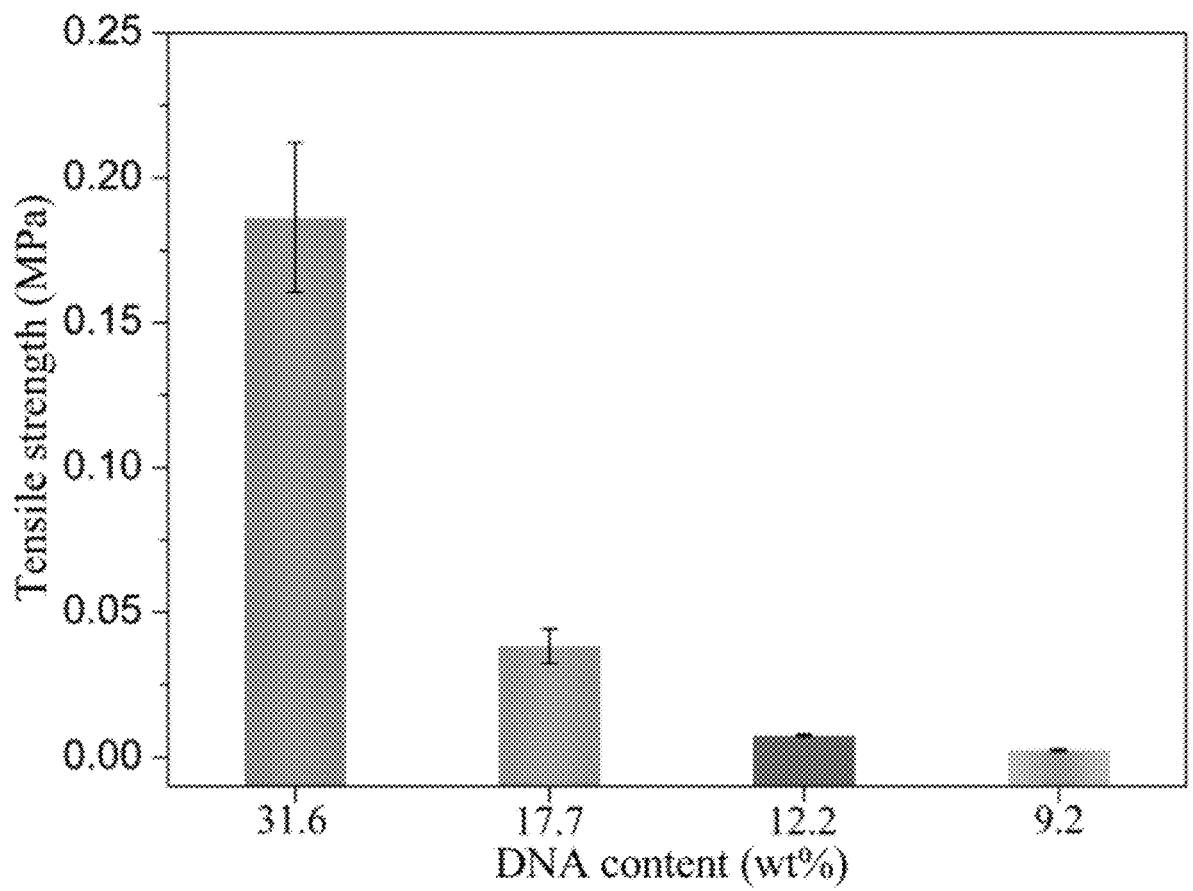
FIG. 26 shows the mechanical strengths of biomass DNA organogels with different DNA contents (wt %). Error bars represent the standard deviation of 3 measurements.

The formation of biomass DNA organogels from the initial glycerol/water DNA gels was accompanied by obvious volumetric changes. The more the initial glycerol content, the less the decrease of the volume. When the glycerol percentage in the initial DNA gels reached above 70%, the volume reduction was barely noticeable (FIG. 24B). Interestingly, the transparencies of the DNA hydrogel and DNA organogel were totally different. For the DNA hydrogel, after dehydration it went from transparent to opaque with a rigid, solid, and plastic-like appearance. For the DNA organogel, however, it remained transparent after dehydration and remained a soft gel. The biomass DNA organogel also possessed desirable mechanical properties. With increasing DNA content, the tensile strength increased gradually, and the organogel containing 31.6% DNA had the highest mechanical strength (FIG. 26). The tensile strength was around 0.17 MPa with a tensile strain of 1600% (FIGS. 24C-24D). The results indicated that a higher DNA concentration gave rise to higher mechanical strength. In addition, the volume reduction of organogel sample with a low glycerol content also implied that the cohesion caused by stronger hydrogen bonding interactions among glycerol molecules contributed to the high mechanical strength.

Figure 27:
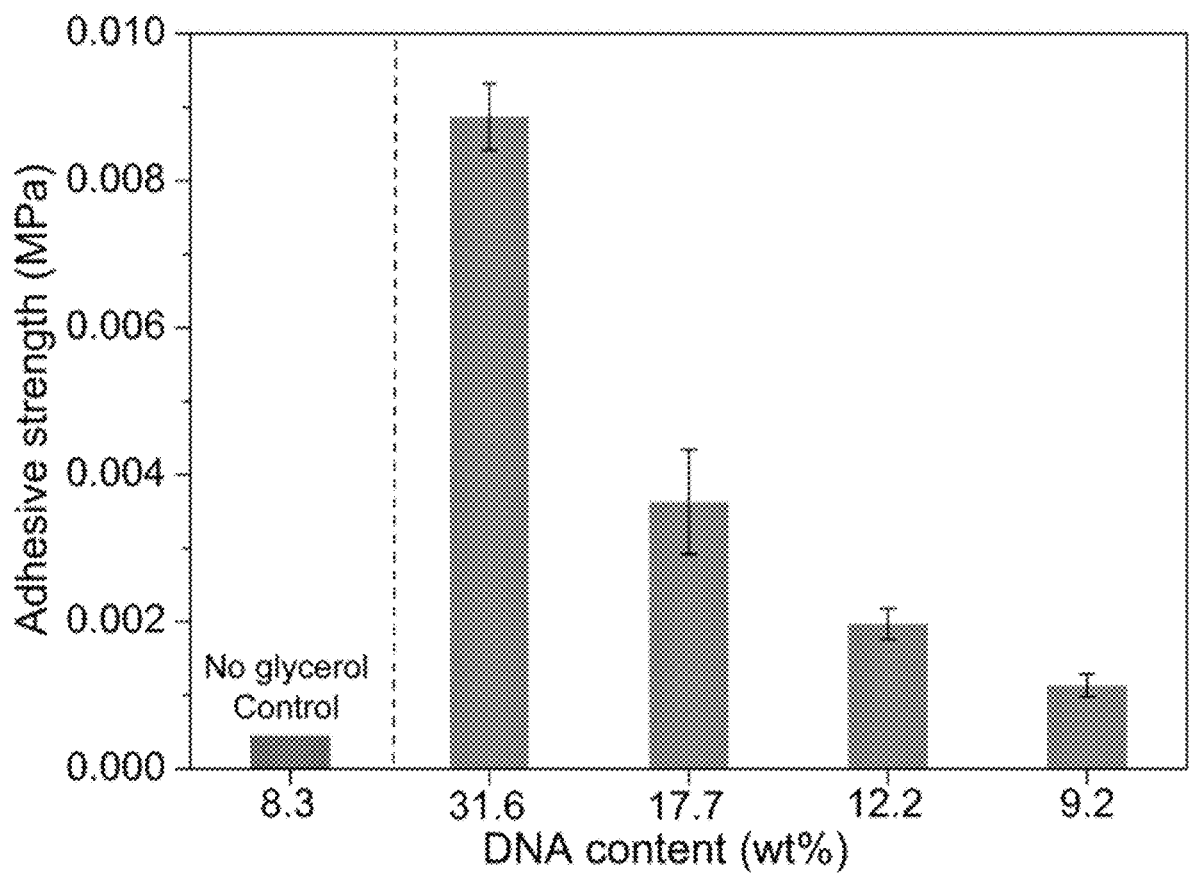
FIG. 27 shows the lap adhesive strengths on Teflon of biomass DNA organogels with different DNA contents (wt %). Error bars represent the standard deviation of 3 measurements.
Figure 28:
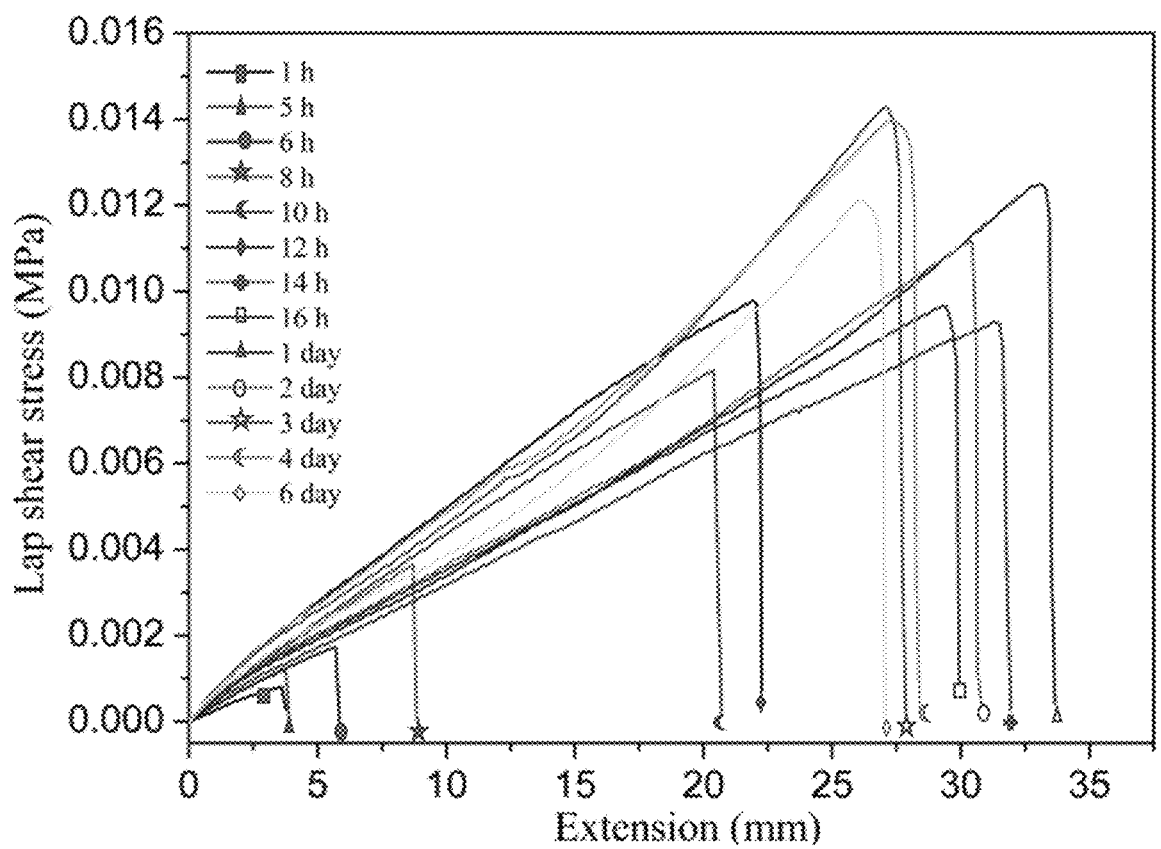
FIG. 28 shows the variation of adhesive strength of a biomass DNA gel over a long period time.

The biomass DNA organogels had unique and surprising adhesive behavior on different solid surfaces including poly (methyl methacrylate) and glass (FIG. 24E). Unexpectedly, the biomass DNA organogels even stuck strongly on a polytetrafluoroethylene (PTFE) surface, a well-known and widely used non-stick coating (commercially known as Teflon). The biomass DNA organogel's unusual adhesive behavior on the PTFE surface was proportional to the concentration of DNA. The higher the DNA concentration, the stronger the adhesiveness (FIG. 27). The adhesiveness was higher under alkaline condition than under neutral condition; there was no adhesiveness (too low to be measured) when under the acidic condition (FIG. 24E). The adhesive strength was measured over a long period time (up to six days) as water evaporated gradually from the initial gel. The results showed that the adhesiveness increased rapidly with water evaporation and then stabilized when the glycerol content reached a steady level (FIG. 28), indicating that the higher the glycerol concentration, the stronger the adhesiveness. This is on account of the fact that in the glycerol environment, acid protonated the amine groups of DNA bases, disabling the adhesion by breaking the hydrogen bonds; On the other hand, neutralized condition or alkali kept or slightly enhanced hydrogen-bonding ability of amine group of DNA bases, enabling the adhesion. The pH-dependent adhesiveness of biomass DNA organogels provided a direct evidence to support a hydrogen bonding-based adhesion. Usually, intermolecular forces are responsive for adhesion, which can be divided into chemical adhesion (covalent bond, hydrogen bond, and electrostatic force), dispersive adhesion (Van der Waals forces), and diffusive adhesion. There is no single theory that can cover all adhesion. Therefore, the adhesion on different substrates of the biomass DNA organogel can result from hydrogen bond, Van der Waals forces, and electrostatic force. However, for the PTFE in the experiments, due to the fact that PTFE is a non-polar and uncharged material with extremely low surface energy, the hydrogen bonding could dominate the adhesion of DNA organogel. Taken together, it is speculated that hydrogen bonds (e.g., between N—H and C—F from DNA bases and PTFE, respectively), probably contributed to the main interaction force at the contacting interface. Also, with its higher viscosity, glycerol not only provided stronger interfacial interactions than water but also increased intermolecular interactions in the polymer network, resulting in an enhanced cohesion of biomass DNA organogels.

Figures 29A, 29B:
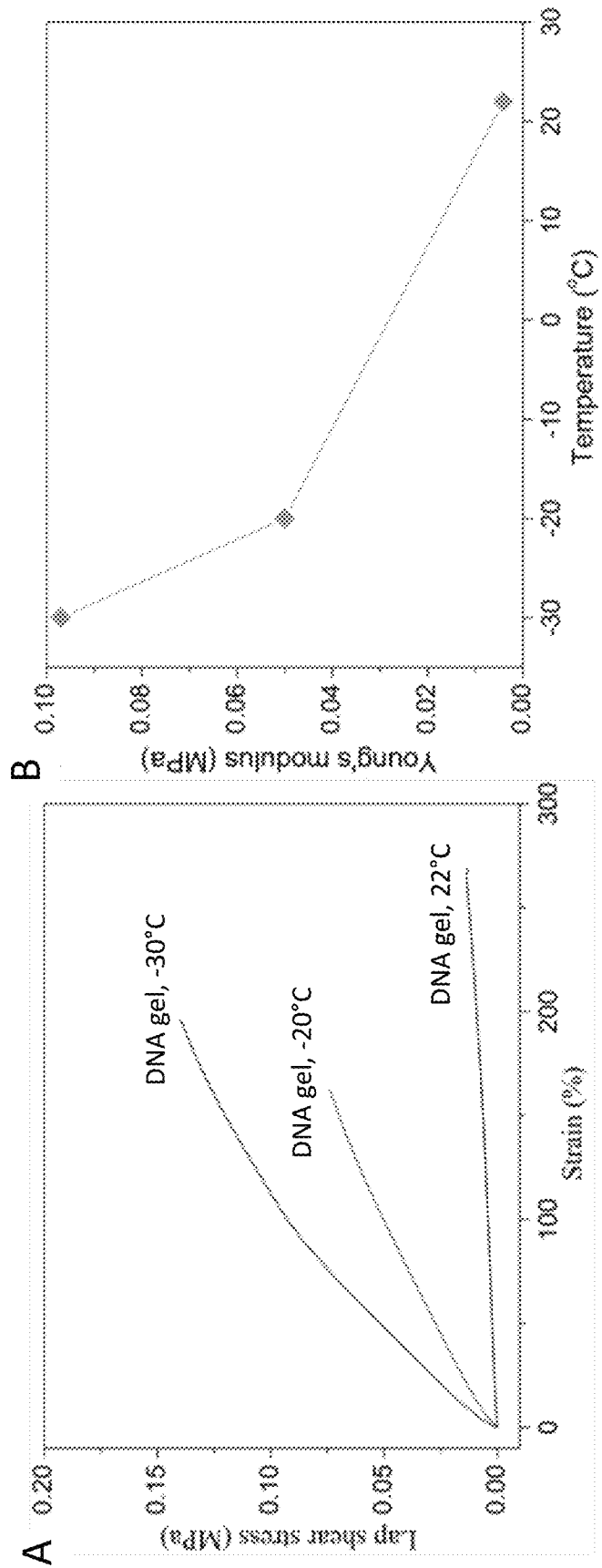
FIGS. 29A-29B show (A) the lap adhesive strengths on Teflon and (B) the young's moduli of biomass DNA organogels (31.6% DNA) under freezing temperatures.

It was also hypothesized that, owing to the anti-freezing property of glycerol, the biomass DNA organogels would show anti-freezing behavior. Indeed, the organogel did not freeze even after storing at −20° C. for three months or even longer. The adhesiveness of biomass DNA organogels was evaluated under freezing temperatures, where most adhesives failed to function. The biomass DNA organogels, however, presented an unusual temperature-dependent adhesive behavior. With the decrease of temperature from room temperature to −30° C., the adhesive strengths (lap shear strength, FIG. 24F) increased remarkably. The adhesive strength at −30° C. increased up to 10 times compared with those of under room temperature, and the young's moduli increased 24 times than those of under room temperature (FIG. 29). This temperature-dependent behavior was consistent with the temperature-dependent hydrogen bonding, supporting the aforementioned hypothesis that the mechanism of the DNA organogel adhesion on PTFE was mainly due to hydrogen bonding. This unusual adhesive behavior was further visually demonstrated with a lifting experiment at −20° C., where a small patch the size of a small fingernail (0.4 cm2) of biomass DNA organogel was enough to adhere to a PTFE nonstick surface to fully lift a cell phone (148 g) (FIG. 24G). It is envisioned that this disposable, anti-freezing soft material with desirable mechanical properties will have great potential in soft robotics and electronics under cold environment.

Example 4: Biomass DNA Composite Membranes

This example provides examples of biomass DNA composite membranes of the present disclosure and examples of methods of making and characterization of biomass DNA composite membranes of the present disclosure.

Alkaline solution was used as the trigger to fabricate biomass DNA hydrogels; however, the triggering of Michael addition reactions is not limited to a solution phase. So far, conventional hydrogels have been fabricated with various precursors by light, heat, chemical, and acoustic triggers. However, there remain challenges to regulate the gelation dynamics, for instance, to initiate and/or to terminate the gelation process optionally.

Figures 30A, 30U:
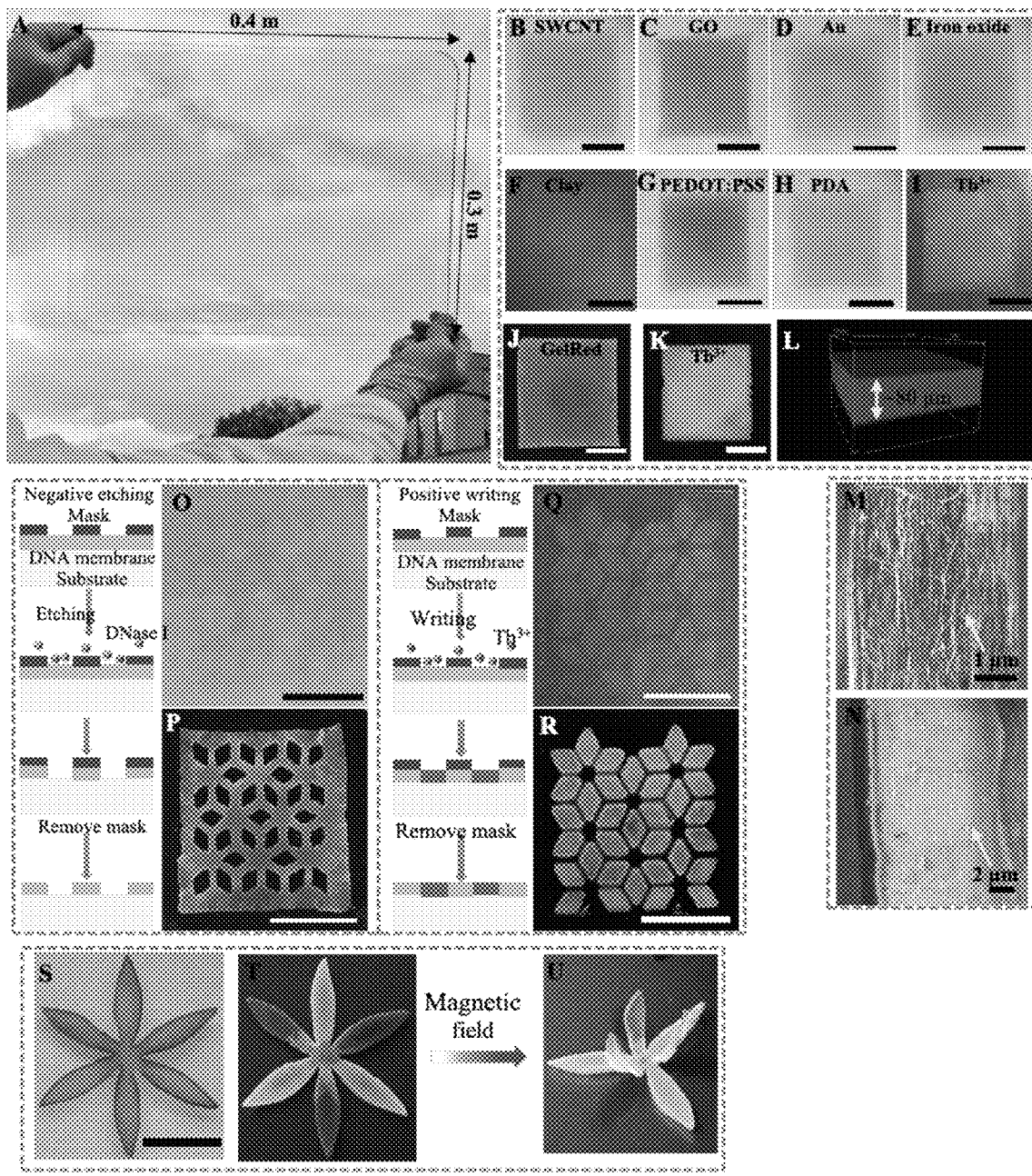
FIGS. 30A-30U show gas-triggered functional composite membranes made from biomass DNA. (A) A large-scale preparation of biomass DNA hydrogel membrane triggered by ammonia. (B to I) Photographs of biomass DNA composite membranes with SWCNT, GO, Au nanoparticles, iron oxide particles, nanoclays, PEDOT:PSS, PDA, and $Tb^{3+}$, respectively. (J) A fluorescence image of DNA-SWCNT composite membrane stained by GelRed. (K) A fluorescence image of DNA-Tb' composite membrane. (L) A laser confocal microscopic image of DNA-SWCNT composite membrane stained by GelRed. (M and N) Cross-sectional SEM images of DNA-SWCNT and DNA-iron oxide particles composite membrane, respectively. (O and P) A photograph and a fluorescence image (GelRed), respectively, of a pattern consisting of groups of diamond-shaped holes by a negative etching of a DNA-SWCNT membrane. (Q and R) A photograph and a fluorescence image, respectively, of a positive pattern consisting of groups of diamond shapes by spraying $Tb^{3+}$ solution on a masked DNA membrane. (S and T) A photograph and a fluorescence image, respectively, of a four-component biomass DNA flower fused together. (U) The DNA flower closed by applying a magnetic field. (scale bars: 1 cm)
Figures 31A, 31B:
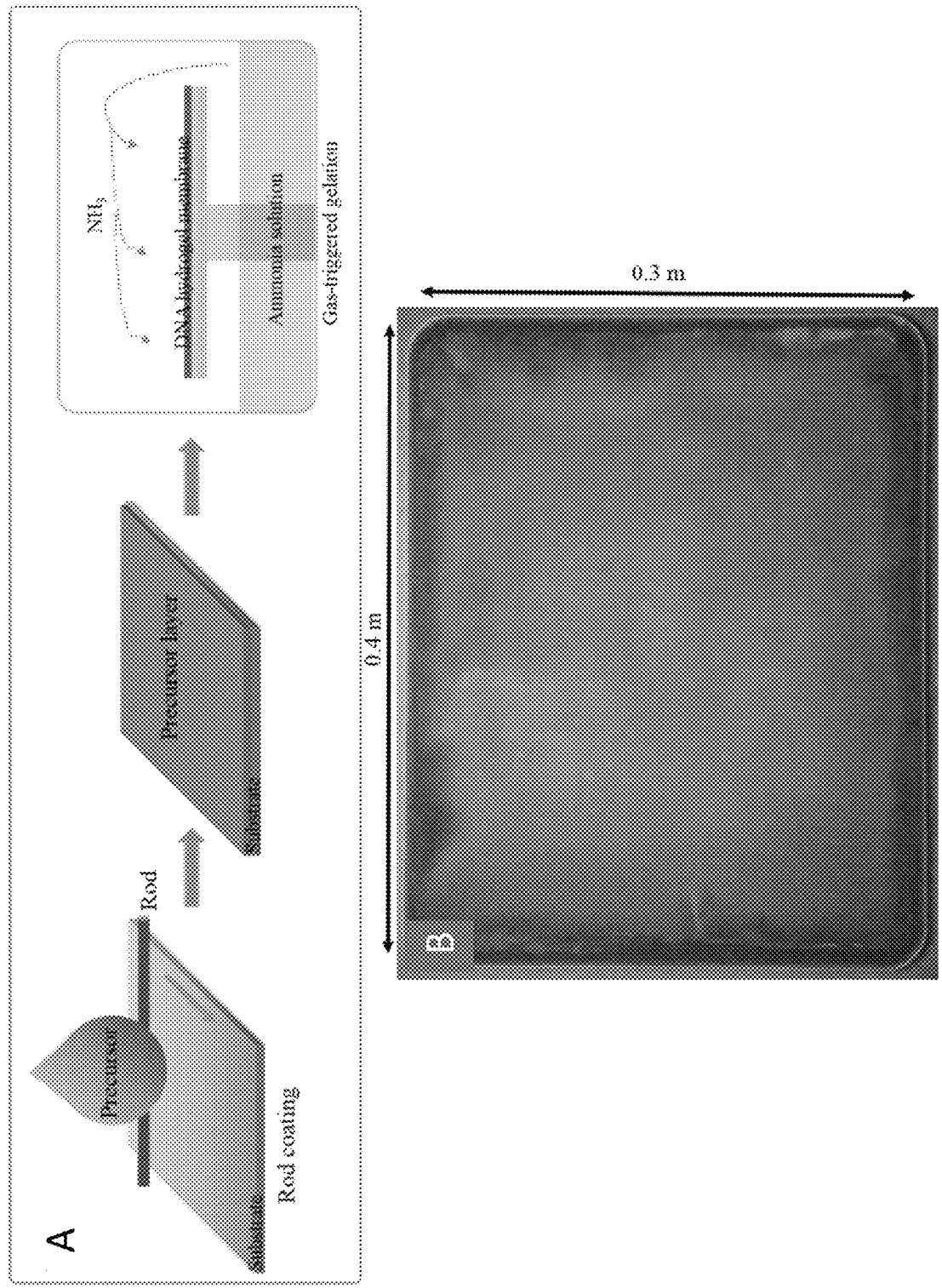
FIGS. 31A-31B show (A) a preparation process of ammonia-triggered biomass DNA membranes and (B) a fluorescence image (stained by GelRed) of a large-scale biomass DNA membrane.
Figures 32A, 32B, 32C, 32D, 32E, 32F:
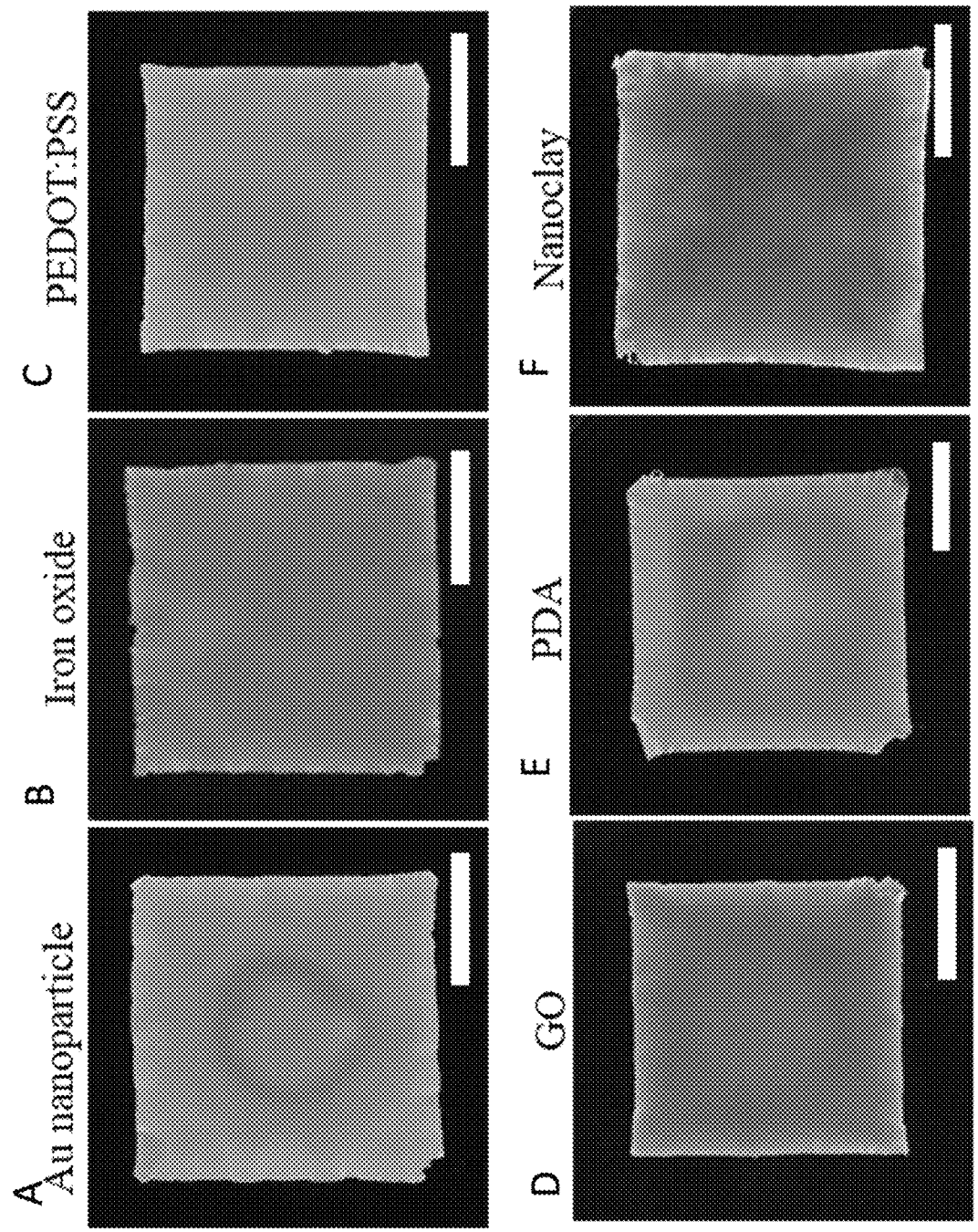
FIGS. 32A-32F show the fluorescence images (stained by GelRed) of (A) DNA-Au nanoparticle, (B) DNA-iron oxide particle, (C) DNA-PEDOT:PSS, (D) DNA-GO, (E) DNA-PDA, and (F) DNA-Nanoclay membranes. All scale bars were 1 cm.
Figures 33A, 33B, 33C, 33D, 33E, 33F:
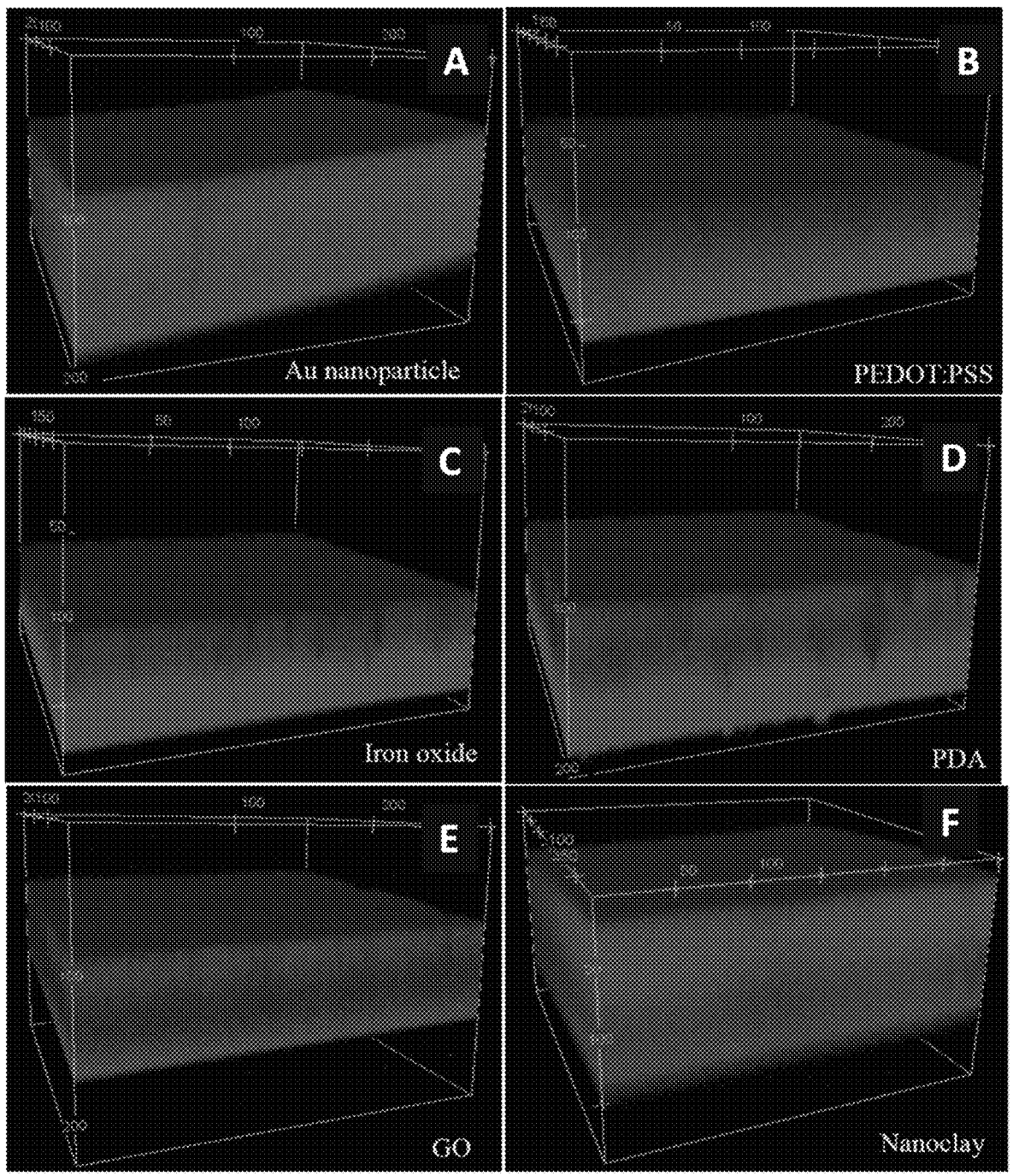
FIGS. 33A-33F show the confocal fluorescence images (stained by GelRed) of (A) DNA-Au nanoparticle, (B) DNA-PEDOT:PSS, (C) DNA-iron oxide particle, (D) DNA-PDA, (E) DNA-GO, and (F) DNA-Nanoclay membranes.
Figures 34A, 34B:
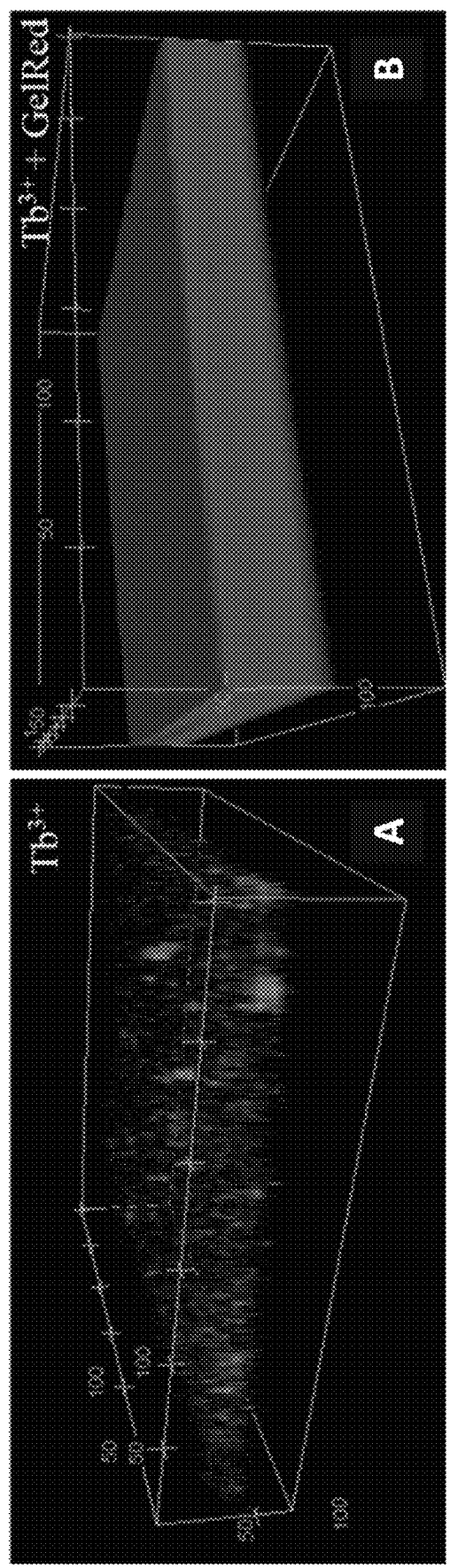
FIGS. 34A-34B shows the confocal fluorescence images (right image, stained by GelRed) of a DNA-Tb' membrane.
Figures 35A, 35B, 35C, 35D, 35E, 35F:
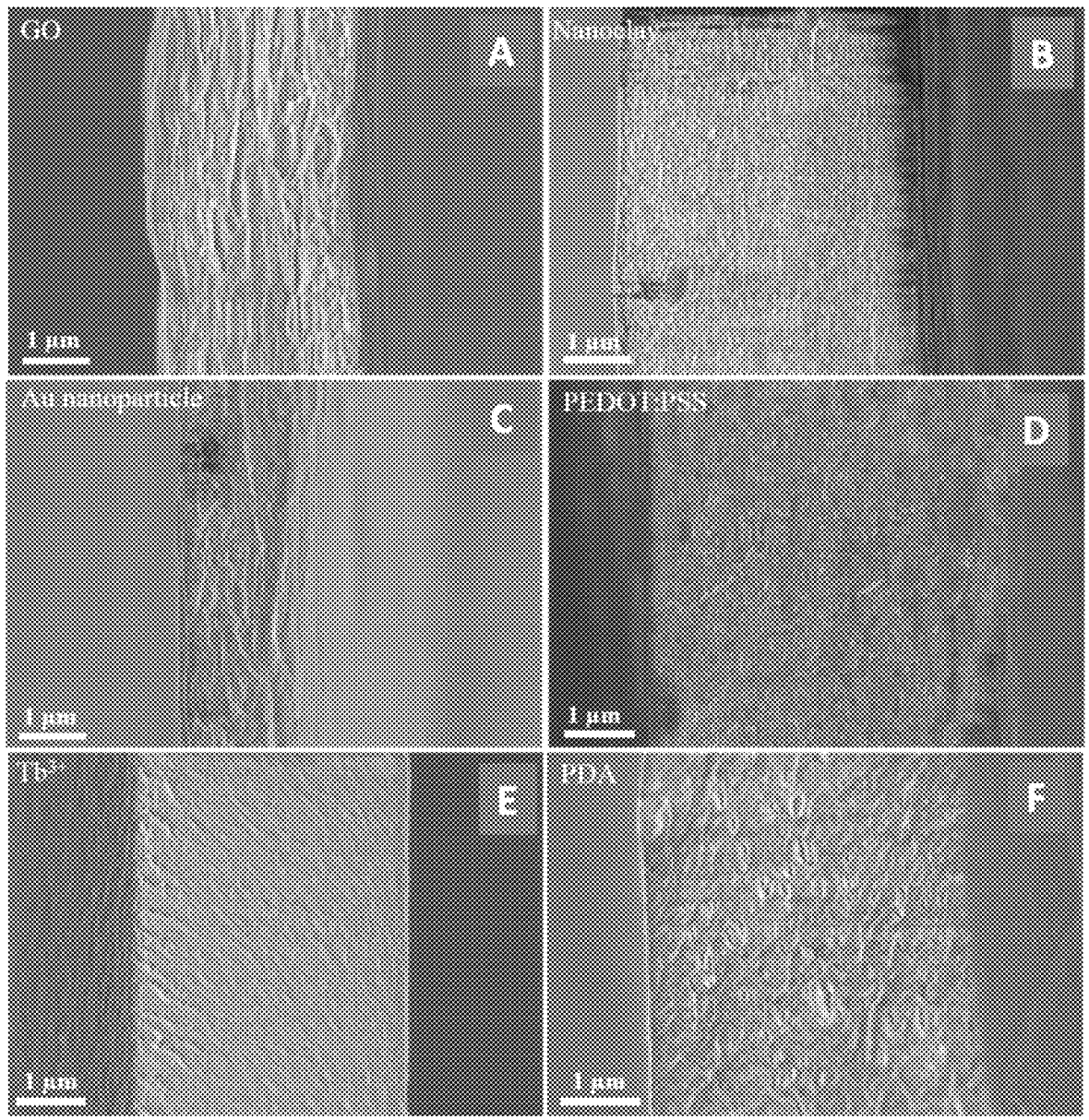
FIGS. 35A-35F shows the SEM images of (A) DNA-GO, (B) DNA-Nanoclay, (C) DNA-Au nanoparticle, (D) DNA-PEDOT:PSS, (E) DNA-Tb', and (F) DNA-PDA membranes.

In this example, the dissolution and volatilization of gas in solution is a simple process that easily introduces and discharges the trigger component during the gelation. Ammonia, a highly volatile alkaline gas molecule, has been proved to be an ideal reagent to fabricate gas-triggered biomass DNA hydrogels and more importantly, to control the hydrogel format. Indeed, using an alkaline gas-mediated trigger, ammonia gas, biomass DNA hydrogel membranes were successfully prepared (FIGS. 11L-11M). More importantly, this ammonia gas-triggered method afforded fabrication of thin membranes of biomass DNA at the meter scale (FIG. 30A). Additionally, composite thin membranes were created through exposing spin-coated biomass DNA precursors in an ammonia gas atmosphere (FIG. 31), resulting in thin membranes with various dopants including single-wall carbon nanotubes (SWCNT, FIG. 30B), graphene oxides (GO, FIG. 30C), gold nanoparticles (Au, FIG. 30D), magnetic iron oxide particles (iron oxide, FIG. 30E), nanoclays (clay, FIG. 30F), poly(3,4-ethylenedioxythiophene)-poly (styrenesulfonate) (PEDOT:PSS, FIG. 30G), poly(10, 12-pentacosadiynoic acid) (PDA, FIG. 3011), and metal ions ($Tb^{3+}$, FIG. 30I).

The visual colors of biomass DNA composite membranes were consistent to those of the doped materials themselves, suggesting that the DNA was inert and did not affect the dopants. In addition, the composite membranes were stained by DNA specific fluorescent dye GelRed (FIGS. 30J, 32A-32F for other composite membranes), indicating that doped materials did not interfere DNA either. In addition to pre-loading the dopants, post-loading the dopants was relatively easy to accomplish. For example, by soaking the DNA-only thin membrane (no fluorescence) in a Tb3+ solution (no fluorescence), the composite membrane started emitting green fluorescence, suggesting that specific interactions occurred between DNA bases and Tb3+(FIG. 30K).

The thicknesses of initial composite membranes were ranged from 50 µm to 100 µm (FIGS. 30L, 33A-33F, 34). The excitation wavelength of $Tb^{3+}$-DNA complex (FIG. 34) was far away from the laser wavelength that the Olympus FV1000 confocal microscope provided, probably resulting in the weak fluorescence for a high-quality image. The GelRed stained DNA-$Tb^{3+}$ membrane provided a good fluorescence image for thickness measurement.

Figures 36A, 36B, 36C, 36D:
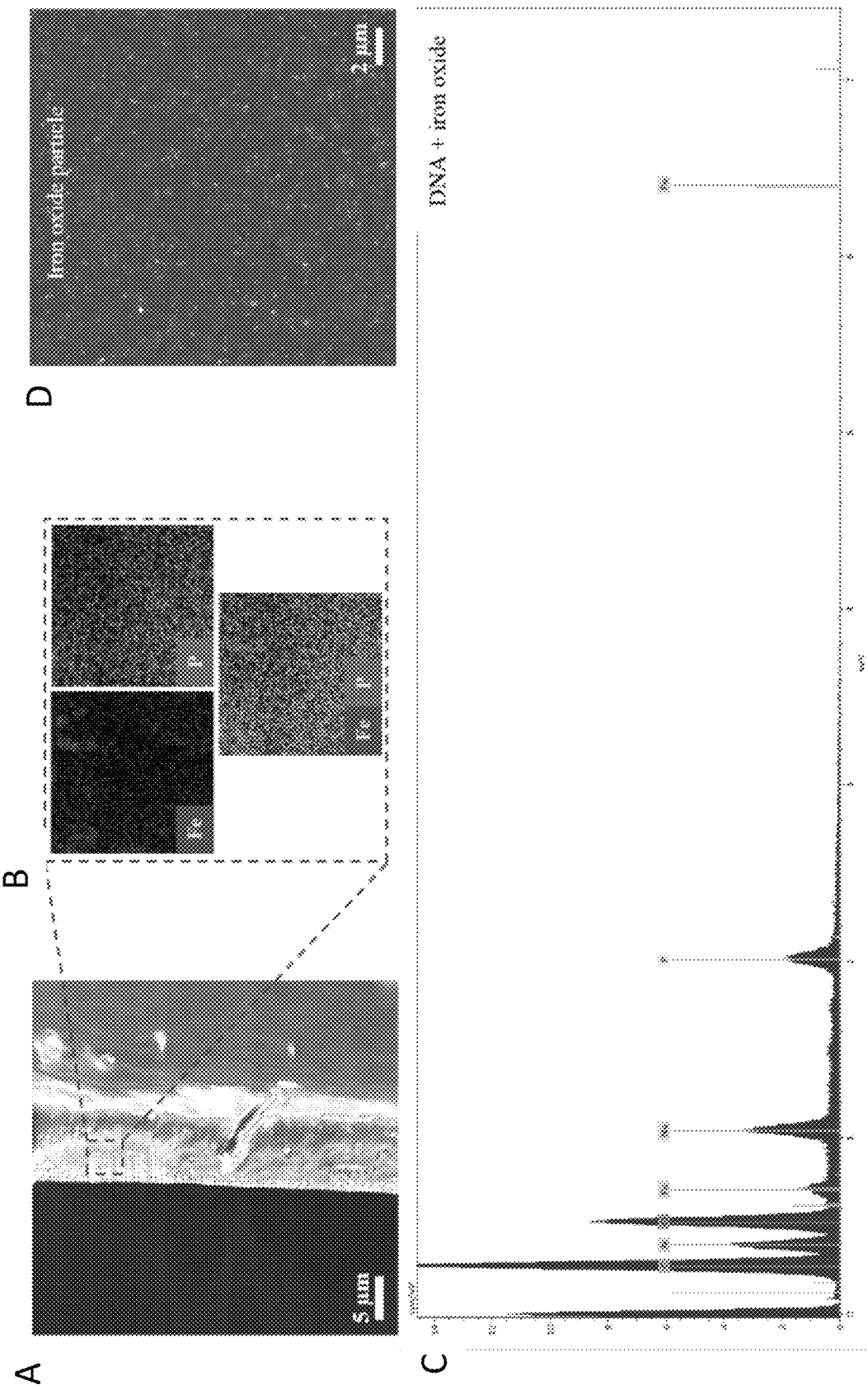
FIGS. 36A-36D show the EDX analysis of a DNA-iron oxide particle membrane and the morphology characterization of the iron oxide particles. (A) A SEM image of the DNA-iron oxide particle membrane. (B) The elemental mapping (Fe and P) of the DNA-iron oxide particle membrane. (C) The EDX spectrum of the DNA-iron oxide particle membrane. (d) A SEM image of iron oxide particles.
Figures 37A, 37B, 37C, 37D:
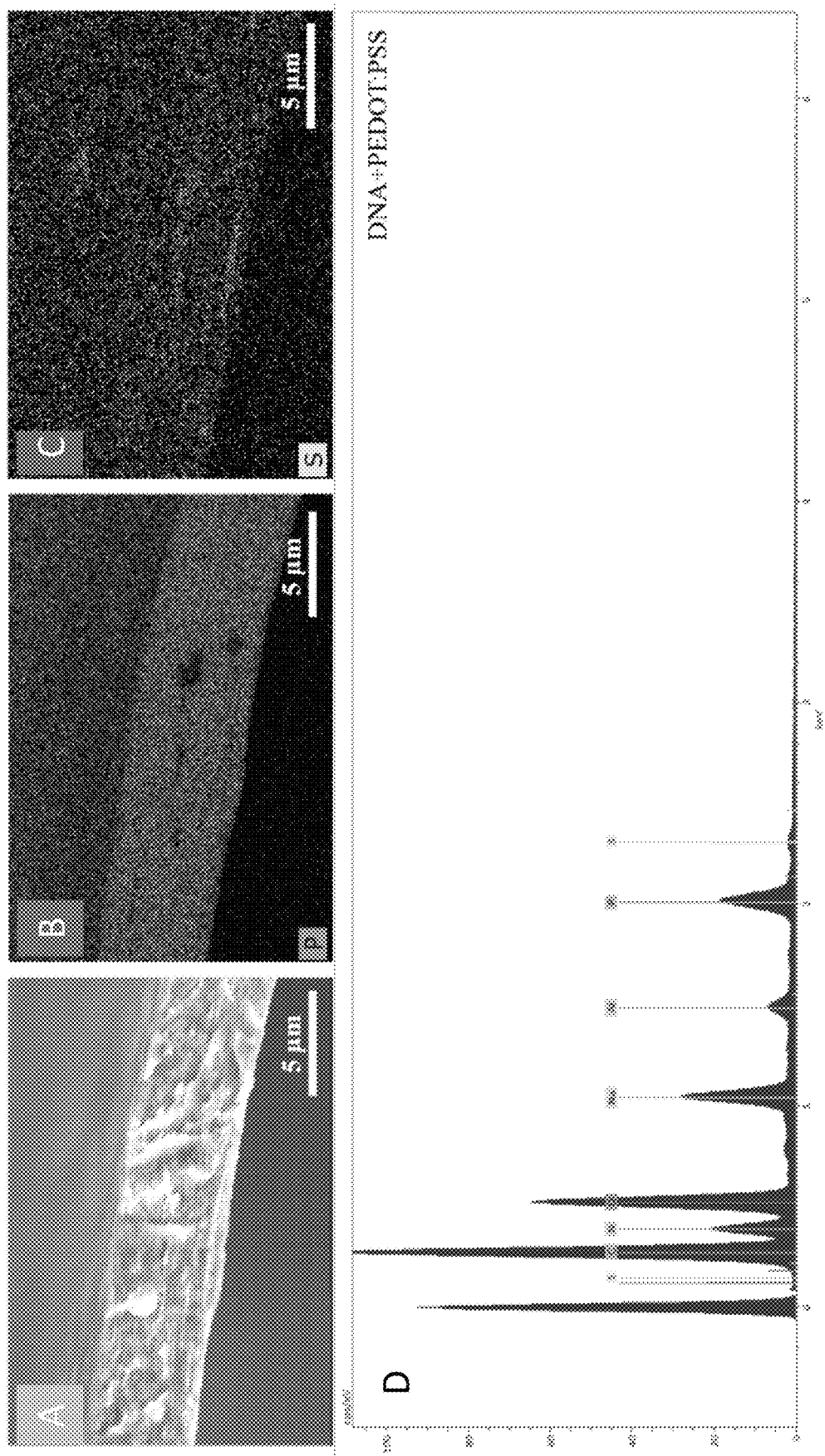
FIGS. 37A-37D show the EDX analysis of a DNA-PEDOT:PSS membrane. (A) A SEM image of the DNA-PEDOT:PSS membrane. (B) The elemental mapping (P) of the DNA-PEDOT:PSS membrane. (C) The elemental mapping (S) of the DNA-PEDOT:PSS membrane. (D) The EDX spectrum of the DNA-PEDOT:PSS membrane.
Figures 38A, 38B:
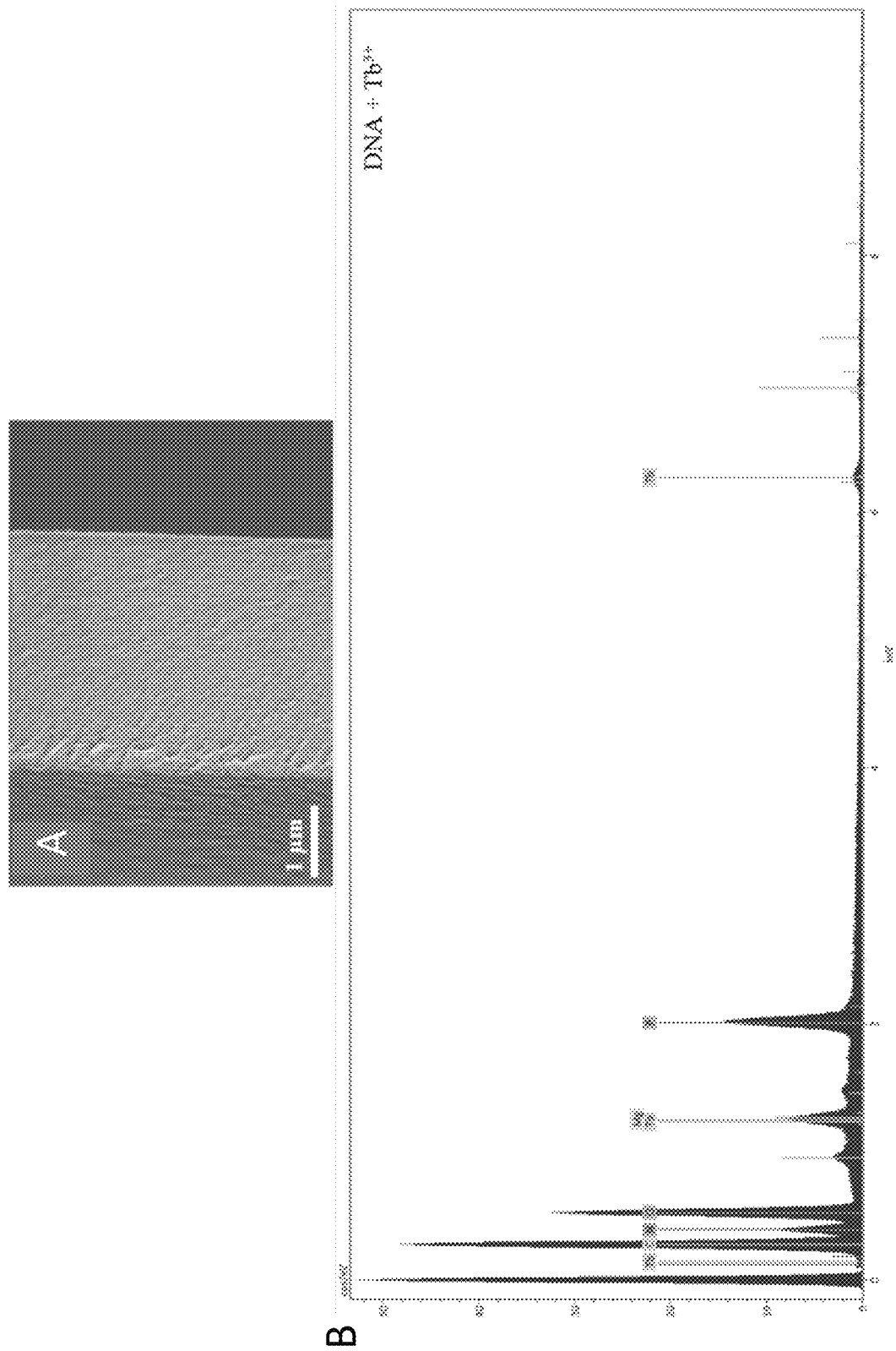
FIGS. 38A-38B show the EDX analysis of a DNA-Tb' membrane. (A) A SEM image of the DNA-Tb' membrane. (B) The EDX spectrum of a DNA-Tb' membrane.

After dehydration, the thicknesses were reduced to about 5 µm (FIGS. 35A-35F). The characteristic morphologies of composite membranes were observed through SEM; distinct features like SWCNT fibers (FIG. 30M), magnetic iron oxide particles (FIG. 30N), and graphene oxide sheets (FIG. 35A) were clearly seen. Furthermore, energy dispersive X-ray spectroscopy revealed that the iron, sulfur, and terbium elements were well dispersed in biomass DNA composite membranes doped with magnetic iron oxide particles, PEDOT:PSS, and Tb3+, respectively (FIGS. 36-38).

Since biomass DNA in thin membranes still possessed DNA's unique properties, they remained as substrates for DNA enzymes (FIG. 17) and also for other DNA-specific interactions such as chelating and intercalating (FIG. 30K).

Taking advantages of these properties, biomass DNA membrane was patterned through either a negative, etching approach or a positive, direct writing approach. For the negative etching, nucleases (DNase I) and a mask were used to digest away unwanted regions of DNA membrane, resulting in a precise pattern consisting of groups of diamond-shaped holes on a biomass DNA-SWCNT composite membrane (FIGS. 30O-30P). For the positive, direct writing, an ordered pattern consisting of groups of diamond shapes was successfully written by spraying Tb' solution on a masked membrane (FIGS. 30Q-30R). Both the etching and writing methods were controllable, and the resulting edges were very smooth.

In addition to etching in and writing on the membranes, biomass DNA hydrogels were also patterned by fusing several differently doped biomass DNA hydrogels into one pre-designed pattern by mixing the different precursors together, resulting in multi-component DNA hydrogels with multi-functionalities. As an example, a four-component DNA flower was constructed with two different types of petals. One petal consisted of SYTO 64 Red and magnetic iron oxides (shown as brown petals under ambient light, FIG. 30S, and crimson fluorescent color under UV, FIG. 30T), and the other petal consisted of SYBR Green I and SWCNT (shown as dark grey petals under ambient light, FIG. 30S, and green fluorescent color under UV, FIG. 30T). When a magnetic field was applied, the entire DNA flower closed and opened ("blossomed"), just as designed (FIG. 30U).

Example 5: Biomass DNA Plastics

This example provides examples of biomass DNA plastics of the present disclosure and examples of methods of making and characterization of biomass DNA plastics of the present disclosure.

Figure 39:
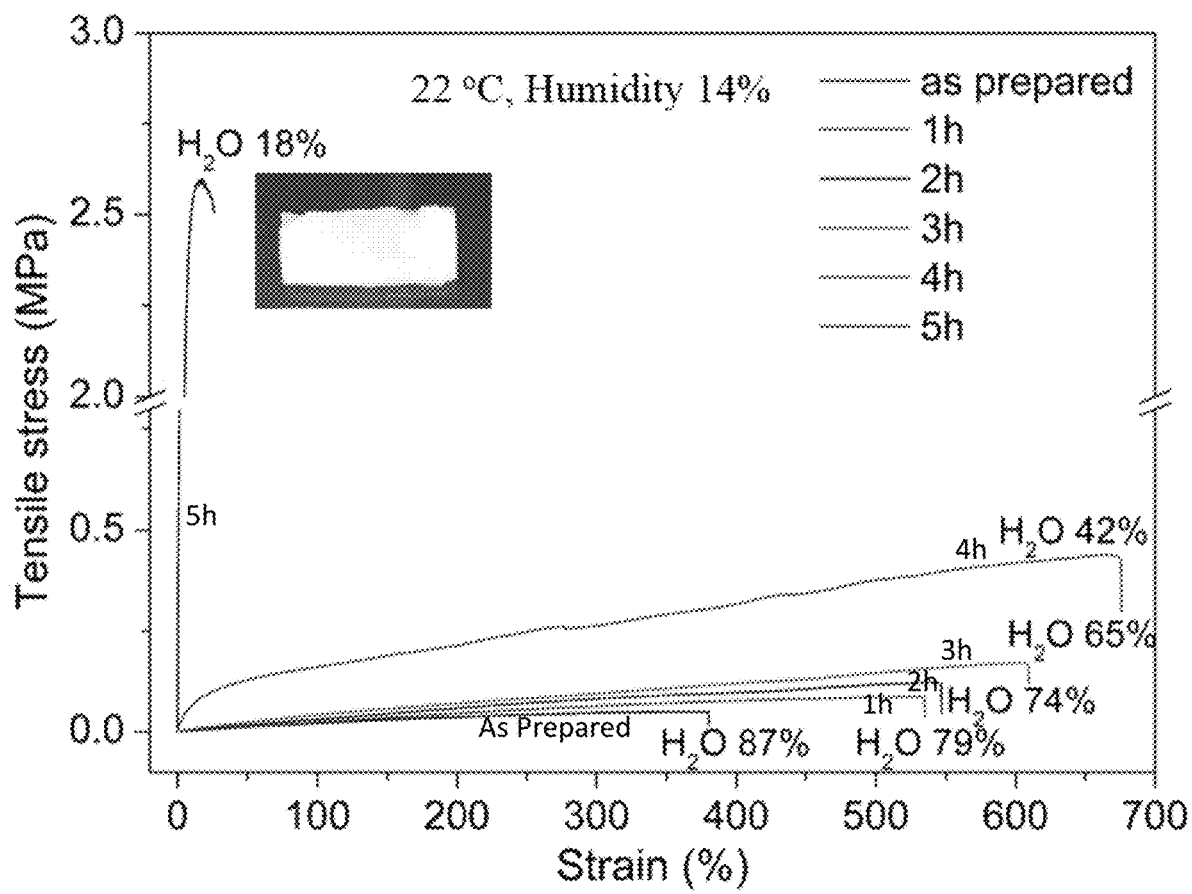
FIG. 39 shows the variation of mechanical property of a DNA hydrogel during the dehydration process.

In this example, the mechanical properties of DNA hydrogels were controlled by regulating the dehydration process (FIG. 39), resulting in a transition from soft gels to stiff, plastic-like materials due to the polymeric attributes of biomass DNA. When the DNA hydrogel was exposed to air, the DNA hydrogels had an interesting water-dependent alteration of mechanical properties. With the increase of exposed time, the water content was decreased gradually, and the mechanical strength and young's modulus were enhanced gradually. There was a sudden change when the water content was about 42%. Finally, when the water content was about 18%, the mechanical strength and young's modulus of dried DNA hydrogel increased remarkably, and the mechanical property was similar to that of the plastic materials, which indicated that biomass DNA hydrogel turned from soft gel (young's modulus, 20 KPa) to stiff plastic-like material (young's modulus, 50 MPa) (inset image of dried hydrogel).

Figures 40A, 40B, 40C, 40D, 40E:
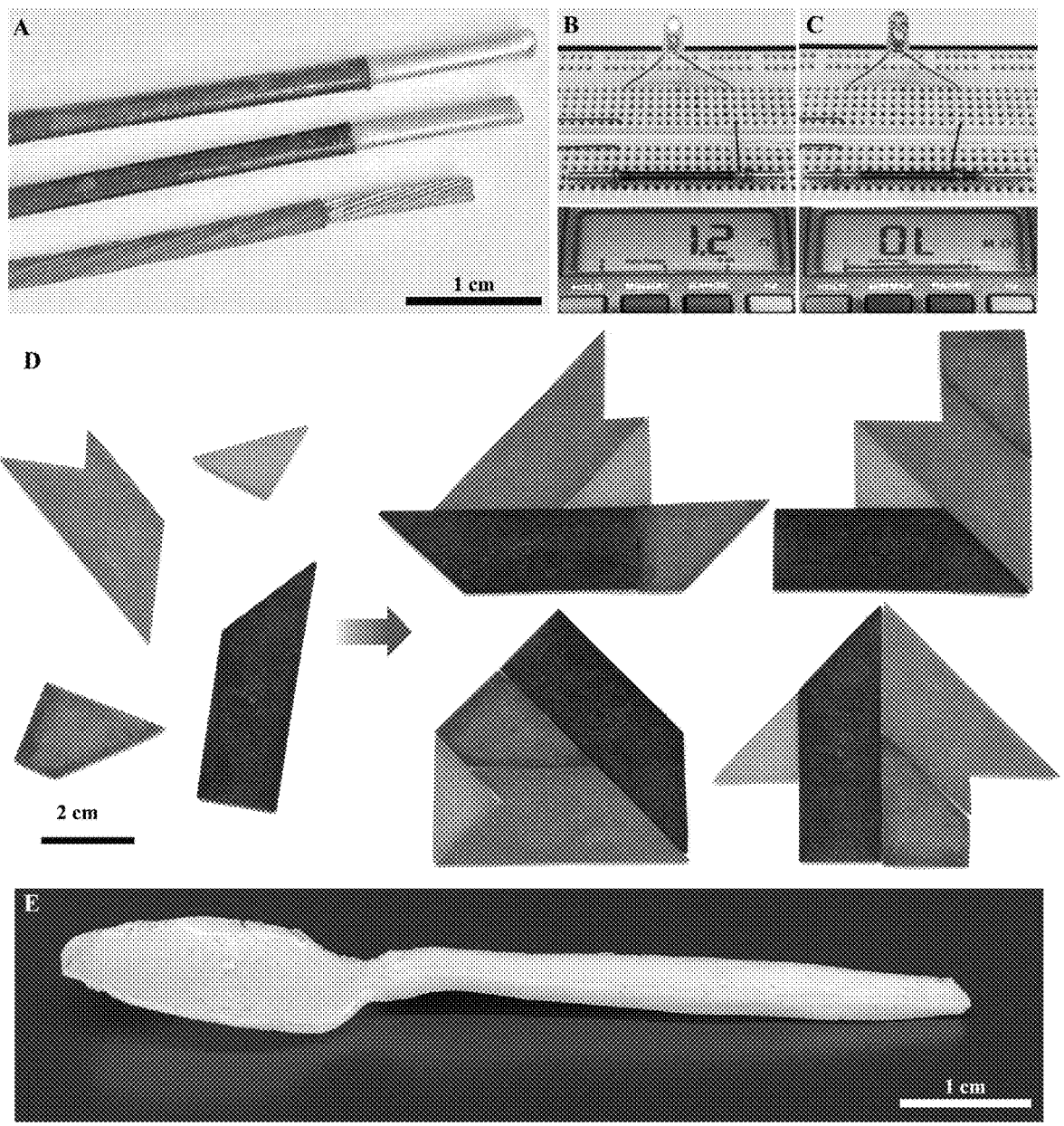
FIGS. 40A-40E show a demonstration of biomass DNA plastic objects: (A) Biomass DNA-coated copper wires. (B and C) Insulating biomass DNA coatings switched a circuit on and off, respectively. (D) Biomass DNA T-puzzle toys. (E) A biomass DNA spoon. All the colors were from food dyes except that of the spoon (E), which was a natural color.
Figures 41A, 41B, 41C, 41D:
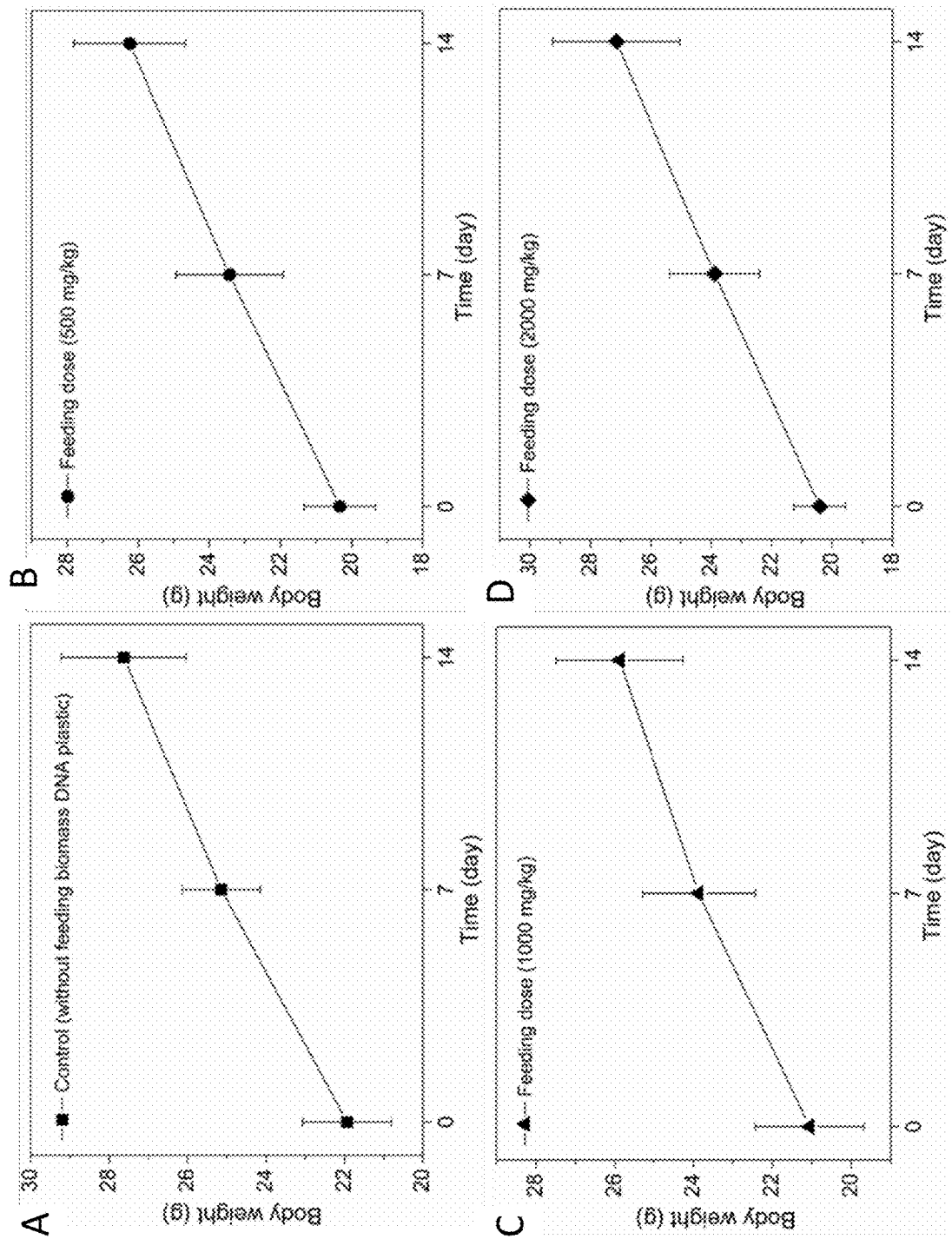
FIGS. 41A-41D show the assessment of acute oral toxicity of biomass DNA plastic. (A) the body weight changes in mice without orally administrated DNA plastic. (B to D) the body weight changes in mice with orally administrated DNA plastic (500 mg/kg, 1000 mg/kg, 2000 mg/kg, respectively). Error bars represent the standard deviation from n=8 mice in each group.

Since plastics have been one of the largest categories of petrochemical-derived materials, and since plastics have been widely used in daily life for applications such as wire coatings, toys, and utensils, just to name a few, the feasibility of using the biomass DNA materials to potentially replace petrochemical-based plastics was explored. To demonstrate such a potential, the biomass DNA-based materials were used to construct one-dimensional, two-dimensional, and three-dimensional daily, plastic objects. For the 1D, copper wires were coated using biomass DNA with the aid of aluminum ions and glycerol (FIG. 40A). Since DNA is an insulator, these wire coatings showed complete electrical insulation (FIGS. 40B-40C). For 2D materials, a T-puzzle toy was created. Interestingly, the final products were similar to commercial, plastic products (FIG. 40D); they looked like plastics, sounded like plastics, and felt like plastics. For the 3D example, a biomass DNA spoon was fabricated from a mold (FIG. 40E). In order for biomass DNA to be viable as a potential replacement for petrochemical-based plastics, their safety was extremely important and needed to be evaluated extensively. Previously, it was shown that biomass DNA materials were biocompatible at the cellular level (FIGS. 19H-19I). Further standard animal acute toxicity experiments were conducted by feeding mice large amounts of biomass DNA plastic powder. Results clearly suggested that no toxicity was found in animal tests (FIG. 41). However, the dehydration of the DNA hydrogel was reversible, which implied that the water resistance of biomass DNA plastics needs to be improved in the future.

Example 6

This example describes the materials and methods used in the Example 1-5.

Materials. In this example, deoxyribonucleic acid sodium salt from salmon testes (D1626), poly (ethylene glycol) diacrylate (PEGDA, average Mn 575), insulin-FITC labeled, magnetic iron oxide particles, $TbCl_3 \cdot 6H_2O$, PEDOT:PSS, and 10, 12-pentacosadiynoic acid were purchased from Sigma-Aldrich. Sodium hydroxide (NaOH, ≥97%) and glycerol (anhydrous) were purchased from Fisher Scientific. DNase I (RNase-free), EcoRI, and T4 ligase was purchased from New England Biolabs (NEB). Au nanoparticles, SWCNT, GO, nanoclay (Laponite XLG), and ammonium hydroxide (28% NH3) were purchased from BBI Solutions, Carbon Solutions, Inc., Graphene Supermarket, Southern Clay Products Inc., and Alfa Aesar, respectively.

Figure 42:
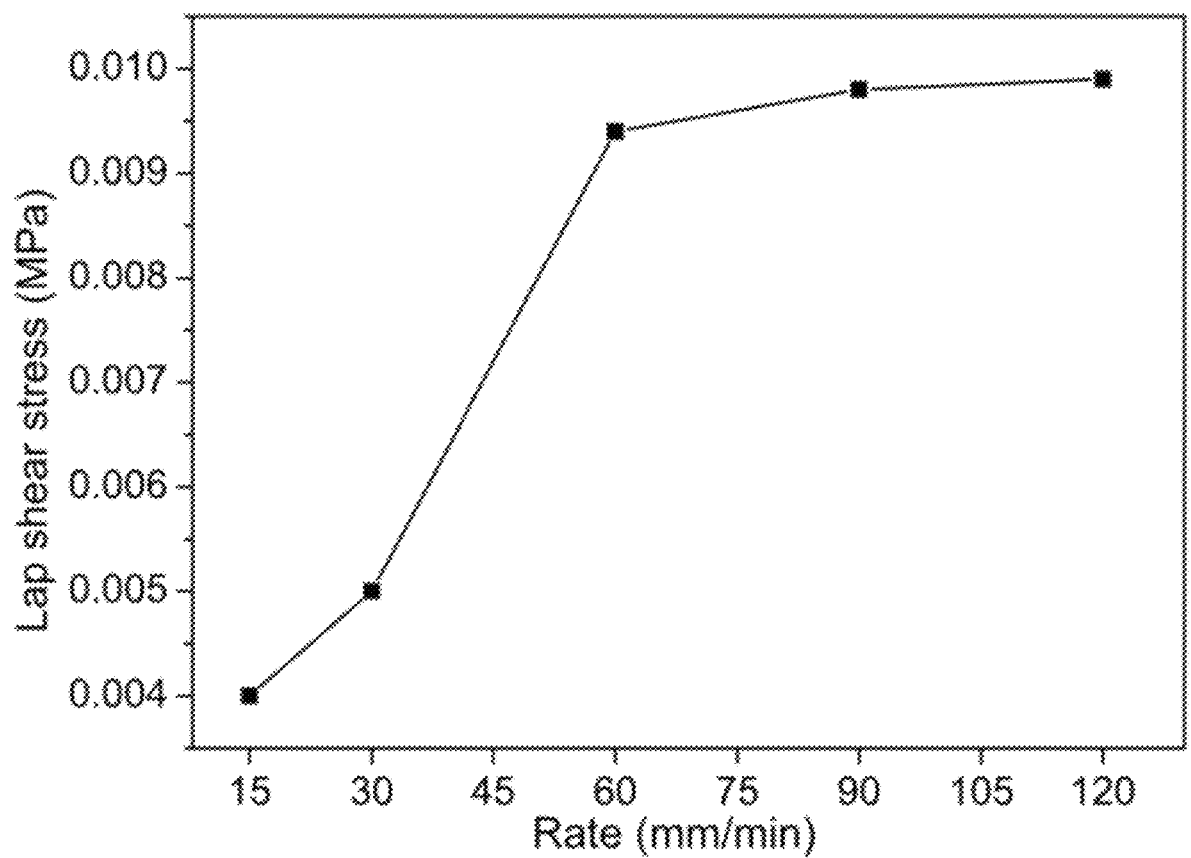
FIG. 42 shows the strain rate dependence of adhesive strength of biomass DNA organogels at room temperature.
Figure 43:
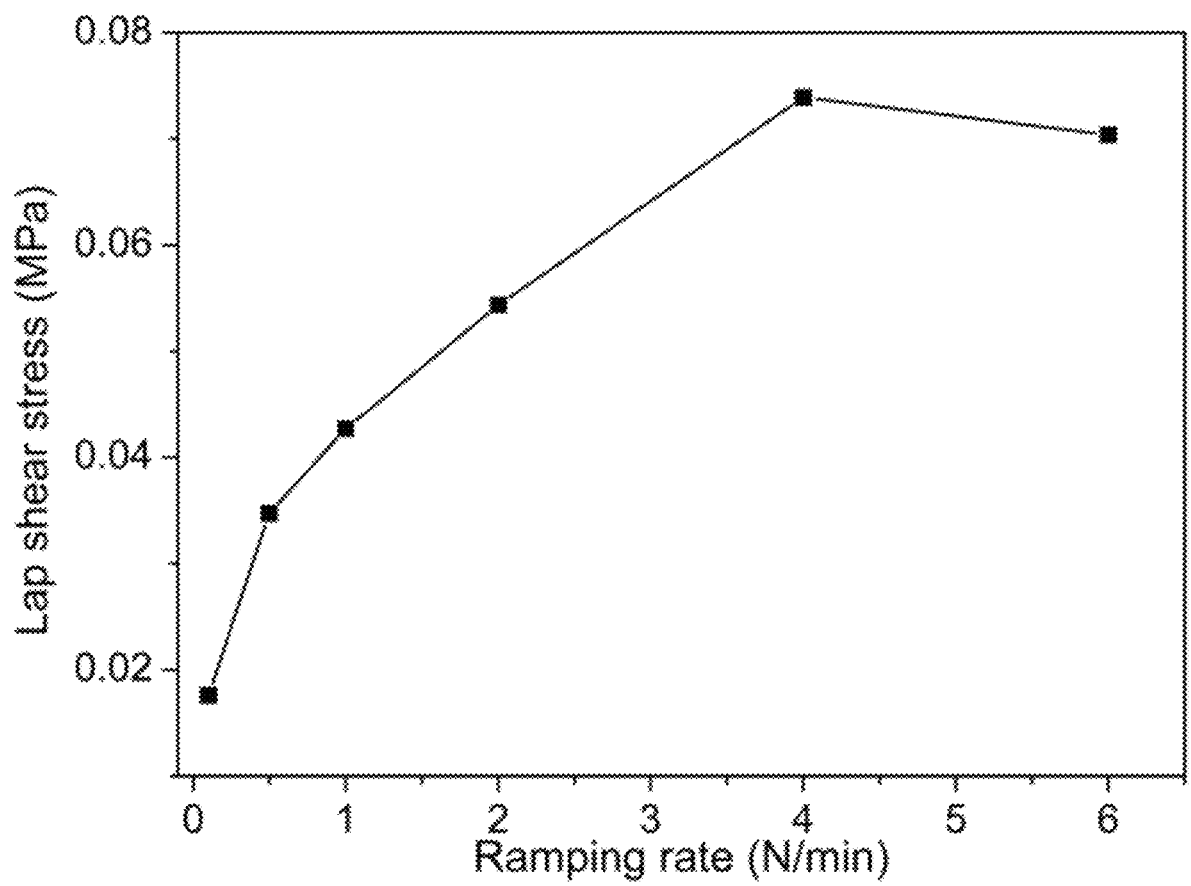
FIG. 43 shows the strain rate dependence of adhesive strength of biomass DNA organogels at -20° C.

The hydrogels were soaked by water and ethanol to remove the unreacted PEGDA and other impurities, then the ATR-FTIR of the lyophilized xerogels were collected on Bruker Hyperion FT-IR Spectrometer. The lyophilized hydrogels were used for scanning electronic microscopy (SEM) observation on Zeiss Gemini 500 Scanning Electron Microscope. LEO 1550 FESEM (Keck SEM) with a Bruker SDD X-ray Detector was used to observe the morphology of biomass DNA membranes and collect their Energy-dispersive X-ray spectroscopy (EDS) for elemental analysis. The confocal fluorescence images of biomass DNA membranes were taken on an Olympus FV1000 confocal laser scanning microscope. End-point fluorescence was measured in a 96-well plate using a PerkinElmer VictorX4 plate reader. The concentration of synthesized GFP was determined from a calibration curve (Ex 485 nm and Em 535 nm) done with purified 6×His tagged recombinant GFP expressed in $E.\ coli$ BL21 and further determined concentration with Bradford method. The mechanical properties and lap adhesive strengths at room temperature of biomass DNA gels were measured on an Instron 5965, the strain rate 60 mm/min or 90 mm/min was used for adhesive strength measurement (based on the results shown in FIG. 42). The lap adhesive strengths under freezing temperatures of biomass DNA gels were measured on a TA Instruments DMA Q800 Dynamic Mechanical analyzer, the strain rate 4 N/min was used for adhesive strength measurement (based on the results shown in FIG. 43).

Biomass DNA hydrogel. Preparation of biomass DNA hydrogel. Typically, for 8.3% DNA hydrogel, 60 mg of salmon testes DNA was dissolved into 600 μL of DI water with a gentle stirring. After adjusting the pH of solution by using 30 μL of NaOH (2.675 M) solution, 30 μL of PEGDA was added into the above solution and was mixed thoroughly for about 30 seconds. After eliminating air bubbles through centrifugation at 14,000×g for 20 seconds, the reaction solution was transferred into a mold (3.0 cm×0.8 cm×0.2 cm) within one minute, and the hydrogel formed within a half hour. For the tough hydrogel, the cross-linking reaction was continued for 10 h at the room temperature (22° C.). For the preparation of the hydrogels with different DNA contents, 30 mg of DNA and 15 μL of PEGDA were used for a 4.4% DNA hydrogel; 90 mg of DNA and 45 μL of PEGDA were used for a 11.7% DNA hydrogel. Other procedures were the same as those of 8.3% DNA hydrogel. The preparations of blue-green algae, $E.\ coli$, and onion DNA hydrogels were the same as those of salmon testes DNA.

Preparation of a large-scale biomass DNA hydrogel. Salmon testes DNA (2 g) was dissolved into 70 mL DI water (~3% DNA), and the pH of solution was adjusted by using 3.5 mL of NaOH (2.675 M) solution. Then, 1 g of PEGDA was added into the above solution and was mixed thoroughly. The mixture was coated on glass substrate (0.4 m×0.3 m) quickly before putting in a sealed container with water for 10 h at room temperature for the preparation of a large-scale hydrogel. To make the hydrogel easy to be seen, the hydrogel was colored by a food dye (Blue 1).

Preparation of a rubber-like biomass DNA hydrogel. Salmon testes DNA (60 mg) was dissolved into 300 μL DI water, and the pH of solution was adjusted by using 15 μL of NaOH (2.675 M) solution. Then, 75 μL of PEGDA was added into the above solution and was mixed thoroughly. The reaction solution was transferred into a mold (1.8 cm×0.8 cm×0.2 cm) within one minute, and then the reaction was continued for 10 h at room temperature for the preparation of a rubber-like hydrogel.

Swelling ratio. Swelling tests were conducted by using a gravimetric method. Lyophilized hydrogels with confirmed weights were immersed in electrolyte solution with different ionic strengths. At selected time intervals, the hydrated gels were taken out and wiped with filter paper to remove excess water from the gel surface and then weighed. The swelling ratio (SR) was calculated according to the following equation:

$$SR = W_t/W_d$$

where $W_d$ and $W_t$ denote the weight of the dried hydrogel and the weight of the swollen hydrogel, respectively.

Cytotoxicity of biomass DNA hydrogel. Cell Counting Kit-8 (CCK-8) (KeyGEN, China) was used to examine cell viability according to the manufacturer's instructions. Briefly, $1 \times 10^4$ MCF-7/Caco-2 cells were first seeded in each well of a 96-well plate and incubated at 37° C., 5% $CO_2$ for one day. The 8.3% biomass DNA hydrogels with different volumes were washed three times with 1×PBS, 75% ethanol, and DMEM. The increasing masses of hydrogel were added to the cells, and the mixtures were incubated in the 5% $CO_2$ for 4 h at 37° C. Then hydrogels in each culture well were removed from the cells with a sterile tweezers. A total of 100 μL of DMEM mixed with 10 μL of CCK-8 solution was added into each well of the 96-well plate and incubated for 4 h at 37° C. The absorbance of the medium in each well was measured at 450 nm with a microplate reader (PerkinElmer, victor X4, USA).

Controlled drug release from biomass DNA hydrogels. Insulin was loaded into biomass DNA hydrogels to assess the drug delivery capability. Salmon testes DNA (60 mg) was dissolved into 600 μL of DI water with a gentle stirring, and 30 μL of NaOH (2.675 M) solution was used for adjusting the pH of the solution. PEGDA (30 μL) was added into the above solution and was mixed thoroughly for about 30 seconds. After eliminating air bubbles through centrifugation at 14,000×g for 20 seconds, the reaction solution was transferred into a mold (3.0 cm×0.8 cm×0.2 cm) within one minute, the cross-linking reaction was continued for 10 h at room temperature. Then, the hydrogel was cut into three pieces (each one, 1.0 cm×0.8 cm×0.2 cm) and soaked in 10 mL NaCl solution (0.5 M) for 30 min, 10 mL 1×PBS (pH 7.4) for 30 min, and 10 mL DI water for 5 min to wash away the unreacted reagents. Three pieces of hydrogels were dried overnight at room temperature and then soaked in 5 mL ethanol for 6 h. Finally, three pieces of washed gels were dried once more overnight at room temperature for the following drug loading and release measurements. To load the FITC-labeled insulin, three pieces of dried gels were soaked in 4 mL 1×PBS with FITC-labeled insulin (200 μg/mL) for 24 h at room temperature under gentle shaking. Fluorescence intensities of supernatants were measured to determine the amounts of unloaded drugs. The average loading efficiency of FITC-labeled insulin was 21.3%, as calculated by the following equation:

$$\text{Loading efficiency} = \frac{\text{mass of fed drugs} - \text{mass of unloaded drugs}}{\text{mass of fed drugs}} \times 100\%$$

Figure 44:
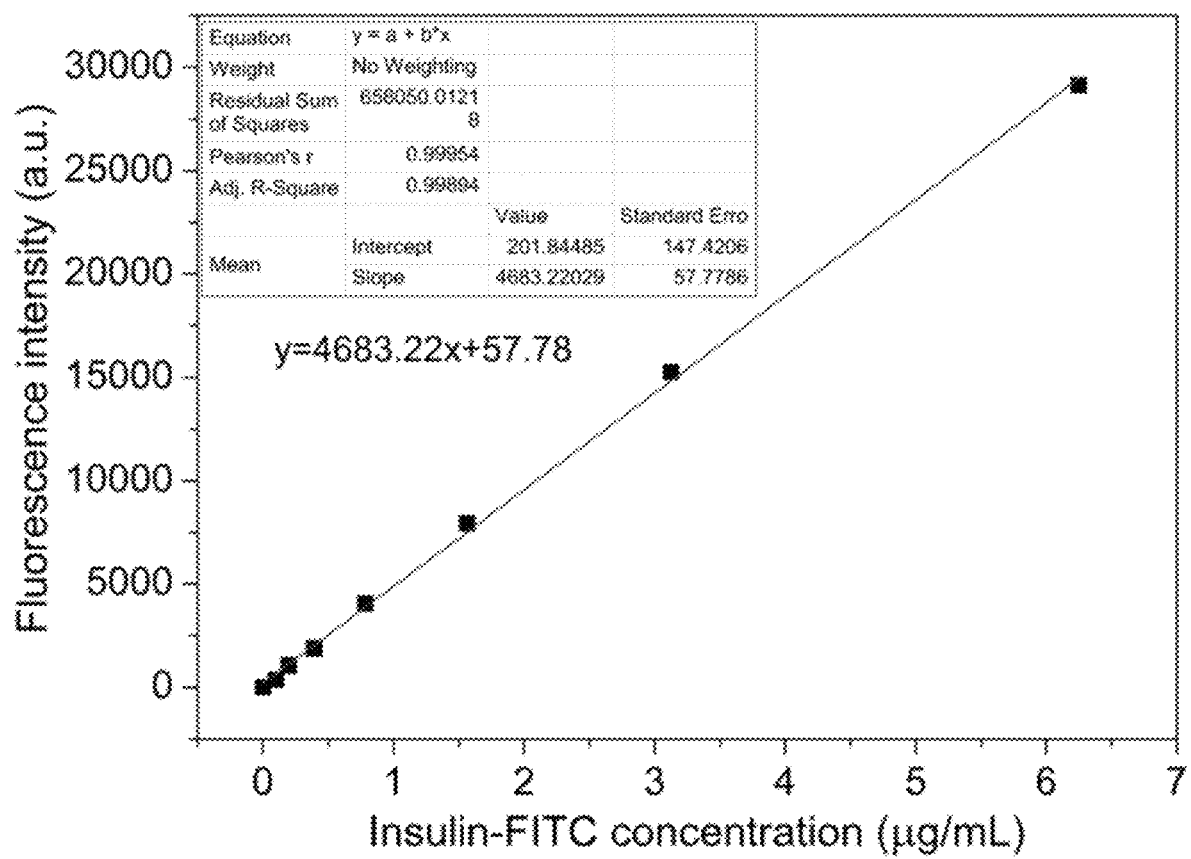
FIG. 44 shows the standard curve of insulin released from biomass DNA hydrogel.

For controlled release, the insulin-loaded hydrogels were soaked in 4 mL 1×PBS at 37° C. under gentle shaking (70 rpm). At predetermined time intervals, two milliliters of supernatant were taken out to be measured for the fluorescence intensity (insulin-FITC labeled at 520 nm) on a microplate reader (BioTek Synergy 4, USA) for the evaluation of insulin released from the DNA hydrogels. The concentrations of the insulin in incubation solution were determined from the standard curves (FIG. 44). After that, the incubation solution was refilled by 2 mL 1×PBS. The cumulative drug release was calculated by the following equation:

$$\text{Cumulative drug release (\%)} = \frac{V_e \sum_{1}^{n-1} C_i + V_0 C_t}{\text{initial mass of drug in hydrogel}} \times 100\%$$

where $V_e$ and $V_0$ are the volumes of incubation solution, ($V_0$=4 mL, $V_e$=2 mL), $C_t$ is the concentration of the drug in incubation solution at time t.

DNase I digestion of biomass DNA hydrogels. A biomass DNA hydrogel containing 4 mg DNA was prepared by following the preparation protocol of 8.3% DNA hydrogel. Then, the DNA hydrogel was incubated in 1 mL digestion solution (20 μL DNase I (2 U/μL), 100 μL reaction buffer, 840 μL DI water) for 17 h at 37° C. Then, the digestion results were characterized using gel electrophoresis (3% agarose, 100 V, 45 min).

Blue-green algae DNA extraction. Three grams of fresh blue green algae, Cyanobacteria, were ground in liquid nitrogen with 100 μm glass beads (Biospec Inc, China). Then, the ground powder was suspended in 15 mL extracting solution (0.02 mol/L EDTA, 100 mmol/L Tris-HCl (pH=8.0), 1.4 mol/L NaCl, 3% PVP, 2% CTAB, 2% 2-mecaptoethanol) with 20 mg pectinase. The suspension was incubated at 60° C. for 30 min and then centrifuged at 10,000×g for 10 min to remove the debris and the glass beads. Ten milliliters of chloroform/isopentanol (24:1) were added to the recovered supernatant. The mixture was incubated at room temperature for 10 min and centrifuged at 10,000×g for 10 min. The recovered supernatant was treated with chloroform/isopentanol (24:1) and centrifuged for additional three times until no precipitate can be observed at the interface of organic phase and aqueous phase. Ten milliliters of isopropanol were added to the recovered supernatant. The mixture was incubated at room temperature for 10 min and centrifuged at 8,000×g for 5 min. The precipitate was dissolved with 5 mL of double-distilled water (ddH$_2$O) and then was mixed with 0.75 mL 3 mol/L NaOAc and 12.5 mL absolute ethanol. The mixed solution was stored at −20° C. overnight and centrifuged at 10,000×g for 10 min. The precipitate was washed with 70% ethanol twice. The obtained blue green algae genomic DNA was freeze-dried for the hydrogel preparation described above.

E. coli DNA extraction. E. coli BL21 was used for bacterial genome DNA extraction. Monoclonal BL21 was inoculated into 5 mL of LB media to incubate at 37° C. for 8 h. This culture (600 μL) was added to 300 mL of LB media and incubated at 37° C. until the culture OD$_{600}$ reached 4 to 5. The cultured cells were pelleted with centrifugation at 5,000×g, 4° C. for 10 min. The bacteria pellet was ground in presence of liquid nitrogen by using a pre-chilled (−80° C.) mortar and pestle at room temperature. Forty milliliters of lysis buffer (0.05 mol/L Tris-HCl, pH 7.6, 0.1 mol/L NaCl, 0.05 mol/L EDTA, 2% SDS, 0.2% PVP, 0.1% β-mercaptoethanol) were added into one pellet from 100 mL culture, and then the mixture was incubated at 40° C. for 30 min. Cell debris and any other undissolved components were removed by a centrifugation at 12,000×g for 10 min. Ten milliliters of chloroform were added to the supernatant and mixed thoroughly; the mixture was allowed to sit at room temperature for 5 min. The mixture was centrifuged at 5,000×g for 5 min and the precipitate was discard. The procedure of chloroform treatment was repeated one more time. Two volumes of absolute ethanol and 0.1 volumes of 3 M sodium acetate (pH 5.2) were added to the supernatant. The mixture was stored at −20° C. for 30 min and then centrifuged at 12,000×g for 10 min. The precipitate was washed with 70% ethanol for 3 times and then dried at room temperature for the hydrogel preparation described above.

Onion DNA extraction. Five grams of onion slices were ground in a liquid nitrogen by using a pre-chilled mortar and pestle. Then, the ground powder was suspended in 20 mL of DNA extraction solution (0.1 mol/L Tris-HCl, pH 8.0, 0.02 mol/L EDTA (pH 8.0), 1.5 mol/L NaCl, 2% PVP40) with 100 μL of β-mercaptoethanol and 0.2 g of pectinase. The suspension was incubated at 50° C. for 40 min. Then, the suspension was treated with an equal volume of chloroform/isoamyl alcohol (24:1) and centrifuged at 13,000×g for 10 min. The procedure of chloroform/isoamyl alcohol (24:1) treatment was repeated one more time. Ice-prechilled isopropanol (0.6 volumes) was added to the supernatant. The solution was mixed and stored at room temperature for 30 min. The flocculent DNA was spooled out with a glass rod and washed 3 times with 70% alcohol. Then, the onion DNA was washed once with 100% alcohol and dried in air for the hydrogel preparation described above.

Figure 45:
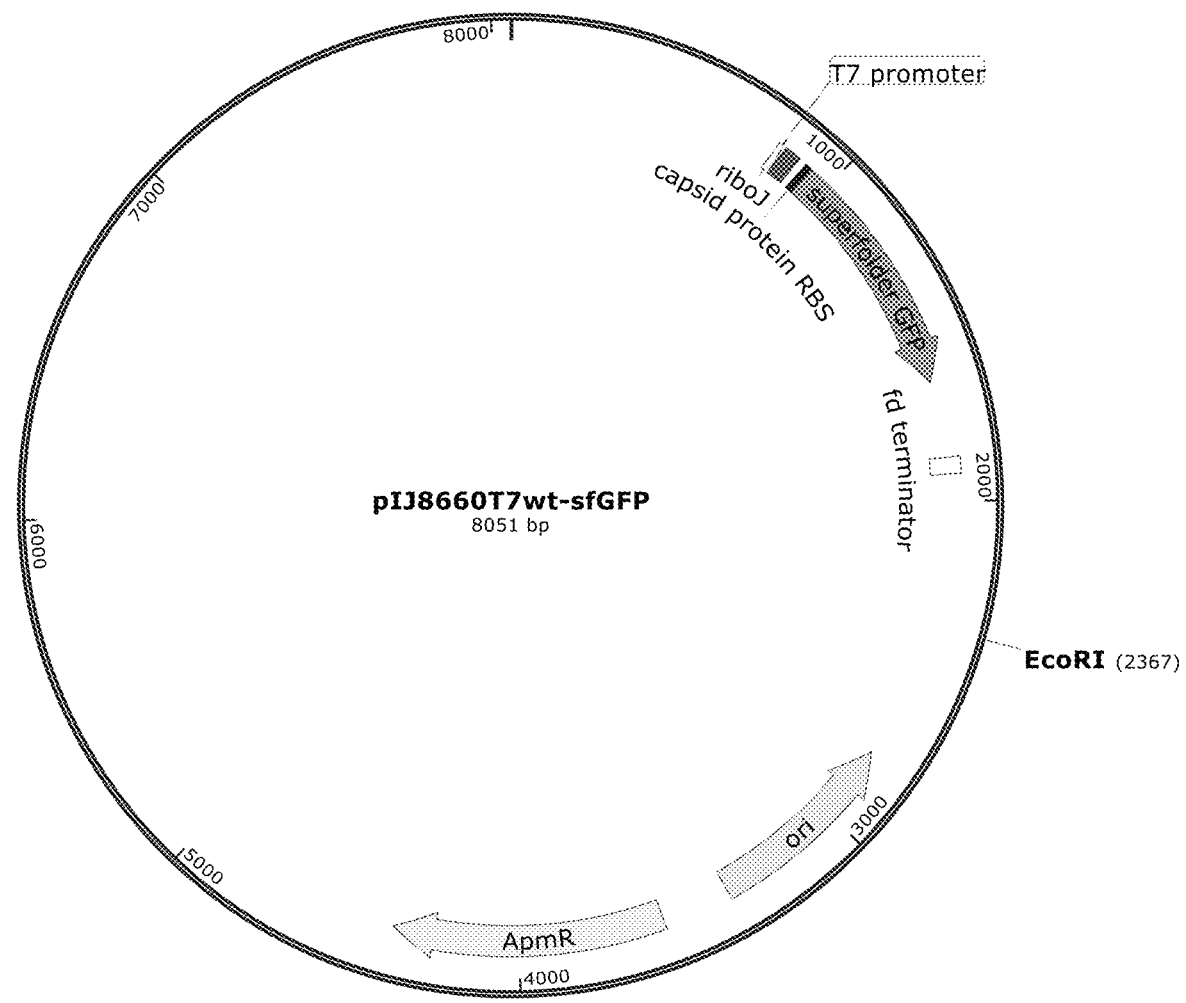
FIG. 45 shows a circular and linearized plasmid map.

Plasmid amplification. Plasmid pIJ8660T7 wt-GFP (FIG. 45) was a gift from Professor Lixin Zhang's Lab, Institute of Microbiology, Chinese Academy of Sciences. The competent cells DH5α were used as the host strain (TIANGENBIOTECH CO., LTD) for the plasmid amplification according to manufacturer's protocol.

Figure 46:
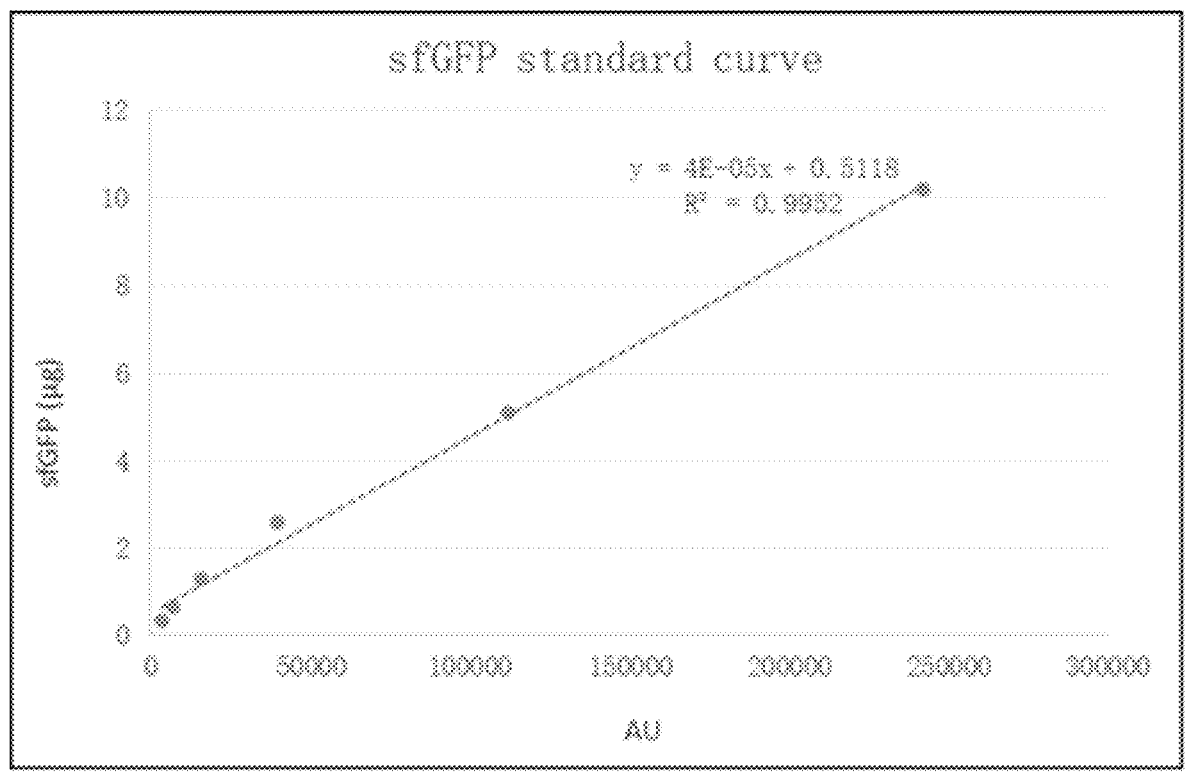
FIG. 46 shows the standard curve of GFP expressed from biomass DNA hydrogel.

Cell-free protein production with DNA hydrogels. To produce green fluorescent protein (GFP) using salmon testes DNA hydrogels, salmon testes DNA gel and plasmid (pIJ8660T7 wt-GFP with a high fidelity restriction endonuclease EcoRI (NEB cat: R3101) were digested at 37° C. overnight and ligated together with T4 ligase (NEB cat: M0202T) by mass ratio 30:1 at room temperature for 3 h. Then, crosslinked DNA gel containing 24 μg of salmon testes DNA and 800 ng of plasmids was used for cell-free protein production in a solution containing 6.67 μL of cell-free lysate, 10.73 μL of reaction buffer, and 0.6 μL of nuclease-free water. Cell-free reactions (20 μL) were incubated at 30° C. in a thermomixer (Eppendorf Thermomixer C) with 1,000 rpm for 15 h. End-point fluorescence was used to determinate the concentration of GFP products according to a GFP standard curve (FIG. 46).

The crude extract was prepared as previously described with slight modifications. E. coli BL21 Rosetta2 DE3 strain was used as lysate source. Isopropyl-thiogalactopyranoside (IPTG, 1 mM) was added to the culture media to induce production of T7 RNA polymerase when culture OD600 reached 0.6.

The cell-free reaction buffer was composed of: 50 mM HEPES (pH 8), 1.5 mM ATP and GTP, 0.9 mM CTP and UTP, 0.2 mg/ml tRNA, 0.26 mM coenzyme A, 0.33 mM NAD, 0.75 mM cAMP, 0.068 mM folinic acid, 1 mM spermidine, 30 mM 3-PGA, 1 mM DTT, 2% PEG8000, and 3 mM of each of the 20 amino acids. The Mg-glutamate and K-glutamate concentrations were 4 nM and 80 nM, respectively. The recipes of above preparation and cell-free protein production of plasmid-decorated biomass DNA hydrogel were shown in Table 3.

TABLE 3

The recipes of the preparation and cell-free protein production of plasmid-decorated biomass DNA hydrogel.

EcoRI HF digestion for salmon testes DNA and plasmid (37° C., incubated overnight. 65° C., incubated for 20 min to inactivate enzyme).

| Salmon testes DNA | Vol. | Amt. | Final conc. |
|---|---|---|---|
| 100 μg/μL salmon testes DNA gel | 10 μL | 1000 μg | 50 μg/μL |
| 10x EcoRI buffer | 2 μL | | |
| 20 U/μL EcoRI | 1 μL | 20 U | |
| ddH₂O | 7 μL | | |
| Total | 20 μL | | |
| Plasmid | Vol. | Amt. | Final conc. |
| 2.66 μg/μL pIJ8660T7we-GFP | 15 μL | 40 μg | 2000 ng/μL |
| 10x EcoRI buffer | 2 μL | | |
| 20 U/μL EcoRI | 1 μL | 20 U | |
| ddH₂O | 2 μL | | |
| Total | 20 μL | | |

T4 ligase crosslink salmon testes DNA and pIJ8660T7wt-GFP (25° C., 3 h).

| | Vol. (μL) | Amt. | Mass ratio | Final conc. |
|---|---|---|---|---|
| Digest pIJ8660T7-GFP (2000 ng/μL) | 2 | 4000 ng | 1 | 400 ng/μL |
| Digested salmon testes DNA (50 μg/μL) | 2.4 | 120 μg | 30 | 12 μg/μL |

TABLE 3-continued

The recipes of the preparation and cell-free protein production of plasmid-decorated biomass DNA hydrogel.

| 10x T4 ligase buffer | 1 | |
| T4 ligase (2000 U/μL) | 1 | 2000 U |
| ddH₂O | 3.6 | |
| Total | 10 | |

Biomass DNA organogels. Preparation of biomass DNA organogels. Salmon testes DNA (60 mg) was separately dissolved into 600, 540, 420, 300, 180 and 60 μL of DI water with occasionally and a gentle stirring. When the mixtures became transparent, glycerol was added into the mixtures to keep same total volume (600 μL). The initial glycerol contents (wt %) (glycerol/water+glycerol) were 0%, 12%, 34%, 54% and 72%. After the DNA dissolved completely in mixed solvents of water and glycerol with a gentle string, 30 μL of NaOH (2.675 M) solution were separately added the solutions to adjust their pH. PEGDA (30 μL) were separately added into above solutions and mixed thoroughly for about 30 seconds. After eliminating air bubbles through centrifugation at 14,000×g for 20 seconds, the six reaction solutions were transferred into six molds (3.0 cm×0.8 cm×0.2 cm) within one minute. The cross-linking reaction was continued for 10 h at room temperature (22° C.). The biomass DNA gels were taken out from molds and dehydrated under at room temperature (22° C.) with 14% relative humidity. The mass variations of gels were recorded to monitor the changes of water and glycerol in gels. One day later, the water and glycerol contents kept constant under stable relative humidity. Then, the prepared biomass DNA organogels were used for the following experiments.

Gas-triggered biomass DNA membranes. Preparation of biomass DNA membranes. Salmon testes DNA (10 mg) was dissolved into 250 μL of 4.3% (wt %) PEGDA aqueous solution with a gentle stirring to prepare a precursor solution. The precursor solution (200 μL) was spin-coated on a cover glass (22 mm×22 mm) (spin-coating parameters: 500 rpm for 5 s, 1,800 rpm for 5 s). After that, the thin precursor layer with substrate was put in a chamber with 28% ammonia solution. One hour later, the biomass DNA thin membrane formed, and was peeled off in 0.5 M sodium chloride solution for the following experiments.

Preparation of a large-scale biomass DNA membrane. Salmon testes DNA (2 g) was dissolved into 70 mL DI water (~3% DNA), 1 g of PEGDA was added into above solution and mixed thoroughly. The mixture was coated on glass substrate (0.4 m×0.3 m), and then put in sealed container with 28% ammonia solution for 3 h at room temperature to prepare the large-scale biomass DNA membrane. To make the membrane easy to be seen, the hydrogel was colored by a food dye (Blue 1).

Preparation of biomass DNA composite membranes. For DNA-SWCNT composite membrane, 2 mg of biomass DNA was dissolved in 2 mL DI water and sonicated for 15 min at 0° C., then 1 mg of SWCNT was sonicated in 2 mL the above solution for 2.5 h at 0° C. the solution was divided into 0.5 mL aliquots and centrifuged at 16,000×g for 90 min to remove insoluble SWCNT (3). The mass concentration of SWCNT was about 0.04 mg/mL and vacuum-centrifuged to 0.1 mg/mL before use. Salmon testes DNA (10 mg) was dissolved into 250 μL of SWCNT dispersion with 4.3% PEGDA with a gentle stirring for the precursor solution. The preparation of gas-triggered biomass DNA-SWCNT membrane was the same as that of biomass DNA membrane. For other composite membranes, all the dopants were procured from commercial sources. Salmon testes DNA (10 mg) was separately dissolved into 250 μL of GO dispersion (concentrated to 1.5 mg/mL before use) with 4.3% PEGDA, 250 μL of Au nanoparticles (40 nm) dispersion with 4.3% PEGDA, 250 μL of magnetic iron oxide particles dispersion (10 mg/mL) with 4.3% PEGDA, 250 μL of 1% nanoclay dispersion with 4.3% PEGDA, and 250 μL of 0.6% PEDOT: PSS solution with 4.3% PEGDA. The preparation of composite membranes was the same as that of the biomass DNA membrane. For DNA-PDA composite membrane, 1 mg of 10, 12-pentacosadiynoic acid was dispersed in 1 mL DI water by sonication (30 min), then salmon testes DNA (10 mg) was dissolved into 250 μL of 10, 12-pentacosadiynoic acid dispersion with 4.3% PEGDA. After ammonia-trigged membrane formed, the membrane was irradiated by UV light (254 nm) for 20 min. For DNA-Tb' composite membrane, a freshly prepared biomass DNA membrane was left for 40 min to allow the ammonia and water to volatilize. Then, the membrane was soaked in 10 mL Tb$^{3+}$ solution (0.1 M) for 20 min. All these biomass DNA membranes were stained by GelRed or SYBR Green I for fluorescence images.

Patterning of biomass DNA-SWCNT membranes (etching method). Two freshly prepared biomass DNA-SWCNT membranes were left for 5 min to allow the ammonia to volatilize completely. The membranes were covered by a plasma-treated PDMS mask with a smiley face and a PDMS mask with diamond-shaped holes. A digestion solution (240 μL) was added in the holes of the masks, then the reaction systems were sealed. The digestion reaction was continued for 20 min at room temperature (22° C.). The digestion solutions were washed away using 0.5 M sodium chloride solution, and then the patterned membranes were peeled off in 0.5 M sodium chloride solution and stained by GelRed or SYBR Green I. The digestion solution (120 μL) was comprised of 4 μL of DNase I, 12 μL of reaction buffer (10×), and 104 μL of DI water.

Patterning of biomass DNA membranes (direct writing method). Two freshly prepared biomass DNA membranes were left for 5 min to allow the ammonia to volatilize completely. The membranes were covered by a plasma-treated PDMS mask with a smiley face and a PDMS mask with diamond-shaped holes. The 0.1 M Tb' solution was sprayed on the masked membranes, and the reaction was continued for 2 min. The Tb' solution was washed away using 0.5 M sodium chloride solution, and then the patterned membranes were peeled off in 0.2 M sodium chloride solution.

Preparation of a biomass DNA flower. Green fluorescent biomass DNA-SWCNT precursor solution was comprised of 10 mg of salmon testes DNA, 10 μL of PEGDA, 250 μL of DI water, and 0.5 μL of SYBR Green I. Crimson fluorescent biomass DNA-iron oxide particles precursor solution was comprised of 10 mg of salmon testes DNA, 10 μL of PEGDA, 250 μL of DI water, and 2.5 μL of SYTO 64 Red. The green fluorescent biomass DNA-SWCNT precursor solution (70 μL) and the crimson fluorescent biomass DNA-iron oxide particles precursor solution (50 μL) were separately added into different petals of a flower pattern. One hour later, a four-component DNA flower was constructed with two different types of petals.

Biomass DNA plastics. Biomass DNA coating of copper wires (1D). Salmon testes DNA (50 mg) was dissolved into 1 mL of DI water with food dyes. A copper wire was coated by the above DNA solution and put in a mixture of 0.5 mL of glycerol and 10 mL of aluminum chloride solution (0.1 M) for 3 min. The coated copper wire was soaked in a mixture of 10 mL of DI water and 0.1 mL glycerol for 10 min and dried for 1 h at room temperature. This process was repeated 10 times, then the coated cooper wire was dried out at room temperature.

Figure 47:
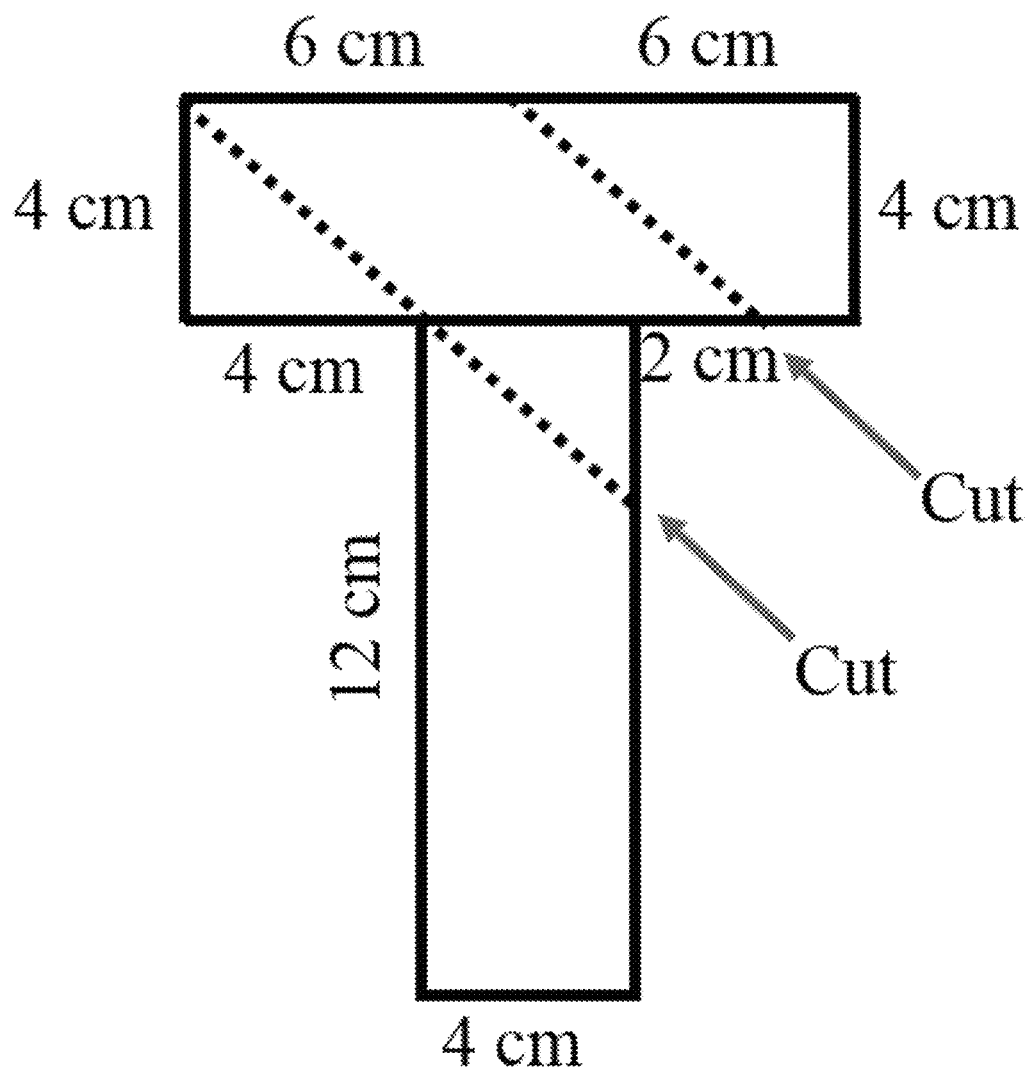
FIG. 47 shows the dimensions of the T-puzzle mold (depth was 4 mm).

Preparation of a set of biomass DNA T-puzzle (2D). Salmon testes DNA (2.2 g) was dissolved into 27 mL DI water (~8% DNA), and the pH of solution was adjusted by using 1.2 mL of NaOH (2.675 M) solution. PEGDA (0.99 mL) was added into the above solution and was mixed thoroughly. The mixture was poured into a mold quickly (FIG. 47), and then the reaction was continued for 10 h at room temperature for the preparation of a T-shaped hydrogel. The T-shaped hydrogel was cut into four pieces before soaking in 0.5 M sodium chloride solution with different food dyes for 2 h. After that, these colored hydrogels were dried for one week at room temperature for a set of biomass DNA plastic toys, T-puzzle.

Preparation of a biomass DNA spoon (3D). Salmon testes DNA (600 mg) was dissolved into 6.0 mL of DI water, the pH of solution was adjusted by using 300 μL of NaOH (2.675 M) solution. PEGDA (300 μL) was added into the above solution and was mixed thoroughly. The mixture was poured in a mold quickly, and then the reaction was continued for 10 h at room temperature for the preparation of a biomass DNA hydrogel spoon. The hydrogel spoon was dried for five days at room temperature for a biomass DNA spoon.

Evaluation of oral acute toxicity of biomass DNA plastics. Acute toxicity of biomass DNA plastic on mice was evaluated according to the standard OECD/OCDE guideline 423. Briefly, female ICR mice weighing 18-22 g were randomly divided into four groups (n=8 for each group). The biomass DNA plastic treated group were administered by the oral route at doses of 500 mg/kg, 1,000 mg/kg, and 2,000 mg/kg body weight. The control group were treated by oral gavage with saline. Then, all mice were housed with free access to food and water and observed for a total of two weeks. The survival rates in all groups and individual weights of mice were recorded every week.

Although the present disclosure has been described with respect to one or more particular examples, it will be understood that other examples of the present disclosure may be made without departing from the scope of the present disclosure.

The invention claimed is:

1. A method of making a plurality of crosslinked nucleotide polymers and/or polymeric materials comprising nucleotide polymer groups comprising:
    modifying at least a portion or all of the nucleotide polymers in a biomass with a functional group chosen from aliphatic groups, aryl groups, and combinations thereof to form functionalized nucleotide polymers; and
    reacting the biomass comprising nucleotide polymers with one or more crosslinkers, the individual crosslinker(s) comprising one or more Michael acceptor(s), wherein a plurality of crosslinked nucleotide polymers is formed.

2. A method of claim 1, wherein the biomass and the crosslinker(s) are present in a mixture and the mixture comprises one or more solvent(s).

3. A method of claim 2, wherein the solvent(s) is/are chosen from water, ionic liquids, and combinations thereof.

4. A method of claim 2, wherein the mixture is an aqueous mixture and the pH of the mixture is greater than 7.

5. A method of claim 1, wherein the Michael acceptor(s) are activated alkene groups.

6. A method of claim 1, wherein the Michael acceptor(s) is/are chosen from alpha,beta unsaturated ketone groups, alpha,beta unsaturated aldehylde groups, alpha,beta unsaturated ester groups, alpha, beta unsaturated amide groups, alpha, beta unsaturated nitrile groups, and nitro ethylene groups, and combinations thereof.

7. A method of claim 1, wherein the crosslinker(s) is/are chosen from polyethylene glycol dimethacrylate (PEGDMA), poly (ethylene glycol) diacrylate (PEGDA), four-arm PEG acrylate, divinyl sulfone (DVS), and combinations thereof.

8. A method of claim 1, further comprising enzymatic treatment of the biomass comprising nucleotide polymers prior to reaction with oligomer crosslinker(s) and/or polymer crosslinker(s) or after formation of the crosslinked nucleotide polymers.

9. A method of claim 1, wherein the biomass and oligomer crosslinker(s) and/or polymer crosslinker(s) are present in a mixture and the mixture comprises one or more organic solvent(s).

10. A method of claim 9, wherein the organic solvent(s) is/are chosen from alcohols, ionic liquids, formamide, and combinations thereof.

11. A method of claim 1, wherein one or more additive(s) is/are added to a reaction mixture comprising the biomass and the one or more crosslinkers before the crosslinking reaction and/or to the plurality of crosslinked nucleotide polymers.

12. A method of claim 11, wherein the additive(s) is/are chosen from functional materials, inorganic materials, plasticizers, polymerizable monomers, and combinations thereof.

13. The method of claim 1, wherein the nucleotide polymers are DNA.

14. The method of claim 1, wherein the biomass comprises at least 4% DNA.

15. The method of claim 1, wherein the reaction mixture further comprises a base in a gaseous form.

16. The method of claim 1, wherein the plurality of crosslinked nucleotide polymers form a membrane.

17. The method of claim 1, wherein the plurality of crosslinked nucleotide polymers form a hydrogel.

18. The method of claim 1, wherein a reaction mixture further comprises carbon nanotubes, metal ions, clays, rare earth compounds, metal particles, metal oxide particles, and combinations thereof.

19. The method of claim 1, wherein the biomass does not comprise intact cells.

20. A method of making a plurality of crosslinked nucleotide polymers and/or polymeric materials comprising nucleotide polymer groups comprising:

reacting in a reaction mixture comprising a biomass comprising nucleotide polymers, wherein the biomass does not comprise intact cells, with one or more crosslinkers, the individual crosslinker(s) comprising one or more Michael acceptor(s), wherein a plurality of crosslinked nucleotide polymers is formed.

21. The method of claim 20, wherein the biomass comprises at least 4% DNA.

22. The method of claim 20, wherein the reaction mixture further comprises a base in a gaseous form.

23. The method of claim 20, wherein the plurality of crosslinked nucleotide polymers form a membrane.

24. The method of claim 20, wherein the plurality of crosslinked nucleotide polymers form a hydrogel.

25. The method of claim 20, wherein a reaction mixture further comprises carbon nanotubes, metal ions, clays, rare earth compounds, metal particles, metal oxide particles, and combinations thereof.

* * * * *